United States Patent
Coe

(10) Patent No.: US 6,462,035 B1
(45) Date of Patent: Oct. 8, 2002

(54) ARYL FUSED AZAPOLYCYCLIC COMPOUNDS

(75) Inventor: Jotham Wadsworth Coe, Niantic, CT (US)

(73) Assignee: Pfizer Inc., New York, NY (US)

(*) Notice: Subject to any disclaimer, the term of this patent is extended or adjusted under 35 U.S.C. 154(b) by 0 days.

(21) Appl. No.: 09/582,513

(22) PCT Filed: Apr. 8, 1999

(86) PCT No.: PCT/IB99/00617

§ 371 (c)(1),
(2), (4) Date: Aug. 7, 2000

(87) PCT Pub. No.: WO99/55680

PCT Pub. Date: Nov. 4, 1999

Related U.S. Application Data

(60) Provisional application No. 60/083,556, filed on Apr. 29, 1998.

(51) Int. Cl.[7] .................. A61K 31/33; C07D 225/00; C07D 225/04
(52) U.S. Cl. .................. 514/183; 514/290; 540/476; 540/479; 540/482
(58) Field of Search .................. 514/183, 290; 540/476, 479, 482

(56) References Cited

U.S. PATENT DOCUMENTS 3,687,937 A * 8/1972 Wiesner et al. .......... 260/239.3

OTHER PUBLICATIONS

Chang et al"Synthesis & Analgetic . . . of benzocines", J.Med.Chem. 14/10, 1011–3(1971).*
Kometani et al"Synthesis of Homobenzomorphans . . .", Chem.Pharm.Bull.,24/3,541–44(1976).*
Kitahonoki et al"Stereochem. of Aziridine Formation from Ketoximes . . ."Tetrahedron Let.25,335–53(1969).*
Kitahonoki et al"Stereochem. of Aziridine Formation by . .", Tetrahedron Letter.*
Chang et al., "Synthesis and analgetic Activity of 1,5–Methano–3–methyl–benzazocines", J.Med.Chem.14/10,1011–3(1971).*

Chang et al., "Synthesis and Analgetic Activity of 1,5–Methano–3–methyl–1,2,3,4,5, 6–hexahydro–3–benzazocines," *J. Med. Chem.* 14(10), pp 1011–3 (1971).

Kitahonoki et al., "Stereochemistry of Aziridine Formation From Ketoximes of Bridged Ring Systems By Lithium Aluminum Hydride Reduction On Benzobicyclo[3.2.1] octenone Oximes," *Tetrahedron*, 25, pp. 335–353 (1969).

Kometani et al., "Synthesis of Homobenzomorphans And The Related Compounds. III 3–Methyl–2,3,4,5,6,7–hexahydro–1,6–methano–1H–3–benzazonine," *Chem. Pharm. Bull.*, 24(3), pp. 541–544 (1976).

Kitahonoki et al., "Stereochemistry Of Azidine Formation By Lithium Aluminum Hydride Reduction Of Ketoximes Of Bridged Ring Systems On Benzobicyclo[3.2.1]octenonone Oximes," *Tetrahedron Letter*, 13, pp. 1651–1655 (1968).

Masuda et al., "Benzazocines," Chemical Abstracts, 81(13), Abstr. No. 77812w (Sep. 30, 1974).

Masuda et al., "Benzazocines," Chemical Abstracts, 80(19), Abstr. No. 108399c (May13, 1974).

* cited by examiner

Primary Examiner—Mukund J. Shah
Assistant Examiner—Sudhaker B. Patel
(74) Attorney, Agent, or Firm—P. C. Richardson; P. H. Ginsburg; A. D. Joran

(57) ABSTRACT

The present invention relates to compounds of formula (I)

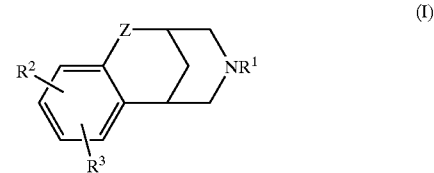

and their pharmaceutically acceptable salts, wherein $R^1$, $R^2$, $R^3$ and Z are as defined herein, intermediates in the synthesis of such compounds, pharmaceutical compositions containing such compounds and methods of using such compounds in the treatment of neurological and psychological disorders.

10 Claims, No Drawings

ARYL FUSED AZAPOLYCYCLIC COMPOUNDS

This application is the National Stage of International application No. PCT/IB99/00617, filed Apr. 8, 1999, which claims the benefit of provisional U.S. application Ser. No. 60/083,556, filed Apr. 29, 1998.

BACKGROUND OF THE INVENTION

This invention relates to aryl fused azapolycyclic compounds, as defined more specifically by formula I below. Compounds of formula I bind to neuronal nicotinic acetylcholine specific receptor sites and are useful in modulating cholinergic function. Such compounds are useful in the treatment of inflammatory bowel disease (including but not limited to ulcerative colitis, pyoderma gangrenosum and Crohn's disease), irritable bowel syndrome, spastic dystonia, chronic pain, acute pain, celiac sprue, pouchitis, vasoconstriction, anxiety, panic disorder, depression, bipolar disorder, autism, sleep disorders, jet lag, amyotrophic lateral sclerosis (ALS), cognitive dysfunction, hypertension, bulimia, anorexia, obesity, cardiac arrhythmias, gastric acid hypersecretion, ulcers, pheochromocytoma, progressive supranuclear palsy, chemical dependencies and addictions (es, dependencies on, or addictions to nicotine (and/or tobacco products), alcohol, benzodiazepines, barbiturates, opioids or cocaine), headache, stroke, traumatic brain injury (TBI), obsessive-compulsive disorder, psychosis, Huntington's Chorea, tardive dyskinesia, hyperkinesia, dyslexia, schizophrenia, multi-infarct dementia, age related cognitive decline, epilepsy, including petit mal absence epilepsy, senile dementia of the Alzheimer's type (AD), Parkinson's disease (PD), attention deficit hyperactivity disorder (ADHD) and Tourette's Syndrome.

The compounds of this invention may also be used in combination with an antidepressant such as, for example, a tricyclic antidepressant or a serotonin reuptake inhibiting antidepressant (SRI), in order to treat both the cognitive decline and depression associated with AD, PD, stroke, Huntington's Chorea or traumatic brain injury (TBI); in combination with muscarinic agonists in order to stimulate both central muscarinic and nicotinic receptors for the treatment, for example, of ALS, cognitive dysfunction, age related cognitive decline, AD, PD, stroke, Huntington's Chorea and TBI; in combination with neurotrophic factors such as NGF in order to maximize cholinergic enhancement for the treatment, for example, of ALS, cognitive dysfunction, age related cognitive decline, AD, PD stroke, Huntington's Chorea and TBI; or in combination with agents that slow or arrest AD such as cognition enhancers, amyloid aggregation inhibitors, secretase inhibitors, tau kinase inhibitors, neuronal antiinflammatory agents and estrogen-like therapy.

Other compounds that bind to neuronal nicotinic receptor sies are referred to in U.S. patent application Ser. No. 08/963,852, which was filed on Nov. 4, 1997, and in U.S. Provisional Patent Application No. 60/070,245, which was filed on Dec. 31, 1997. Both of the foregoing applications are owned in common with the present application, and both are incorporated herein by reference in their entireties.

SUMMARY OF THE INVENTION

This invention relates to aryl fused azapolycyclic compounds of the formula

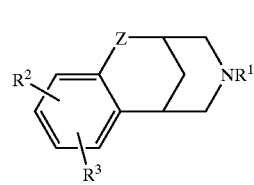

wherein

Z is $CH_2$, $C(=O)$ or $CF_2$;

$R^1$ is hydrogen, $(C_1-C_6)$alkyl, unconjugated $(C_3-C_6)$ alkenyl, benzyl, $XC(=O)R^{13}$ or $—CH_2—CH_2—O—(C_1-C_4)$alkyl;

$R^2$ and $R^3$ are selected independently, from hydrogen, $(C_2-C_6)$, alkenyl, $(C_2-C_6)$ alkynyl, hydroxy, nitro, amino, halo, cyano, $—SO_q(C_1-C_6)$alkyl wherein q is zero, one or two, $(C_1-C_6)$alkylamino, $[(C_1-C_6)$alkyl$]_2$amino, $CO_2R^4$, $CONR^5R^6$, $SO_2NR^7R^8$, $C(=O)R^{13}$, $XC(=O)R^3$, aryl$(C_0-C_3)$ alkyl or aryl-$(C_0-C_3)$ alky-O-, wherein said aryl is selected from phenyl and naphthyl, heteroaryl-$(C_0-C_3)$alkyl or heteroaryl-$(C_0-C_3)$alkyl-O, wherein said heteroaryl is selected from five to seven membered aromatic rings containing from one to four heteroatoms selected from oxygen, nitrogen and sulfur, and $X^2(C_0-C_6)$alkoxy-$(C_0-C_6)$ alkyl, wherein $X^2$ is absent or $X^2$ is $(C_1-C_6)$alkylamino or $[(C_1-C_6)$alkyl$]_2$amino, and wherein the $(C_0-C_6)$ alkoxy-$(C_0-C_6)$alkyl moiety of said $X^2(C_0-C_6)$alkoxy-$(C_1-C_6)$alkyl contains at least one carbon atom, and wherein from one to three of the carbon atoms of said $(C_0-C_6)$alkoxy-$(C_0-C_6)$alkyl moiety may optionally be replaced by an oxygen, nitrogen or sulfur atom, with the proviso that any two such heteroatoms must be separated by at least two carbon atoms, and wherein any of the alkyl moieties of said $(C_0-C_6)$alkoxy-$(C_0-C_6)$alkyl may be optionally substituted with from two to seven fluorine atoms, and wherein one of the carbon atoms of each of the alkyl moieties of said aryl$(C_0-C_3$alkyl and said heteroaryl-$(C_0-C_3)$alkyl may optionally be replaced by an oxygen, nitrogen or sulfur atom, and wherein each of the foregoing aryl and heteroaryl groups may optionally be substituted with one or more substituents, preferably from zero to two substituents, independently selected from $(C_1-C_6)$alkyl optionally substituted with from one to seven fluorine atoms, $(C_1-C_6)$ alkoxy optionally substituted with from two to seven fluorine atoms, halo (e.g., chloro, fluoro, bromo or iodo), hydroxy, nitro, cyano, amino, $(C_1-C_6)$ alkylamino and $[(C_1-C_6)$alky$]_2$ amino;

or $R^2$ and $R^3$, together with the carbons to which they are attached, form a four to seven membered monocyclic, or a ten to fourteen membered bicyclic, carbocydic ring that can be saturated or unsaturated, wherein from one to three of the nonfused carbon atoms of said monocyclic rings, and from one to five of the carbon atoms of said bicyclic rings that are not part of the benzo ring shown in formula I, may optionally and independently be replaced by a nitrogen, oxygen or sulfur, and wherein said monocydic and bicyclic rings may optionally be substituted with one or more substituents, preferably from zero to two substituents for the monocyclic rings and from zero to three substituents for the bicyclic rings, that are selected, independently, from $(C_0-C_6)$ alkoxy-$(C_0-C_6)$alkyl, wherein the total number of carbon atoms does not exceed six and wherein any of the alkyl moieties may optionally be substituted with from one to seven fluorine atoms; nitro, oxo, cyano, halo, hydroxy, amino, $(C_1-C_6)$alkylamino, $[(C_1-C_6)alkyl]_2$amino, phenyl and monocyclic heteroaryl wherein said heteroaryl is defined as in the definition of $R^2$ and $R^3$ above;

each $R^4$, $R^5$, $R^6$, $R^7$, $R^8$ and $R^3$ is selected, independently, from hydrogen and $(C_1-C_6)$alkyl, or $R^5$ and $R^6$, or $R^7$ and $R^8$ together with the nitrogen to which they are attached, form a pyrrolidine, piperidine, morpholine, azetidine, piperazine, —N—$(C_1-C_6)$alkylpiperazine or thiomorpholine ring, or a thiomorpholine ring wherein the ring sulfur is replaced with a sulfoxide or sulfone; and each X is, independently, $(C_1-C_6)$alkylene;

with the proviso that: (a) at least one of $R^1$, $R^2$ and $R^3$ must be the other than hydrogen, (b) when $R^2$ and $R^3$ are hydrogen, $R^1$ cannot be methyl or hydrogen; and (c) no fluorine atom in any of the fluoro substituted alkyl or alkoxy moieties of $R^2$ and $R^3$ can be attached to a carbon that is attached to a heteroatom;

and the pharmaceutically acceptable salts of such compounds.

Examples of heteroaryl groups that each of $R^2$ and $R^3$ can be are the following: thienyl, oxazoyl, isoxazolyl, pyridyl, pyrimidyl, thiazolyl, tetrazolyl, isothiazolyl, triazolyl, imidazolyl, tetrazolyl, pyrroyl and the following groups:

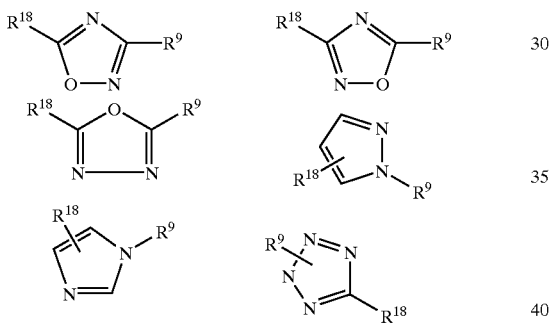

wherein one of $R^9$ and $R^{18}$ is hydrogen or $(C_1-C_6)$alkyl, and the other is a bond to the benzo ring of formula I.

Examples of compounds of this invention are compounds of the formula I, and their pharmaceutically acceptable salts, wherein $R^2$ and $R^3$, together with the benzo ring of formula I, form a bicyclic ring system selected from the following:

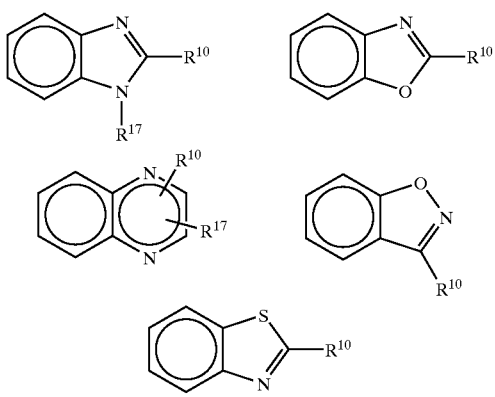

wherein, $R^{10}$ and $R^{17}$ are selected, independenty, from $(C_0-C_6)$ alkoxy-$(C_0-C_6)$alkyl wherein the total number of carbon atoms does not exceed six and wherein any of the alkyl moieties may optionally be substituted with from one to seven fluorine atoms, $(C_1-C_6)$ alkoxy optionally substituted with from one to seven fluorine atoms, nitro, cyano, halo, amino, $(C_1-C_6)$alkylamino, $[(C_1-C_6)alkyl]_2$amino, phenyl and monocyclic heteroaryl wherein said heteroaryl is defined as in the definition of $R^2$ and $R^3$ above;

Other embodiments of this invention relate to compounds of the formula I, and their pharmaceutically acceptable salts, wherein $R^2$ and $R^3$, together with the benzo ring of formula I, form a bicyclic or tricyclic ring system selected from the following:

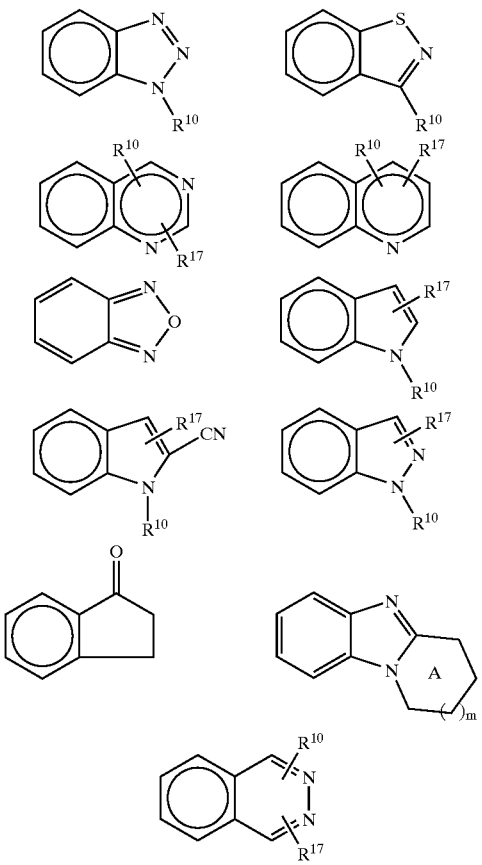

wherein $R^{10}$ and $R^{17}$ are defined as above and m is zero, one or two, and wherein one of the carbon atoms of ring A can optionally be replaced with oxygen or —N$(C_1-C_6)$alkyl.

Other embodiments of this invention relate to compounds of the formula I, and their pharmaceutically acceptable salts, wherein neither $R^2$ nor $R^3$ is attached to the benzo ring of formula I via an oxygen atom.

Other embodiments of this invention relate to compounds of the formula I wherein $R^1$ is not methyl.

Examples of specific compounds of the formula I are the following:

11-Azatricyclo[7.3.1.0$^{2,7}$]trideca-2(7),3,5-triene-5-carbonitrile;

11-Azatricyclo[7.3.1.0$^{2,7}$]trideca-2(7),3,5-triene-4-carbonitrile;

1-[11-Azatricyclo[7.3.1.0$^{2,7}$]trideca-2(7),3,5-trien-5-yl]-1-ethanone;

1-[11-Azatricyclo[7.3.1.0$^{2,7}$]trideca-2(7),3,5-trien-5-yl]-1-propanone;

4-Fluoro-11-azatricyclo[7.3.1.0²,⁷]trideca-2(7),3,5-triene-5-carbonitrile;

5-Fluoro-11-azatricyclo[7.3.1.0²,⁷]trideca-2(7),3,5-triene4-carbonitrile;

1-[11-Azatricyclo[7.3.1.0²,⁷]trideca-2(7),3,5-trien-4-yl]-1-ethanone;

1-[11-Azatricyclo[7.3.1.0²,⁷]trideca-2(7),3,5-trien-4-yl]-1-propanone;

6-Methyl-7-thia-5,14-diazatetracyclol[10.3.1.0²,¹⁰.0⁴,⁸]hexadeca-2(10),3,5,8tetraene;

6-Methy-5,7,14-triazatetracyclo[7.3.1.0²,¹⁰.0⁴,⁸]hexadeca-2(10),3,5,8tetraene;

6,7-Dimethyl-5,7,14-triazatetracyclo[10.3.1.0²,¹⁰.0⁴,⁸]hexadeca-2(10),3,5,8-tetraene;

5,7.14-Triazatetracyclo[10.3.1.0²,¹⁰.0⁴,⁸]hexadeca-2(10),3,5,8-tetraene;

7-Methyl-5,7,14-triazatetracyclo[10.3.1.0²,¹⁰.4,8]hexadeca-2(10),3,5,8tetraene;

5,11,18-Triazapentacyclo[14.3.1.0²,¹⁴.0⁴,¹².0⁶,¹¹]icosa-2(14),3,5,12-tetraene;

7-Ethyl-6-methyl-5,7,14-triazatetracyclo[10.3.1.0²,¹⁰.0⁴,⁸]hexadeca-2(10),3,5,8-tetraene;

6-Methyl-7-propyl-5,7,14-triazatetracyclo[10.3.1.0²,¹⁰.0⁴,⁸]hexadeca-2(10),3,5,8-tetraene;

7-Ethyl-5,7,14-triazatetracyclo[10.3.1.0²,¹⁰.0⁴,⁸]hexadeca-2(10),3,5,8-tetrane;

7-Butyl-6-methyl-5,7,14-triazatetracyclo[10.3.1.0²,¹⁰.0⁴,⁸]hexadeca2(10),3,5,8-tetraene;

7-Isobutyl-6-methyl-5,7,14-triazatetracyclo[10.3.1.0²,¹⁰.0⁴,⁸]hexadeca-2(10),3,5,8-tetraene;

7-Butyl-5,7,14-triazatetracyclo[10.3.1.0²,¹⁰.0⁴,⁸]hexadeca-2(10),3,5,8-tetraene

7-Isobutyl-5,7,14-triazatetracyclo[10.3.1.0²,¹⁰.0⁴,⁸]hexadeca-2(10),3,5,8-tetraene;

5,11,18-Triazapentacyclo[14.3.1.0²,¹⁴.0⁴,¹².0⁵,¹⁰]icosa2(14),3,10,12-tetraene;

5,6-Dimethyl-5,7,14-triazatetracyclo[10.3.1.0²,¹⁰.0⁴,⁸]hexadeca-2(10),3,6,8-tetraene;

5-Ethyl-6-methyl-5,7,14-triazatetracyclo[10.3.1.0²,¹⁰.0⁴,⁸]hexadeca-2(10),3,6,8-tetraene;

5-Methyl-5,7,14-triazatetracyclo[10.3.1.0²,¹⁰.0⁴,⁸]hexadeca-2(10),3,6,8-tetraene;

5-Ethyl-5,7,14-triazatetracyclo[10.3.1.0²,¹⁰.0⁴,⁸]hexadeca-2(10),3,6,8tetraene;

6-Methyl-5-propyl-5,7,14-triazatetracyclo[10.3.1.0²,¹⁰.0⁴,⁸]hexadeca-2(10), 3,6,8-tetraene;

5-Isobutyl-6-methyl-5,7,14-triazatetracyclo[10.3.1.0²,¹⁰.0⁴,⁸]hexadeca-2(10),3,6,8-tetraene;

5-Propyl-5,7,14-triazatetracyclo[10.3.1.0²,¹⁰.0⁴,⁸]hexadeca-2-(10),3,6,8-tetraene;

5-Isobutyl5,7,14-triazatetracyclo[10.3.1.0²,¹⁰.0⁴,⁸]hexadeca-2(10),3,6,8-tetraene;

6-(Trifluoromethyl)-7-thia-5,14-diazatetracyclo[10.3.1.0²,¹⁰.0⁴,⁸]hexadeca-2(10),3,5,8-tetraene;

5,8,15-Triazatetracyclo[11.3.1.0²,¹¹.0⁴,⁹]heptadeca-2(11),3,5,7,9-pentaene;

7-Methyl-5,8,15-triazatetracyclo[11.3.1.0²,¹¹.0⁴,⁹]heptadeca-2(11),3,5,7,9-pentaene;

6-Methyl-5,8,15-triazatetracyclo[11.3.1.0²,¹¹.0⁴,⁹]heptadeca-2(11),3,5,7,9pentaene;

6,7-Dimethyl-5,8,15-triazatetracyclo[11.3.1.0²,¹¹.0⁴,⁹]heptadeca-2(11),3,5,7,9-pentaene;

7-Oxa-5,14-diazatetracyclo[10.3.1.0²,¹⁰.0⁴,⁸]hexadeca-2(10),3,5,8-tetraene;

6-Methyl-7-oxa-5,14-diazatetracyclo[10.3.1.0²,¹⁰.0⁴,⁸]hexadeca-2(10),3,5,8-tetraene;

6-Ethyl-7-oxa-5,14-diazatetracyclo[10.3.1.0²,¹⁰.0⁴,⁸]hexadeca-2(10),3,5,8-tetraene;

6-Propyl-7-oxa-5,14-diazatetracyclo[10.3.1.0²,¹⁰.0⁴,⁸]hexadeca-2(10),3,5,8-tetraene;

5-Methyl-7-oxa-6,14-diazatetracyclo[10.3.1.0²,¹⁰.0⁴,⁸]hexadeca2(10),3,5,8-tetraene;

5-Oxa-7,14-diazatetracyclo[10.3.1.0²,¹⁰.0⁴,⁸]hexadeca-2(10),3,6,8-tetraene;

6-Methyl-5-oxa-7,14-diazatetracyclo[10.3.1.0²,¹⁰.0⁴,⁸]hexadeca-2(10),3,6,8-tetrane;

6-Ethyl-5-oxa-7,14-diazatetracyclo[10.3.1.0²,¹⁰.0⁴,⁸]hexadeca-2(10),3,6,8tetraene;

6-Propyl-5oxa-7,14-diazatetracyclo[10.3.1.0²,¹⁰.0⁴,⁸]hexadeca-2(10),3,6,8-tetraene;

7-Methyl-5oxa-6,14-diazatetracyclo[10.3.1.0²,¹⁰.0⁴,⁸]hexadeca-2(10),3,6,8tetraene;

4,5-Difluoro-11-azatricyclo[7.3.10²,⁷]trideca-2(7),3,5-triene4-chloro-5-fluoro-11-azatricyclo[7.3.1.0²,⁷]trideca-2(7),3,5-triene;

5-Chloro-4-fluoro-11-azatricyclo[7.3.1.0²,⁷]trideca-2(7),3,5-triene;

4-(1-Ethynyl)-5-fluoro-11-azatricyclo[7.3.1.0²,⁷]trideca-2(7),3,5-triene;

5-(1-Ethynyl)-4-fluoro-11-azatricyrdo[7.3.1.0²,⁷]trideca-2(7),3,5-triene; and 4,5-Dichloro-11-azatricyclo[7.3.1.0²,⁷]trideca-2(7),3,5-triene.

This invention also relates to compounds of the formula

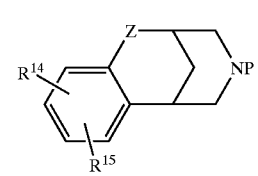

(I')

wherein Z is $CH_2$, C(=O) or $CF_2$; P is hydrogen, methyl, $COOR^{16}$ wherein $R^{16}$ is allyl, 2,2,2-trichloroethyl or ($C_1$–$C_6$)alkyl; —C(=O)$NR^5R^6$ wherein $R^5$ and $R^6$ are defined as in formula I above; —C(=O)H, —C(=O)($C_1$–$C_6$)alkyl wherein the alkyl moiety may optionally be substituted with from 1 to 3 halo atoms, preferably with from 1 to 3 fluoro or chloro atoms; benzyl or t-butoxycarbonyl (t-Boc); and $R^{14}$ and $R^{15}$ are selected, independently, from hydrogen, hydroxy, nitro, amino, —O($C_1$–$C_6$)alkyl or halo; with the proviso that $R^{14}$ and $R^{15}$ can not both be hydrogen when P is hydrogen or methyl. Such compounds are useful as intermediates in the synthesis of compounds of the formula I.

Unless otherwise indicated, the term "halo", as used herein, includes fluoro, chloro, bromo and iodo.

Unless otherwise indicated, the term "alkyl", as used herein, includes straight, branched or cyclic, and may include straight and cyclic alkyl moieties as well as branched and cyclic moieties.

The term "alkoxy", as used herein, means "alkyl-O—", wherein "alkyl" is defined as above.

The term "alkylene, as used herein, means an alkyl radical having two available bonding sites (ie., -alkyl-), wherein "alkyl" is defined as above.

Unless otherwise indicated, the term "one or more substituents", as used herein, refers to from one to the maximum number of substituents possible based on the number of available bonding sites.

The term "treatment", as used herein, refers to reversing, alleviating, inhibiting the progress of, or preventing the disorder or condition to which such term applies, or one or more symptoms of such condition or disorder. The term "treatment", as used herein, refers to the act of treating, as "treating" is defined immediately above.

The compounds of formula I may have optical centers and therefore may occur in different enantiomeric configurations. The invention includes all enantiomers, diastereomers, and other stereoisomers of such compounds of formula I, as well as racemic and other mixtures thereof.

The present invention also, relates to all radiolabeled forms of the compounds of the formula I. Preferred radiolabeled compounds of formula I are those wherein the radiolabels are selected from as $^3H$, $^{11}C$, $^{14}C$, $^{18}F$, $^{123}I$ and $^{125}I$. Such radiolabeles compounds are useful as research and diagnostic tools in metabolism pharmacokinetics studies and in binding assays in both animals and man.

The present invention also relates to a pharmaceutical composition for use in reducing nicotine addiction or aiding in the cessation or lessening of tobacco use in a mammal, including a human, comprising an amount of a compound of the formula I, or a pharmaceutically acceptable salt thereof, that is effective in reducing nicotine addiction or aiding in the cessation or lessening of tobacco use and a pharmaceutically acceptable carrier.

The present invention also relates to a method for reducing nicotine addiction or aiding in the cessation or lessening of tobacco use in a mammal, including a human, comprising administering to said mammal an amount of a compound of the formula I, or a pharmaceutically acceptable salt thereof, that is effective in reducing nicotine addiction or aiding in the cessation or lessening of tobacco use.

The present invention also relates to a method of treating a disorder or condition selected from inflammatory bowel disease (including but not limited to ulcerative colitis, pyoderma gangrenosum and Crohn's disease), irritable bowel syndrome, spastic dystonia, chronic pain, acute pain, celiac sprue, pouchitis, vasoconstriction, anxiety, panic disorder, depression, bipolar disorder, autism, sleep disorders, jet lag, amyotrophic lateral sclerosis (ALS), cognitive dysfunction, hypertension, bulimia, anorexia, obesity, cardiac arrhythmias, gastric acid hypersecretion, ulcers, pheochromocytoma, progressive supranuclear palsy, chemical dependencies and addictions (e.g., dependencies on, or addictions to nicotine (and/or tobacco products), alcohol, benzodiazepines, barbiturates, opioids or cocaine), headache, stroke, traumatic brain injury (TBI), obsessive-compulsive disorder (OCD), psychosis, Huntington's Chorea, tardive dyskinesia, hyperkinesia, dyslexia, schizophrenia, multi-infarct dementia, age related cognitive decline, epilepsy, including petit mal absence epilepsy, senile dementia of the Alzheimer's type (AD), Parkinson's disease (PD), attention deficit hyperactivity disorder (ADHD) and Tourette's Syndrome in a mammal, comprising administering to a mammal in need of such treatment an amount of a compound of the formula I, or a pharmaceutically acceptable salt thereof, that is effective in treating such disorder or condition.

The present invention also relates to a pharmaceutical composition for treating a disorder or condition selected from inflammatory bowel disease (including but not limited to ulcerative colitis, pyoderma gangrenosum and Crohn's disease), irritable bowel syndrome, spastic dystonia, chronic pain, acute pain, celiac sprue, pouchitis, vasoconstriction, anxiety, panic disorder, depression, bipolar disorder, autism, sleep disorders, jet lag, amyotrophic lateral sclerosis (ALS), cognitive dysfunction, hypertension, bulimia, anorexia, obesity, cardiac arrhythmias, gastric acid hypersecretion, ulcers, pheochromocytoma, progressive supranuclear palsy, chemical dependencies and addictions (e.g., dependencies on, or addictions to nicotine (and/or tobacco products), alcohol, benzodiazepines, barbiturates, opioids or cocaine), headache, stroke, traumatic brain injury (TBI), obsessive-compulsive disorder (OCD), psychosis, Huntington's Chorea, tardive dyskinesia, hyperkinesia, dyslexia, schizophrenia, multi-infarct dementia, age related cognitive decline, epilepsy, including petit mal absence epilepsy, senile dementia of the Alzheimer's type (AD), Parkinson's disease (PD), attention deficit hyperactivity disorder (ADHD) and Tourette's Syndrome in a mammal, comprising an amount of a compound of the formula I, or a pharmaceutically acceptable salt thereof, and a pharmaceutically acceptable carrier.

This invention also relates to the pharmaceutically acceptable acid addition salts of the compounds of formula I. Examples of pharmaceutically acceptable acid addition salts of the compounds of formula I are the salts of hydrochloric acid, p-toluenesulfonic acid, fumaric acid, citric acid, succinic acid, salicylic acid, oxalic acid, hydrobromic acid, phosphoric acid, methanesulfonic acid, tartaric acid, malate, di-p-toluoyl tartaric acid, and mandelic acid.

DETAILED DESCRIPTION OF THE INVENTION

Except where otherwise stated, $R^1$ through $R^{18}$, m and P, and structural formula I in the reaction schemes and discussion that follow are defined as above.

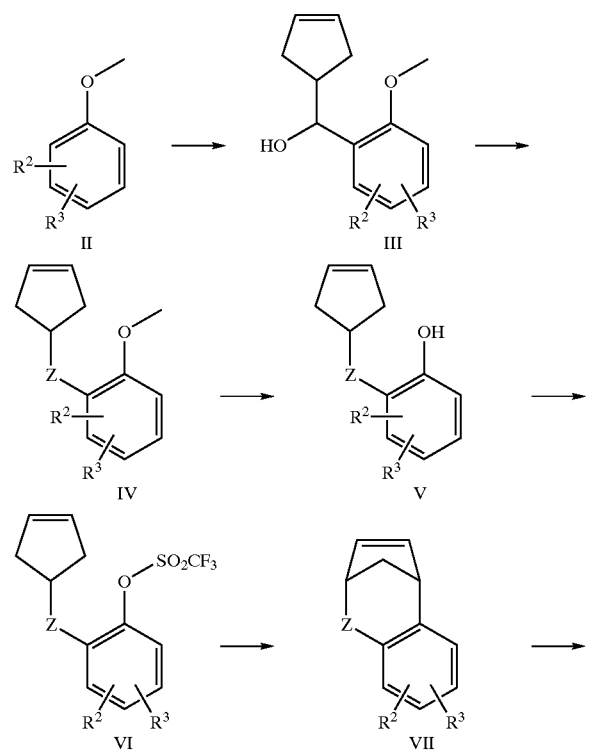

SCHEME 1

US 6,462,035 B1
-continued
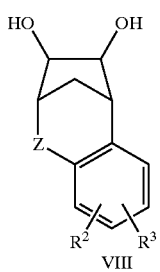
VIII
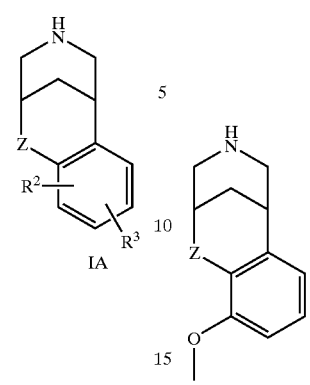
IA
IB
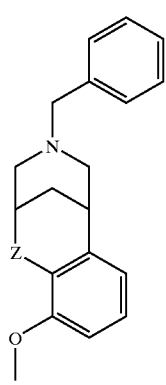
XVII
SCHEME 2
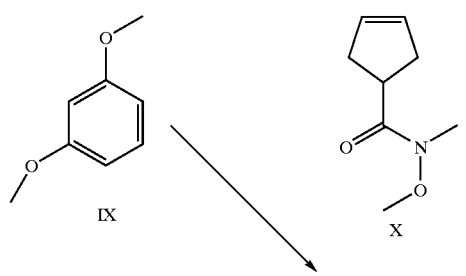
IX    X
IB
XVII
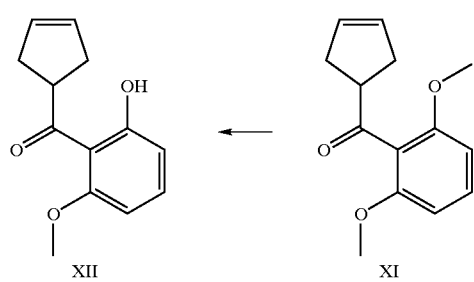
XII    XI
SCHEME 3
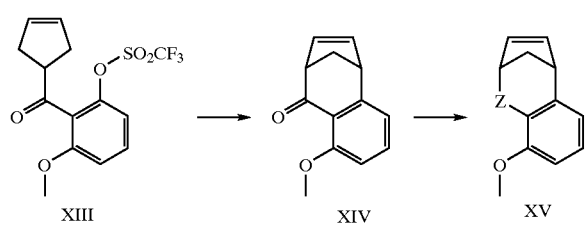
XIII    XIV    XV
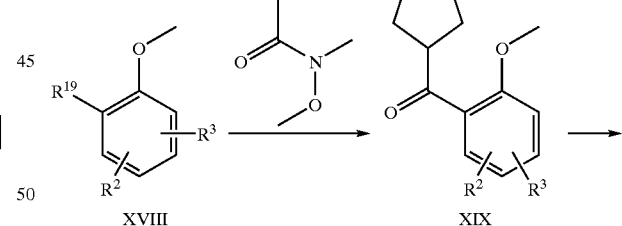
XVIII    XIX
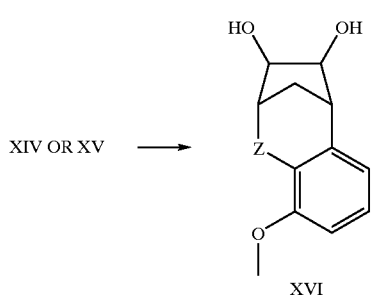
XIV OR XV    XVI
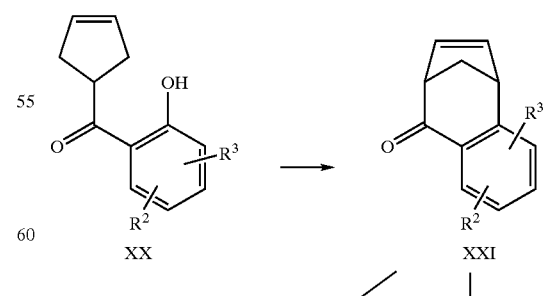
XX    XXI

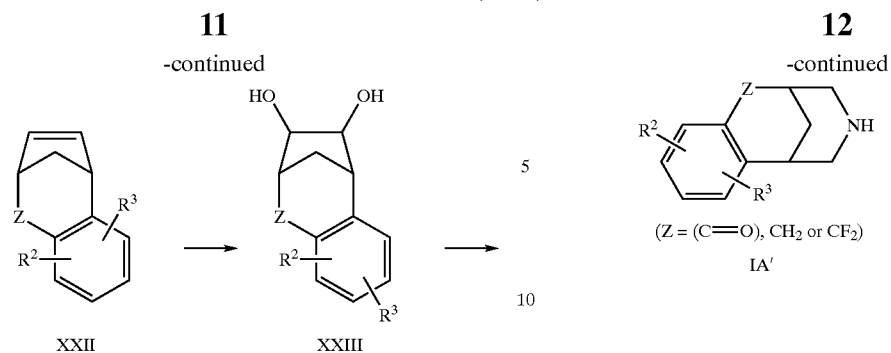
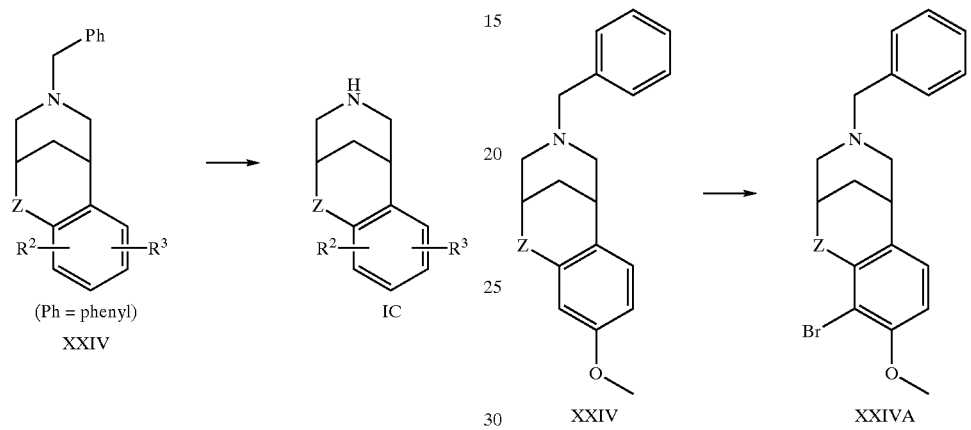
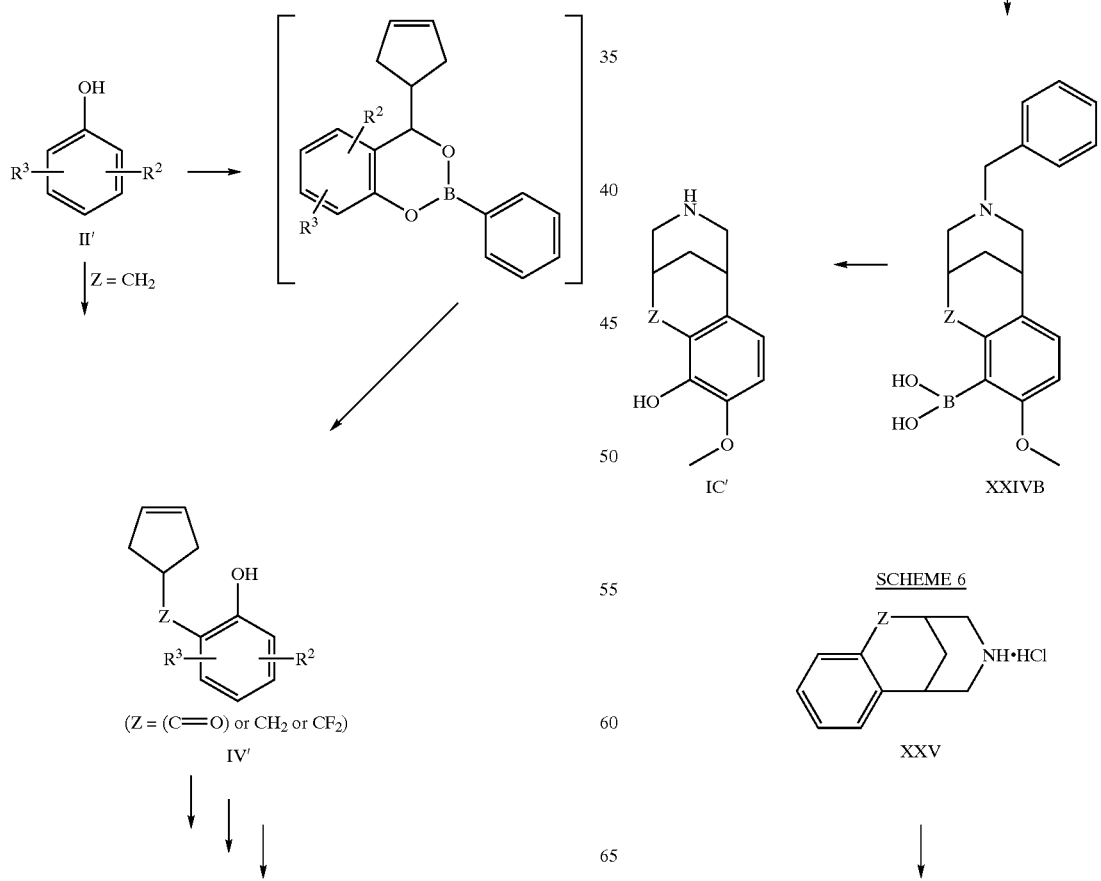
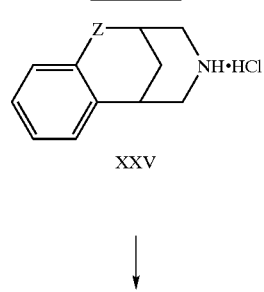

-continued
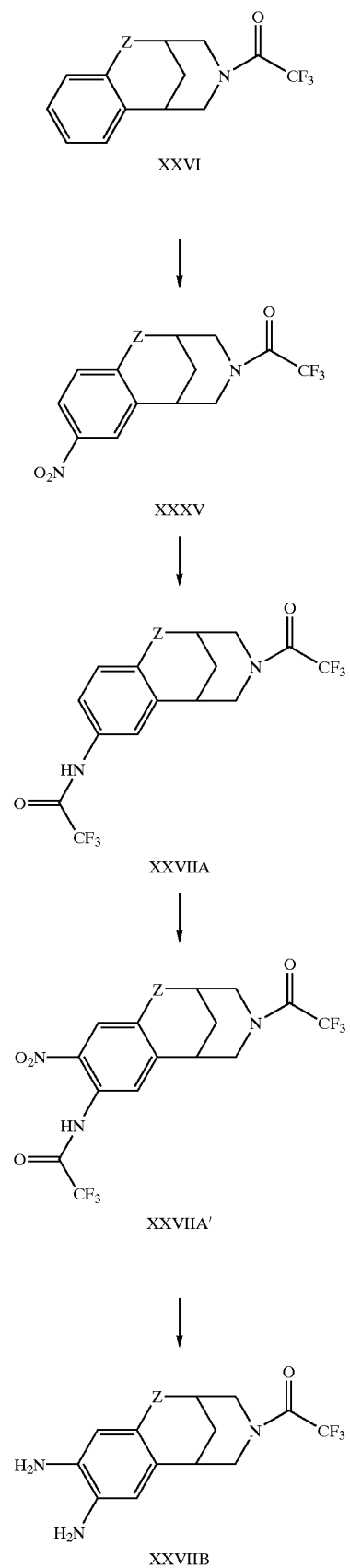
SCHEME 7
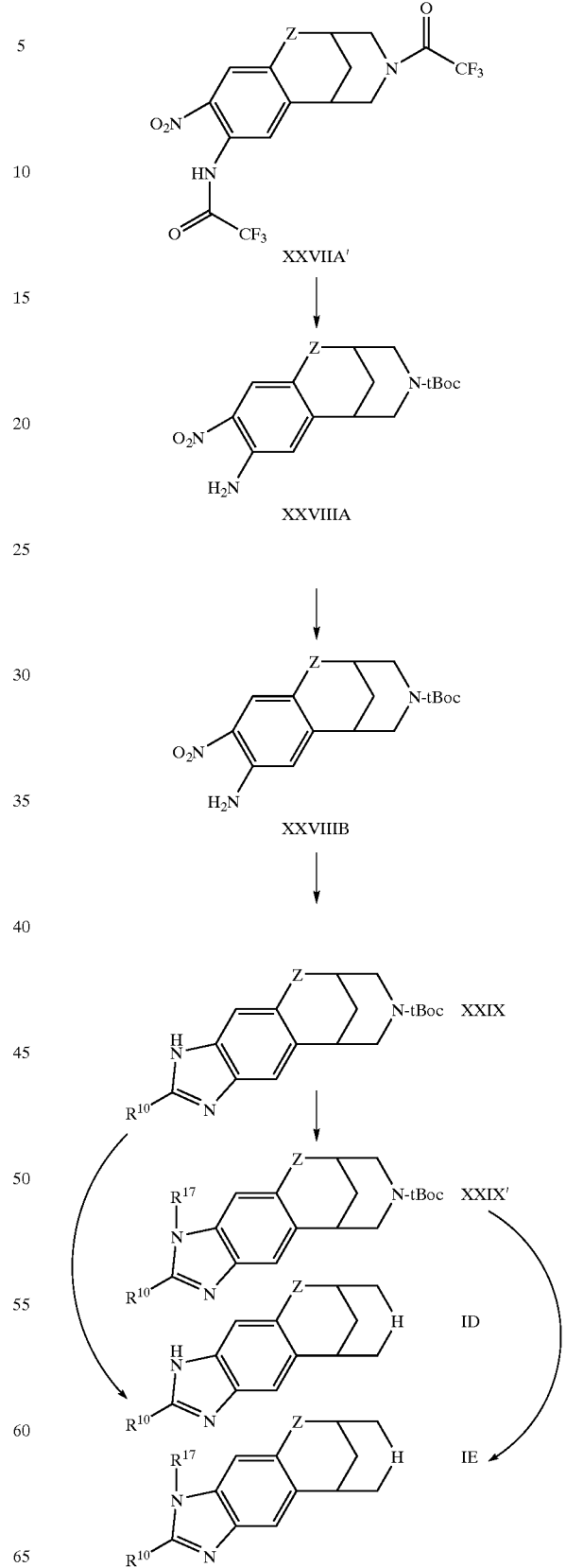

SCHEME 8A
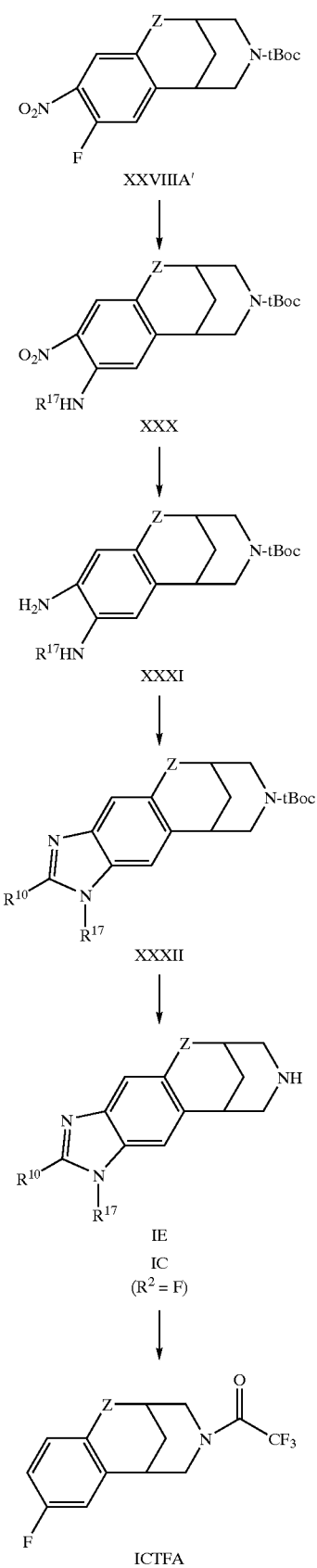
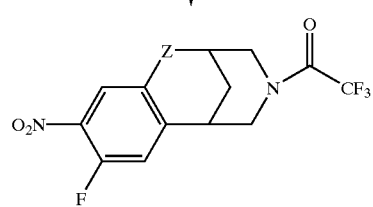
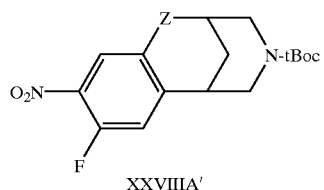
SCHEME 9
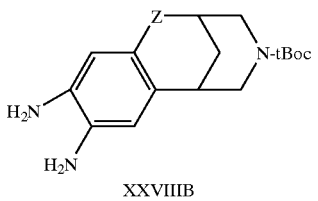
SCHEME 10
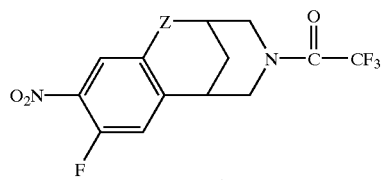
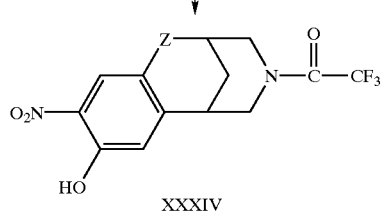

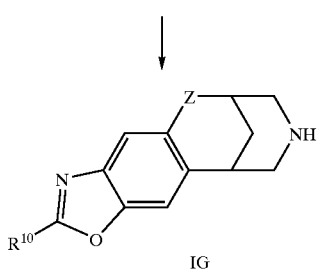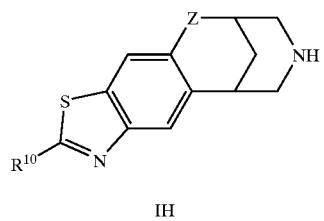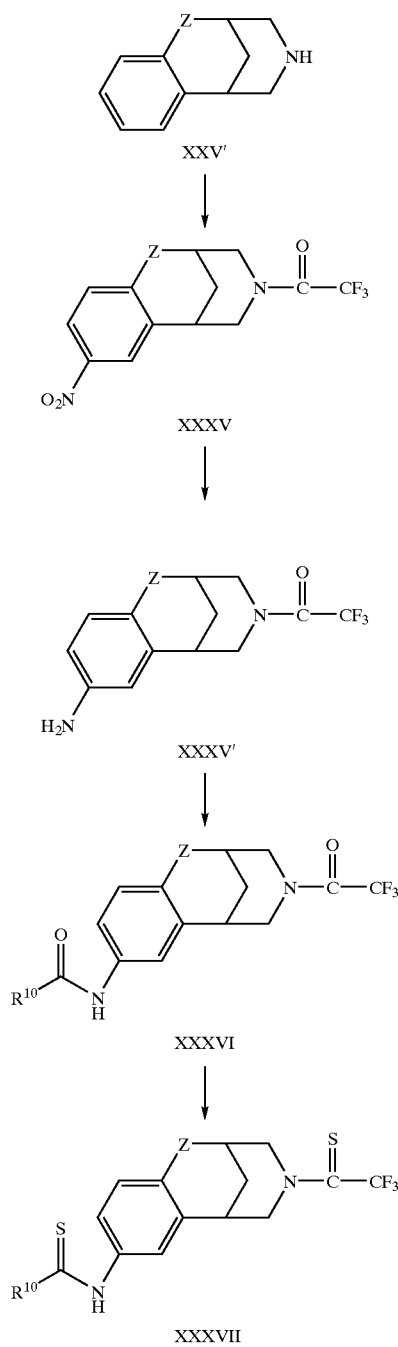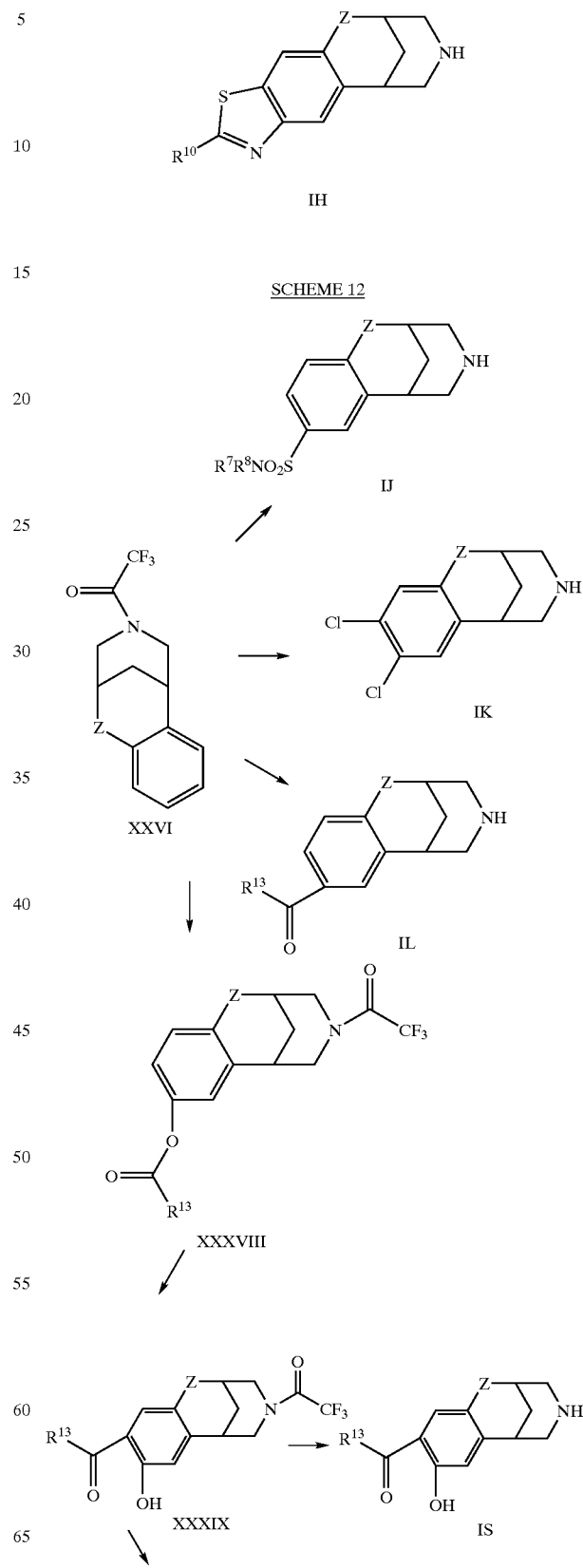

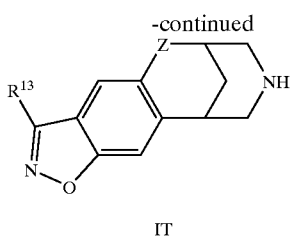

IT

SCHEME 13

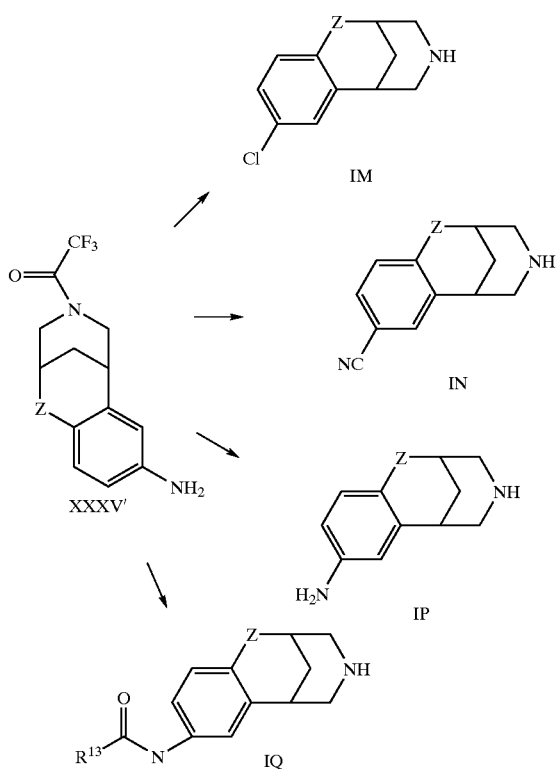

Scheme 1–13 illustrate methods of synthesizing compounds of the formula I. Schemes 1–4 illustrate such methods wherein the substituent groups $R^2$ and $R^3$ are attached prior to cyclization to form the tricyclic nucleus of formula I, which is represented by the free base of structural formula IA (Scheme 1) or IC (Scheme 3) wherein $R^2$ and $R^3$ are hydrogen. Schemes 5–13 illustrate methods of forming compounds of the formula I from starting materials that contain such nucleus.

Referring to Scheme 1, the starting material of formula II is converted to a compound of formula III by the following process. The starting material of formula II is reacted with approximately 1 equivalent of a strong base such as n-butyllithium in a solvent such as anhydrous THF, ether or methyl t-butyl ether, at a temperature from about −78° C. to about −65° C. This metalation occurs over a period of from about ten minutes to five hours, typically in about two hours with the temperature maintained below −65° C. The anion, so-produced, is then treated with cyclopent-3-ene carboxaldehyde in the same solvent at such a rate so as to maintain the temperature below −65° C. The reaction is then quenched by addition of the reaction mixture to an aqueous acidic medium and worked up.

The compound of formula III, so-produced, is then reduced at the benzylic position by the action of trifluoro-acetic acid and a reducing agent such as triethylsilane, to form the corresponding compound having formula IV. This reaction is generally conducted in a chlorinated hydrocarbon solvent, such as chloroform, dichloroethane, (DCE) or methylene chloride, at about room temperature, for a period of about 6 to 24 hours, preferably for about 18 hours.

This compound of formula IV is then converted into the corresponding compound of formula V by treating it with equivalent amounts of tetrabutyl ammonium iodide and boron trichloride in a chlorinated hydrocarbon solvent, such as chloroform, dichloroethane (DCE) or methylene chloride. This reaction is typically conducted at a temperature of −78° C. initially, and then allowed to react over a period of about two hours while warming to ambient temperature.

The resulting compound of formula V is then reacted with trifluoromethanesulfonic anhydride in a chlorinated hydrocarbon solvent, such as chloroform, dichloroethane (DCE) or methylene chloride, in the presence of a base such as pyridine or 3-methylpyridine, to form the corresponding trifluoromethanesulfonic acid ester of formula VI. Typically, the initial reaction temperature is about −78° C. and the reaction is allowed to warm to room temperature to complete the reaction.

The trifluoromethanesulfonic acid ester of formula VI is then reacted under Heck cyclization conditions to produce the corresponding compound of formula VII. This reaction may be performed with or without a solvent. Suitable solvents include N,N-dimethylformamide (DMF), N-methylpyrrolidone (NMP) and toluene. Temperatures ranging from about 60° C. to about 130° C. are suitable, and the reaction is generally run for a period of about 1 to 48 hours. Preferably, the reaction is conducted at a temperature of about 100° C. for about 2–18 hours. Catalysts in this reaction are generated in situ by treatment with sources of palladium, such as palladium acetate ($Pd(OAc)_2$), palladium dichloride ($PdCl_2$) or palladium in the reduced zero oxidation state such as palladium on carbon (Pd/C) or tris (dibenzylidene acetone)dipalladium(O) ($Pd_2(dba)_3$). Analogous nickel catalysts can also be used. The amount of catalyst required is about 0.1 mole % to a stoichiometric amount. Preferably, about 2–10 mole % of the palladium or nickel catalyst is used. Often, conditions used in these reactions include ligands such as triphenylphosphine or tri-o-tolylphosphine, or bidentate ligands such as DPPF, DPPE, DPPB, DPPP (DPP=bis-diphenylphosphine, F=ferrocene, E=ethyl, P=propane, B=butane) or any of a variety of chiral ligands such as BINAP (2,2'-bis (diphenylphosphino)-1,1'-binaphthyl) or arsenate ligands, or bidentate combinations of these ligands with chiral directing groups, such as, for example, oxazolines, though the inclusion of ligands may not be necessary in all cases. If ligands are used in combination with palladium or nickel sources, they are typically used in amounts from about 0.5 to about 4 molar equivalents of the palladium or nickel catalyst.

The above reaction is conducted in the presence of a base, typically a tertiary amine base such as triethylamine or diisopropylethylamine. Other bases such as carbonates or acetates, (e.g., potassium carbonate, sodium carbonate, sodium acetate or potassium acetate) may also provide adequate or desirable results. In some cases, as exemplified in the experimental examples, it is beneficial to use a tertiary amine base, as described above, in combination with catalytic acetate or carbonate salt such as potassium acetate, in an amount equivalent to the phosphine ligand to accelerate the reaction. An additional additive that may be useful is an alkyl ammonium halide salt, such as tetrabutyl ammonium chloride. These conditions are common, and are based on the conditions described by Jeffrey T. in *J. Chem. Soc., Chem. Commun.,* 1984, 1287 and *Synthesis,* 1987, 70. These reactions are generally performed under an atmosphere of nitrogen or argon, but may or may not require the presence of oxygen.

Reaction of the compound of formula VII with osmium tetroxide and a reoxidant such as N-methylmorpholine-N-oxide (NMO) in acetone and water at about room temperature yields the corresponding compound of formula VIII.

The compound having formula VIII is then converted into the desired corresponding compound of formula IA using the following procedure. First, the compound of formula VIII is reacted with sodium periodate in a mixture of a chlorinated hydrocarbon, preferably dichloroethane (DCE), and water, or with lead tetraacetate in a chlorinated hydrocarbon solvent, at a temperature from about 0° C. to about room temperature, to generate a dialdehyde or glycal intermediate. The product of this reaction is then reacted, with benzylamine (or ammonia) and sodium triacetoxyborohydride. Removal of the N-benzyl group yields the desired compound of formula IA. Removal of the benzyl group can be accomplished using methods well known to those of skill in the art, for example, by first optionally reacting the free base with one equivalent of acid, e.g., hydrochloric acid (to form the corresponding acid addition salt), and then with hydrogen and palladium hydroxide in methanol at about room temperature.

Alternatively, the reductive amination may be carried out in situ as follows. Oxidative cleavage of the diol of formula VIII performed using sodium periodate in aqueous THF or alcohol to form the dialdehyde/glycal intermediate referred to above. Treatment of this intermediate with excess benzylamine (or ammonia), palladium hydroxide and hydrogen at a temperature from about room temperature to about 70° C. generates the desired compound of formula IA.

If the above method used leaves a benzyl group on the compound, removal of the benzyl group will yield the desired compound of formula IA. Removal of the benzyl group can be accomplished using methods well known to those of skill in the art, for example, optionally reacting the free base with one equivalent of acid, e.g., hydrochloric acid (to form the corresponding acid addition salt), followed by hydrogen and palladium hydroxide in methanol at about room temperature.

In the reductive animation step described above and throughout this document, alternatives to benzyl amine, such as ammonia, hydroxylamine, alkoxy amines, methyl amine, allyl amine, and substituted benzyl amines (e.g., diphenylmethyl amine and 2- and 4-alkoxy substituted benzyl amines) can also be used. They can be used as free bases, or as their salts, preferably their acetate salts, and can be subsequently removed by methods described for each by T. W. Greene and G. M. Wuts, "Protective Groups in Organic Synthesis", 1991, John Wiley & Sons, New York, N.Y.

The procedure described above and illustrated in Scheme 1 is preferred for making compounds of the formula I wherein $R^2$ or $R^3$ is susceptible to reacting to form an aryne or in another type of side reaction.

The procedure described above produces compounds of the formula IA wherein Z is $CH_2$. Compounds of the formula IA wherein Z is (C=O) can be formed using the procedure illustrated in Scheme 1, as described above, with the exception that the compound of formula III is oxidized, rather than reduced, at the benzylic position, to form a compound of the formula IV wherein Z is (C=O). This can be accomplished using methods well known to those of skill in the art such as by treatment with Jones reagent (chromic acid solution) in ether or acetone at a temperature from about 0° C. to about room temperature. Compounds of the formula IA wherein Z is $CF_2$ can be prepared in a similar manner by converting the oxidized compound of formula IV wherein Z is (C=O) into the corresponding compound of formula IV wherein Z is $CF_2$, and then continuing with the reaction sequence of Scheme 1. This conversion can be accomplished using methods well known in the art, such as by treatment with Lawesson's reagent. The reaction with Lawesson's reagent is generally carried out in a reaction inert solvent such as benzene or toluene, preferably toluene, at a temperature from about room temperature to about the reflux temperature of the reaction mixture, preferably at about the reflux temperature.

Scheme 2 illustrates an alternate method of preparing compounds of the formula I. This method is the preferred method for preparing such compounds wherein neither $R^2$ nor $R^3$ is susceptible to reacting in an undesireable side reaction. Referring to Scheme 2, the compound of formula IX is treated with a strong base such as n-butyllithium at a temperature from about room temperature to about the reflux temperature of the reaction mixture, in a solvent such as ether or t-butyl methyl ether. This metalation occurs over a period of from about 1 to 5 hours, typically in about 4 hours when the reaction is conducted at the reflux temperature in ether. The resulting anion is then cooled in the same solvent or in a solvent mixture such as one containing tetrahydrofuran (THF), to a temperature of about −78° C. This anion can then be reacted with cyclopent-3-enecarboxylic acid methoxy-methylamide Q(X) at about −78° C., for about a half hour, with completion of the reaction occurring upon warming to ambient temperature. This reaction yields the compound of formula XI. The compound of formula XI is then dissolved in a solvent such as methylene chloride and treated with boron trichloride at about −78° C. After a period of 20 about minutes, the reaction is allowed to warm to about 0° C. and is worked up. The resulting phenol of formula XII is then converted into the trifluoromethanesulfonic ester by the methods described above for generating the compound of formula XIII. The resulting ester can then be converted into a compound of formula XIV under Heck conditions, as described above.

Reduction of the compound of formula XIV using standard Wolff-Kishner conditions yields the compound of formula XV. These conditions are well known to those skilled in the art, and include reacting the compound of formula XIV with hydrazine and potassium hydroxide, first at a temperature of approximately 100° C. in a solvent, usually ethylene glycol or diglyme, and then increasing the temperature to about 180–200° C. Reductions that are known in the art to be equivalent to the standard Wolff-Kishner reduction may also be used. The compound of formula XV can be converted into the compound of formula IB by a procedure analogous to the conversion of compounds of the formula VII into those of the formula IA in Scheme 1.

Rather than reducing the ketone in the compound of formula XIV, the corresponding compound wherein the oxo group is replaced by $CF_2$ can be formed by treatment with Lawesson's reagent, or using other methods for effecting this conversion that are well known to those of skill in the art.

Methyl ethers may be converted to their corresponding phenols by methods well known to those skilled in the art. This can be accomplished by exposing the compound of formula IB or XVII to hydrobromic acid and warming the resulting mixture to the reflux temperature for a period of about 1 hour. This reaction produces the corresponding phenol of formula IB' or XVIII, respectively.

An alternative to the methods described in Schemes 1 and 2 for generating aryl anions is to use halogen-metal exchange conditions. For example, a compound of the formula XVIII, illustrated in Scheme 3, wherein $R^{19}$ is bromo or iodo, can be treated with an alkyllithium base such as n-butyllithium, at a temperature form about −78° C. to 20° C., typically at about −78° C. to produce an aryl anion of the formula

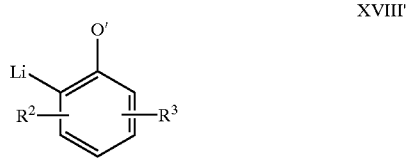

XVIII'

The anion produced in this reaction can then be reacted with an aldehyde, such as described in Scheme 1, or an appropriate disubstituted amide, as described in Scheme 2, to produce a compound of the formula XIX. (Rather than reacting the compound of formula XVIII with an alkyllithium base, as described immediately above, such compound can optionally first be converted into a Grignard reagent ($R^{19} \rightarrow \rightarrow MgR^{19}$) using standard methods, and then reacted as described above for compounds of the formula XVIII' to prepare a compound of the formula XIX).

The resulting compound of formula XIX can then be converted into a compound of the formula IC (Scheme 3) using the methods described above for the conversion of compounds of the formula XI into those of the formula IB (Scheme 2) and for the conversion of compounds of the formula IV into those of the formula IA (Scheme 1).

The generation of anions at the ortho position of the aromatic systems employed in the synthetic procedures described in this application is encompassed under a general synthetic strategy known to those skilled in the art as Directed Ortho Metalation (DOM). Within this area, a number of functional groups known as Directed Metalation Groups (DMGs) have been studied for this purpose, and some are reviewed in Snieckus, V. *Chem Rev.* 1990, 879. Where applicable, DMGs other than those utilized in this work may be equally applicable to the preparation of the compounds and intermediates described herein.

An alternative method for the generation of compounds similar to compounds of the formula V, XII or XX appears in Scheme 4. In this method, cyclopent-3-ene carboxaldehyde and a phenol are combined with an aryl boronic acid and an acid catalyst such as an acetic acid (optionally substituted with halo substituents at the alpha position to modulate the acidity of the reaction), or with a aryl boron dihalide, which, by its nature, will generate a mineral acid under the conditions of the reaction, in a solvent such as benzene, toluene, dioxane or dichloromethane, preferably in benzene. The temperature of the reaction is typically the reflux temperature, or at a temperature that allows any of the standard methods for removal of water generated in the reaction to be removed at a rate that allows the desired reaction to occur. A convenient method employs a Dean-Stark trap to remove water formed in the reaction. Typically, the reaction is conducted for a period of 3–48 hours, generally 10–24 hours, or until the theoretical amount of water has been collected. At this time the reaction is freed of solvent and then subjected to conditions as described above for reduction of benzylic hydroxyl groups or ethers, for example, treatment of this intermediate with trifluoroacetic acid and a reducing agent such as triethylsilane. This reaction is conducted in a chlorinated hydrocarbon solvent, such as chloroform, dichloroethane (DCE) or methylene chloride, at or about room temperature for a period of 6 to 24 hours, preferably 18 hours.

The above reaction produces a compound of the formula IV' wherein Z is $CH_2$. The corresponding compounds of the formula IV' wherein Z is (C=O) and $CF_2$ can be formed using the methods described above for preparing compounds of the formula IV (Scheme 1) wherein Z is (C=O) or $CF_2$.

The resulting compounds of formula IV' (Z is (C=O), $CH_2$ or $CF_2$) are is then converted into the corresponding compound of formula IA' using the methods described above and depicted in Scheme 1 for the preparation of compounds of the formula IA.

Scheme 5 illustrates a method for the introduction of substituents, such as bromine and oxygen, into compounds of the invention. Treatment of a compound of formula XXIV with bromine, under standard conditions known to those of skill in the art, for example, in a chlorinated hydrocarbon solvent such as chloroform, dichloroethane (DCE) or methylene chloride, at a temperature of about 0° C. to about room temperature, preferably at room temperature, in the presence of a base such as sodium acetate, generates the corresponding compound of formula XXIVA. The bromide so produced (XXIVA) can then be converted, by the process of halogen-metal exchange described above, to a lithium anion derivative, which can then be treated with a variety of electrophiles, for example, trialkylborates, typically at temperatures ranging between −78 and 0° C. to produce the corresponding boronic acid derivative of formula XXIVB.

This compound can then be converted to a variety of derivatives accessible through Suzuki coupling chemistry under standard conditions known to those of skill in the art. Alternatively these boronic acid compounds may be converted into the corresponding phenol derivatives, by reaction with hydrogen peroxide or N-methylmorpholine, in a solvent such as THF, or by any other standard methods known to those of skill in the art. Removal of the benzyl protecting group by methods described above yields the desired compound of formula IC'.

Phenols prepared as described above and in the experimental section can be converted to the corresponding trifluommethanesulfonic esters. These derivatives, as well as the bromides formula XXIVA, can be used to access a variety of other substituents (i.e., other values of $R^2$ and $R^3$) such as aryl, acetylene and vinyl substituents, as well as the corresponding carbonyl esters and amides, by palladium and nickel catalyzed processes known to those of skill in the art, such as Heck, Suzuki and Stille couplings and Heck carbonylations. Additionally, phenols can be alkylated by a variety of common methods to prepare ethers. Additionally, esters may be treated with nucleophiles, such as Grignard reagents to prepare the corresponding tertiary alcohols. Examples of these transformations appear in the Experimental Examples.

Scheme 6 illustrates the preparation of certain intermediates used in the procedure of Scheme 7. Referring to Scheme 6, the starting material of formula XXV is reacted with trifluomacetic anhydride, in the presence of pyridine, to form the compound of formula XXVI. This reaction is typically conducted in methylene chloride at a temperature from about 0° C. to about room temperature.

The compound of formula XXVI, when Z is not (C=O), can then be converted into the nitro derivative of formula XXXV by the following process. The compound of the formula XXVI is added to a mixture of 2 or more equivalents of trifuommethanesulfonic acid ($CF_3SO_2OH$) and 1 to 1,5 equivalents of nitric acid, in a chlorinated hydrocarbon solvent such as chloroform, dichloroethane (DCE) or methylene chloride. The resulting mixture is allowed to react for about 5 to 24 hours. Both of the foregoing reactions are generally conducted at a temperature ranging from about −78° C. to about 0° C. for about 2 hours, and then allowed to warm to room temperature for the remaining time.

Compounds of the formula XXXV wherein Z is (C=O) can be prepared by oxidizing the analogous compounds wherein Z is $CH_2$ as described by Kapur et al., *Can. J. Chem.*, 68, 1988, 2888–2893.

Reduction of the compound of formula XXXV, using methods well known to those of skill in the art, yields the corresponding aniline. This reduction can be accomplished, for example, using hydrogen and a palladium catalyst such as palladium hydroxide, and running the reaction in methanol or ethanol at about room temperature. The intermediate aniline is then converted into the trifluoroacetamide of formula XXVIIA as described above for the preparation of compounds of the formula XXVI.

Mononitration of the compound of formula XXVIIA, as described above for the preparation of compounds of the formula XXXV, yields the corresponding nitro derivative of formula XXVIIA'. Treatment of the nitro derivative of formula XXVIIA' with aqueous bicarbonate in methanol or THF, at a temperature from about 20° C. to about 70° C., followed by reduction of the nitro group as described above, yields the corresponding compound of formula XXVIIB.

Referring to Scheme 7, the compound of formula XXVIIA' is converted into the corresponding compound wherein the trifluoroacetyl protecting group is replaced by a t-Boc protecting group XXXVIIIA by reacting it first with an alkali metal or alkaline earth metal (or ammonium) hydroxide or carbonate, and then reacting the isolated product from the foregoing reaction with di-t-butyldicarbonate. The reaction with the alkali or alkaline earth metal (or ammonium) hydroxide or carbonate is generally carried out in an aqueous alcohol, dioxane or tetrahydrofuran (THF) at a temperature from about room temperature to about 70° C., preferably at about 70° C., for about one to about 24 hours. The reaction of the isolated, unprotected amine or an acid addition salt of such amine, from the above reaction with dit-butyldicarbonate is preferably carried out in a solvent such as THF, dioxane or methylene chloride at a temperature from about 0° C. to about room temperature. This reaction may or may not be conducted in the presence of a base. When the reactant is a salt of the amine, use of a base is preferred. The resulting compound of formula XXVIIIA can be converted into the corresponding diamino derivative of formula XXVIIIB using the procedure described above for converting compounds of the formula XXVIIA' into the co responding diamino compounds of formula XXVIIB.

The conversion of the compound of formula XOCVIIIB into the desired compound of the formula XXIX can be accomplished by reacting the compound of formula XXVIIIB with a compound of the formula

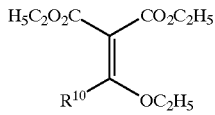

wherein $R^{10}$ is hydrogen, $(C_1-C_6)$alkyl optionally substituted with from one to seven fluorine atoms, aryl-$(C_0-C_3)$ alkyl wherein said aryl is selected from phenyl and naphthyl, or heteroaryt-$(C_0-C_3)$alkyl wherein said heteroaryl is selected from five to seven membered aromatic rings containing from one to four heteroatoms selected from oxygen, nitrogen and sulfur, and wherein each of the foregoing aryl and heteroryl groups may optionally be substituted with one or more substituents, preferably from zero to two substituents, independently selected from $(C_1-C_6)$alkyl optionally substituted with from one to seven fluorine atoms, $(C_1-C_6)$ alkoxy optionally substituted with from one to seven fluorine atoms and cyano. The preferred solvent for this reaction is a 10:1 mixture of ethanol:acetic acid. The reaction temperature can range from about 40° C. to about 100° C. It is preferably about 60° C. Other appropriate solvents include acetic acid, ethanol and isopropanol.

Alternate methods of preparing compounds of the formula XXIX from the compound of formula XXVIIIB are described by Segelstein et al., *Tetrahedron Lett.*, 1993, 34, 1897.

Removal of the t-Boc protecting group from the compound of formula XXIX yields the corresponding compound of formula ID. The protecting group can be removed using methods well known to those of skill in the art. For example, the compound of formula XXIX can be treated with an anhydrous acid such as hydrochloric acid, hydrobromic add, methanesulfonic acid, or trifluoroacetic acid, preferably hydrochloric acid in ethyl acetate, at a temperature from about 0° C. to about 100° C., preferably from about room temperature to about 70° C., for about one to 24 hours.

The compound of formula XXIX can be converted into the corresponding compound of formula IE by reacting it with a compound of the formula $R^{17}Z$, wherein $R^{17}$ is defined as $R^{10}$ is defined above, and Z is a leaving group such as a halo or sulfonate (e.g., chloro, bromo, iodo, mesylate or tosylate), in the presence of a base such as an alkali metal hydride, hydroxide or carbonate, preferably potassium hydroxide, in a polar solvent such as water, dimethylsulfoxide (DMSO), THF or DMF, preferably a mixture of DMSO and water, and then removing the protecting group as described above. The reaction with $R^{17}Z$ is generally carried out at a temperature from about room temperature to about 100° C., preferably at about 50° C., for about five hours. Subsequent removal of the protecting group, as described above, yields the desired compound of formula IE.

Scheme 8 illustrates an alternative method of preparing compounds of the formula IE from the compound of formula XXVIIIA'. This method is the preferred method of making compounds of the formula IE wherein $R^{17}$ is a group such as an aryl or heteroaryl containing group, or when $R^{17}$ can not be attached, as illustrated in Scheme 7, by alkylation or aryl substitution methods. Referring to Scheme 8, the compound of formula XXVIIIA' is reacted with the appropriate compound of formula $R^{17}NH_2$ in a polar solvent such as THF, DMF or DMSO, preferably THF, at a temperature from about room temperature to about 100° C., preferably at the reflux temperature, for about four to eighteen hours. This reaction produces a compound of the formula XXX. The resulting compound of formula XXX is then converted into the corresponding compound of the formula XXVII by reducing the nitro group to an amino group using methods well known to those of skill in the art. Such methods are referred to above for the conversion of the compounds of the formula XXVIIA' into a compound of the formula XXVIIB in Scheme 6. Closure of the imidazole ring to form the corresponding compound of formula XXXII can then be accomplished by reacting the compound of formula XXXI from the above reaction with a compound of the formula

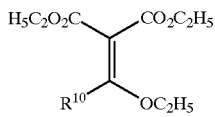

(wherein $R^{10}$ is defined as above) as described above for converting compounds of the formula XXVIIIB into those of the formula XXIX.

Removal of the protecting group from the compound of formula XXXII yields the corresponding compound of formula IE. This can be accomplished using methods well known in the art, for example, as described above for forming compounds of the formula ID from the corresponding compounds of the formula XXIX.

Compounds of the formula XXVIIIA', which are the starting materials used in the process of Scheme 8, can be synthesized as depicted in Scheme 8A and described below. The appropriate compound of formula IC (Scheme 3) wherein $R^2$ is fluoro is converted into its trifluoroacetamide derivative of the formula ICTFA, using methods described above. Such derivative is then nitrated, as described above or using other methods well known to those of skill in the art, to provide the corresponding nitro derivative of formula ICTFA'. Subsequent removal of the trifluoroacetamide group with an alkali metal carbonate or bicarbonate in methanol or THF, followed by protection with di-t-butyidicarbonate, as described above, yields the corresponding compound of formula XXVIIIA'.

Scheme 9 illustrates a method of preparing compounds of the formula IF, wherein $R^{10}$ and $R^{17}$ are as defined above. Referring to Scheme 9, the compound of formula XXVIIIB is reacted with a compound of the formula

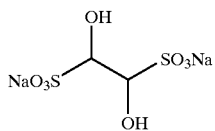

(sodium bisulfite ethane dione addition adduct) in water or another polar solvent such as THF, DMF or DMSO, preferably a mixture of water and a water miscible solvent such as THF, for about one to four hours. The reaction temperature can range from about 40° C. to about 100° C., and is preferably at about the reflux temperature.

Alternatively, the compound of formula XXVIIIB can be reacted with a compound of the formula

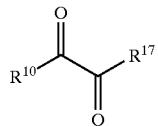

(double condensation reaction) in a polar solvent such as THF, water, or acetic acid, preferably a mixture of water and THF. This reaction is typically carried out at a temperature from about 40° C. to about 100° C., preferably at the reflux temperature, for about two to four hours.

Both of the foregoing procedures can also be used to convert the corresponding compounds wherein the t-Boc protecting group is replaced by another protecting group such as TFA (e.g., compounds of the formula XXVIIB) into quinoxolines.

The desired quinoxoline of formula IF can then be formed by deprotecting the compound formed in either of the foregoing reactions, using the method described above for converting a compound of the formula XXIX Into one of the formula ID or the method described above for removing the TFA group from a compound of the formula XXVIIA'.

Scheme 10 illustrates a method of preparing compounds of the formula I wherein $R^2$ and $R^3$, together with the benzo ring to which they are attached, form a benzoxazole ring system. Such a compound, wherein $R^1$ is hydrogen, is depicted in Scheme 10 as chemical formula IG. Referring to Scheme 10, a compound of the formula ICTFA', wherein Y is nitro or fluoro, is reacted with potassium acetate or another alkali or alkaline earth metal carboxylate in a solvent such as dimethylsulfoxide (DMSO), DMF or acetonitrile, preferably DMSO. This reaction is generally allowed to run for about 12–24 hours. Appropriate reaction temperatures range from about 70° C. to about 140° C. Approximately 100° C. is preferred.

The above reaction yields the compound of formula XXXIV, which can then be converted into the desired compound having formula IG by the following procedure. First, the compound of formula XXXXIV is reduced by reaction with hydrogen and a palladium or platinum catalyst such as palladium hydroxide in methanol at a temperature from about 0° C. to about 70° C., preferably at about room temperature, to form the corresponding amino derivative. The product of this reaction is then reacted with an acid chloride of the formula $R^{10}COCl$ or an acid anhydride of the formula $(R^{10}CO)_2O$ wherein $R^{10}$ is $(C_1-C_6)$alkyl, or a compound of the formula $R^{10}C(OCH_2H_5)_3$, in an appropriate inert solvent such as decafln, chlorobenzene or xylenes. A mixture of xylenes is preferred. This reaction is typically conducted at a temperature from about 120–150° C., preferably at about 140° C. When $R^{10}COCl$ is used as a reactant, it is preferable to add a stoicheometric amount of triethylamine (TEA) or another organic tertiary amine base and a catalytic amount of pyridinium p-toluenesulfonic acid or pyridinum p-toluenesulfonate (PT) to the reaction mixture. When $R^{10} C(OC_2H_5)_3$ is used as a reactant, it is preferable to add a catalytic amount of PPTS to the reaction mixture.

Removal of the trifluoroacetyl nitrogen protecting group yields the desired compound of the formula IG. This can be accomplished using methods well known to those of skill in the art, for example, reacting the protected compound with a lower alkanol and an aqueous alkali or alkaline earth metal (or ammonium) hydroxide or carbonate, aqueous sodium carbonate, at a temperature from about 50° C. to about 100° C., preferably at about 70° C., for about two to six hours.

Scheme 11 illustrates the preparation of compounds of the formula I wherein $R^1$ is hydrogen and $R^2$ and $R^3$, together with the benzo ring to which they are attached, form a benzothiazole ring system. These compounds are referred to in Scheme 11 and hereinafter as "compounds of the formula IH". Referrirg to Scheme 11, the compound of formula XXV' is reacted with trifluoroacetic anhydride to form the corresponding compound wherein the ring nitrogen is protected by a trifluoroacetyl group, and the resulting nitrogen protected compound is then reacted with two equivalents of trifluoromethanesulfonic acid and one equivalent of nitric acid to form the corresponding compound of formula XXXV, wherein there is a single nitro substituent on the benzo ring. The reaction with trifluoroacetic acid is typically conducted in the presence of pyridine. Both of the above reactions are typically conducted in a reaction inert solvent such as a chlorinated hydrocarbon solvent, preferably methylene chloride, at a temperature from about 0° C. to about room temperature, preferably at about room temperature.

The above transformation can also be accomplished using other nitration methods known to those skill in the art.

Reduction of the nitro group to an amine group can be accomplished as described above to provide a compound of the formula XXXV'.

The compound of formula XXXV' is then reacted with a carboxylic acid halide or anhydride of the formula $R^{10}COX$ or $(R^{10}CO)_2O$, wherein X is halo, and pyridine, TEA or another tertiary amine base, to form a compound of the formula XXXVI, which can then be converted to the desired compound having formula XXXVII by reacting it with Lawesson's reagent, which is depicted below.

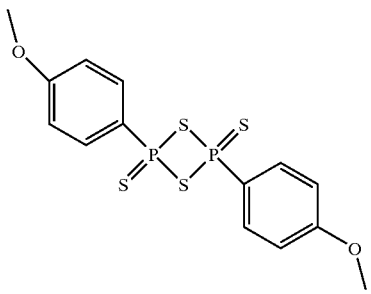

The reaction with $R^{10}COX$, wherein X is halo, or $(R^{10}CO)_2O$ is generally carried out at a temperature from about 0° C. to about room temperature, preferably at about room temperature. The reaction with Lawesson's reagent is generally carried out in a reaction inert solvent such as benzene or toluene, preferably toluene, at a temperature from about room temperature to about the reflux temperature of the reaction mixture, preferably at about the reflux temperature.

Closure to the benzothiazole ring and nitrogen deprotection to form the desired compound of formula IH can be accomplished by reacting the compound of formula XXXVII with potassium ferricyanide and sodium hydroxide in a mixture of water and methanol ($NaOH/H_2O/CH_3OH$), at a temperature from about 50° C. to about 70° C., preferably at about 60° C for about 1.5 hours.

Schemes 12 and 13 illustrate methods of preparing compounds of the formula I wherein $R^1$ is hydrogen, and $R^2$ and $R^3$ represent a variety of different substituents, as defined above, but do not form a ring.

Scheme 12 illustrates methods of preparing compounds of the formula I wherein: (a) $R^1$ is hydrogen and $R^2$ is $R^7R^8NO_2S$—; (b) $R^1$ and $R^2$ are both chloro; and (c) $R^1$ is hydrogen and $R^2$ is $R^{13}C(=O)$—. These compounds are referred to in Scheme 12, respectively, as compounds of formulas IJ, IK and IL.

Referring to Scheme 12, compounds of the formula IJ can be prepared by reacting the compound of formula XXVI with two or more equivalents of a halosulfonic acid, preferably chlorosulfonic acid, at a temperature from about 0° C. to about room temperature. Reaction of the chlorosulfonic acid derivative so formed with an amine having the formula $R^7R^8NH$, wherein $R^7$ and $R^8$ are defined as above, followed by removal of the nitrogen protecting group, yields the desired compound having formula IJ.

Compounds of the formula IK can be prepared by reacting the compound of formula XXVI with iodine trichloride in a chlorinated hydrocarbon solvent, followed by removal of the nitrogen protecting group. The reaction with iodine trichloride is typically carried out at a temperature from about 0° C. to about room temperature, and is preferably carried out at about room temperature in a similar fashion, the analogous mono- or dibrominated or mono- or diiododinated compounds can be prepared by reacting the compound of XXVI with N-iodosuccinimide or N-bromosuccinimide in a trifluromethanesulfonic acid solvent, followed by removal of the nitrogen protecting group as described above.

Reaction of the compound of XXVI with an acid halide of the formula $R^{13}COCl$ or an acid anhydride of the formula $(R^{13}CO)_2O$, with or without a reaction inert solvent such as a chlorinated hydrocarbon solvent, preferably methylene chloride, in the presence of Lewis acid such as aluminum chloride, at a temperature from about 0° C. to about 100° C., followed by nitrogen deprotection, yields the compound of formula IL. The reaction with the acid halide or anhydride can be carried out using other known Lewis acids or other Friedel-Crafts acylations methods that are known in the art.

The reactions described herein in which $NO_2$, $—SO_2NR^7R^8$, $—COR^3$, I, Br or Cl are introduced on the compound of formula XXVI, as depicted in Scheme 12 and described above, can be performed on any analogous compound wherein $R^2$ is hydrogen, $(C_1-C_6)$alkyl, halo, $(C_1-C_6)$alkoxy or $—NHCONR^7R^8$, producing compounds of the formula I wherein $R^2$ and $R^3$ are defined as in the definition of compounds of the formula I above.

Compounds that are identical to those of the formula IL, but which retain the nitrogen protecting group, can be converted into the corresponding O-acyl substituted compounds, ie., those wherein the $—C(=O)R^{13}$ group of formula IL is replaced with a $—O—C(=O)R^{13}$ group, using Baeyer-Villiger processes well known to those skilled In the art. The resulting compounds can be partially hydrolyzed to yield the corresponding hydroxy substituted compounds, and then alkylated to form the corresponding alkoxy substituted compounds. Also, such O-acyl substituted compounds can be used to prepare variably substituted benzisoxazoles, using methods well known to those of skill in the art such as using, in sequence, a Fries rearrangement, oxime formation, acylation and treatment with base. Such a process involves performing a Fries rearrangement of a compound of the formula XXXIII by treatment with a Lewis acid such as aluminum chloride ($AlCl_3$) neat or in a solvent such as chlorobenzene, at a temperature from about 100° C. to about 200° C., preferably at about 170° C. for about 1 to 2 hours, preferably for about 2 hours, to produce a compound of the formula XXXIX. Cleavage of the protecting group provides the corresponding compound of formula IS. Alternatively, the compound of formula XXXIX can be converted into its oxime using standard methods well known to those skilled in the art, such as treatment with hydroxylamine hydrochloride in an alcohol (e.g., methanol), in the presence of a base such as sodium acetate, at a temperature from about 20° C. to about 70° C., preferably at about 50° C. for about 5 to 20 hours. Acylation of the oxime using methods well known in the art, such as treatment with acetic anhydride and pyridine, followed by treatment of the isolated acyl oxime with a base such as sodium hydride, In a solvent such as DMF, NMP or DMSO, produces the corresponding protected benzisoxazole. Cleavage of the protecting group under standard conditions, as described above, yields the desired compound of formula IT.

Scheme 13 illustrates methods of making compounds of the formula I wherein: (a) $R^1$ is hydrogen and $R^2$ is chloro; (b) $R^1$ is hydrogen and $R^2$ is cyano; (c) $R^1$ is hydrogen and $R^2$ is amino; and (d) $R^1$ is hydrogen and $R^2$ is $R^{13}C(=O)N(H)$—. These compounds are referred to in Scheme 13, respectively, as compounds of the formula IM, IN, IP and IQ.

Compounds of formula IM can be prepared from compounds of the formula XXXV' by generation of a diazonium salt with, for instance, an alkali metal nitrite and strong mineral acid (e.g., hydrochloric acid, sulfuric acid, hydrobromic acid) in water, followed by reaction with a copper halide salt, such as copper (I) chloride. Nitrogen deprotection by the methods described above yields the desired compound of formula IM. Alternative methods for the generation of diazonium salts, as known and practiced by those of skill in the art, can also be used. The foregoing reaction is generally carried out at temperatures ranging from about 0° C. to about 60° C, preferably about 60° C. for about 15 minutes to one hour.

Reaction of the diazodium salt, prepared as described above, with potassium iodide in an aqueous medium provides the analogous iodide derivative. This reaction is generally carried out at a temperature from about 0° C. to about room temperature, preferably at about room temperature. The resulting compound, or its analogous N-tert-butylcarbonate protected form, can be used to prepare the corresponding cyano derivative by reaction with copper (I) cyanide and sodium cyanide in DMF, N-methylpyrrolidone (NMP), N,N-dimethylpropylurea (DMPU) or DMSO, preferably NMP, at a temperature from about 50° C. to about 180° C., preferably at about 175° C. Nitrogen deprotection as described above provides the corresponding desired compound of formula IN.

The above described iodide, bromide or diazonium salt derivative can also be used to access a variety of other substituents such as aryl, acetylene and vinyl substituents, as well as the corresponding carbonyl esters and amides, by palladium and nickel catalyzed processes known to those of skill in the art, such as Heck, Suzuki and Stille couplings and Heck carbonylations.

Nitrogen deprotection of the compound of formula XXXV' provides the compound of the formula IP.

The compound of formula XXXV' can be reacted with a acyl group having the formula $R^{13}COCl$ or $(R^{13}CO)_2O$ using the methods described above, followed by nitrogen deprotection to provide compounds of the formula IQ. In a similar fashion, treatment of the protected amine with a compound having the formula $R^{13}SO_2X$, when X is chloro or bromo, followed by nitrogen deprotection, provides the corresponding sulfonamide derivative.

Other suitable amine protecting groups that can be used, alternatively, in the procedures described throughout this document include —$COCF_3$, —$COCCl_3$, —$COOCH_2CCl_3$, —$COO(C_1$–$C_6)$alkyl and —$COOCH_2C_8OH_5$. These groups are stable under the conditions described herein, and may be removed by methods described for each in Greene's "Protective Groups in Organic Chemistry", referred to above.

Compounds of the formula I wherein $R^1$ is other than hydrogen can be prepared as described above, such as the reductive amination ring formation by which compound XXIV In Scheme 3 ($R^1$=benzyl) is formed, and by the methods described below. Compounds of the formula I wherein $R^1$ is hydrogen can be converted into the corresponding compounds wherein $R^1$ is other than hydrogen by treating them with an equivalent amount of an aldehyde ($R^1CHO$) or ketone ($R^1R^1CO$ wherein the two $R^1$'s are the same or different) and a reducing agent, preferably a hydride reagent such as sodium traicetoxborohydride or sodium cyanoborohydride, in a solvent such as methylene chloride, tetrahydrofuran or dioxane. The addition of acid to facilitate the reaction may be necessary in some cases, and acetic acid is commonly used. The temperature of this reaction is typically ambient for a period of about 0.5 to 24 hours. Commonly used methods are described in *J. Ora. Chem.* 1998, 61, 3849.

Compounds of the formula I wherein $R^1$ is other than hydrogen can also be prepared by subjecting the corresponding compounds wherein $R^1$ is hydrogen to an alkylation reaction, using methods well known to those of skill in the art. For example, the compound wherein $R^1$ is hydrogen is treated with an equivalent amount or an excess of $R^1X$, wherein $R^1$ is other than hydrogen and X is halo, preferably bromo or iodo, or an O-sulfate ester of $R^1OH$. This reaction is typically performed neat or in polar solvent such as water, dimethylformamide or dimethylsulfoxide, usually in the presence of base, such as but not limited to an alkyli metal carbonate, for instance. The temperature of the reaction will generally range from about 20–120° C. (preferably, it will be about 100° C.) for a period of about 0.1 to 24 hours.

Compounds of the formula I wherein $R^1$ is other than hydrogen can also be prepared by converting the corresponding compounds wherein $R^1$ is hydrogen into amides by reacting them with a compound of the formula $R^1C(=O)X$, wherein X is defined as above, using methods well known to those of skill in the art, and then reducing the resulting amide with borane or lithium aluminum hydride. The reduction step is usually carried out in an ethereal solvent such as ethyl ether or THF at a temperature from about 20,° C. to about 70° C. for about one to twenty hours, to produce the desired amine.

In each of the reactions discussed above, or illustrated in Schemes 1–13, above, pressure is not critical unless otherwise indicated. Pressures from about 0.5 atmospheres to about 5 atmospheres are generally acceptable, with ambient pressure, i.e., about 1 atmosphere, being preferred as a matter of convenience.

The compounds of the formula I and their pharmaceutically acceptable salts (hereafter "the active compounds") can be administered via either the oral, transdermal e.q., through the use of a patch), intranasal, sublingual, rectal, parenteral or topical mutes. Transdermal and oral administration are preferred. These compounds are, most desirably, administered in dosages ranging from about 0.25 mg up to about 1500 mg per day, preferably from about 0.25 to about 300 mg per day in single or divided doses, although variations will necessarily occur depending upon the weight and condition of the subject being treated and the particular route of administration chosen. However, a dosage level that is in the range of about 0.01 mg to about 10 mg per kg of body weight per day is most desirably employed. Variations may nevertheless occur depending upon the weight and condition of the persons being treated and their individual responses to said medicament, as well as on the type of pharmaceutical formulation chosen and the time period and interval during which such administration is carried out. In some instances, dosage levels below the lower limit of the aforesaid range may be more than adequate, while in other cases still larger doses may be employed without causing any harmful side effects, provided that such larger doses are first divided into several small doses for administration throughout the day.

The active compounds can be administered alone or in combination with pharmaceutically acceptable carriers or diluents by any of the several routes previously indicated. More particularly, the active compounds can be administered in a wide variety of different dosage forms, e.g., they may be combined with various pharmaceutically acceptable inert carriers in the form of tablets, capsules, transdermal patches, lozenges, troches, hard candies, powders, sprays, creams, salves, suppositories, jellies, gels, pastes, lotions, ointments, aqueous suspensions, injectable solutions, elixrs, syrups, and the like. Such carriers include solid diluents or fillers, sterile aqueous media and various non-toxic organic solvents. In addition, oral pharmaceutical compositions can be suitably sweetened and/or flavored. In general, the active compounds are present in such dosage forms at concentration levels ranging from about 5.0% to about 70% by weight.

For oral administration, tablets containing various excipients such as microcrystalline cellulose, sodium citrate, calcium carbonate, dicalcium phosphate and glycine may be employed along with various disintegrants such as starch (preferably com, potato or tapioca starch), alginic add and certain complex silicates, together with granulation binders like polyvinylpyrrolidone, sucrose, gelatin and acacia. Additionally, lubricating agents such as magnesium steamate, sodium lauryl sulfate and talc can be used for tabletting purposes. Solid compositions of a similar type may also be employed as fillers in gelatin capsules; preferred materials in this connection also include lactose or milk sugar] as well as high molecular weight polyethylene glycols. When aqueous suspensions and/or elixir are desired for oral administration the active ingredient may be combined with various sweetening or flavoring agents, coloring matter and, if so desired, emulsifying and/or suspending agents, together with such diluents as water, ethanol, propylene glycol, glycerin and various combinations thereof.

For parenteral administration, a solution of an active compound in either sesame or peanut oil or in aqueous propylene glycol can be employed. The aqueous solutions should be suitably buffered (preferably pH greater than 8), if necessary, and the liquid diluent first rendered isotonic. These aqueous solutions are suitable for intravenous injectin purposes. The oily solutions are suitable for intraarticular, intramuscular and subcutaneous injection purposes. The preparation of all these solutions under sterile conditions is readily accomplished by standard pharmaceutical techniques well known to those skilled in the art.

It is also possible to administer the active compounds topically and this can be done by way of creams, a patch, jellies, gels, pastes, ointments and the like, in accordance with standard pharmaceutical practice.

BIOLOGICAL ASSAY

The effectiveness of the active compounds in suppressing nicotine binding to specific receptor sites is determined by the following procedure which is a modification of the methods of Lippiello, P. M. and Femandes, K. G. (in *The Binding of L-[³H]Nicotine To A Single Class of High-Affinity Sites in Rat Brain Membranes, Molecular Pharm.*, 29, 448–54, (1986)) and Anderson, D. J. and Americ, S. P. (in *Nicotinic Receptor Binding of ³H-Cystsine, ³H-Nicotine and ³H-Methylcarmbamylcholine In Rat Brain, European J. Pharm.*, 253, 261–7 (1994)).

PROCEDURE

Male Sprague-Dawley rats (200–300 g) from Charles River were housed in groups in hanging stainless steel wire cages and were maintained on a 12 hour light/dark cycle (7 a.m.–7 p.m. light period). They received standard Purina Rat Chow and water ad libitum.

The rats were killed by decapitation. Brains were removed immediately following decapitation. Membranes were prepared from brain tissue according to the methods of Lippiello and Fernandez (*Molec Pharmacol*, 29, 448–454, (1986) with some modifications. Whole brains were removed, rinsed with ice-cold buffer, and homogenized at 0° in 10 volumes of buffer (w/v) using a Brinkmann Polytron™, setting 6, for 30 seconds. The buffer consisted of 50 mM Tris HCl at a pH of 7.5 at room temperature. The homogenate was sedimented by centrifugation (10 minutes; 50,000×g; 0 to 4° C. The supematant was poured off and the membranes were gently resuspended with the Polytron and centrifuged again (10 minutes; 50,000×g; 0 to 4° C. After the second centrifugation, the membranes were resuspended in assay buffer at a concentration of 1.0 g/100 mL. The composition of the standard assay buffer was 50 mM Tris HCl, 120 mM NaCl, 5 mM KCl, 2 mM $MgCl_2$ 2 mM $CaCl_2$ and has a pH of 7.4 at room temperature.

Routine assays were performed in borosilicate glass test tubes. The assay mixture typically consisted of 0.9 mg of membrane protein in a final incubation volume of 1.0 mL. Three sets of tubes were prepared wherein the tubes in each set contained 50 μL of vehicle, blank, or test compound solution, respectively. To each tube was added 200 μL of [³H]-nicotine in assay buffer followed by 750 μL of the membrane suspension. The final concentration of nicotine in each tube was 0.9 nM. The final concentration of cytisine in the blank was 1 μM. The vehicle consisted of deionized water containing 30 μL of 1 N acetic acid per 50 mL of water. The test compounds and cytisine were dissolved in vehicle. Assays were initiated by vortexing after addition of the membrane suspension to the tube. The samples were incubated at 0 to 40 ° C. in an iced shaikng water bath. Incubations were terminated by rapid filtration under vacuum through Whatman GF/B™ glass fiber filters using a Brandel™ multi-manifold tissue harvester. Following the initial filtration of the assay mixture, filters were washed two times with ihce-cold assay buffer (5 m each). The filters were then placed in counting vials and mixed vigorously with 20 ml of Ready Safe™ (Beckman) before quantification of radioactivity. Samples were counted in a LKB Wallach Rackbeta™ liquid scintillation counter at 40–50% efficiency. All determinations were in triplicate.

CALCULATIONS

Specific binding (C) to the membrane is the difference between total binding in the samples containing vehicle only and membrane (A) and non-specific binding in the samples containing the membrane and cytisine (B), i.e., Specific binding=(C)=(A)–(B).

Specific binding in the presence of the test compound E is the difference between the total binding in the presence of the test compound (D) and non-specific binding (B), i.e., (E)=)–(B).

% Inhibition=(1–((E)/(C)) times 100.

The compounds of the invention that were tested in the above assay exhibited $IC_{50}$ values of less than 10 μM.

The following experimental examples illustrate, but do not limit the scope of, this invention.

EXAMPLE 1

5,6-DIFLUORO-11-AZA-TRICYCLO[7,3,1,0$^{2,7}$] TRIDECA-2,4,6-TRIENE HYDROCHLORIDE

A Cyclopent-3-enyl-(2,3-difluoro-6-methoxy-phenyl)-methanol (For leading metalation references, see Example 6A. Cyclopent-3-enecarbaldehyde was derived from the lithium aluminum hydride reduction of cyclopent-3-enecarboxylic acid methoxy-methyl-amide, the preparation of which appears in Example 2A. For reduction conditions, see: Garigipati, R. S.; Tschaen, D. M.; Weinreb, S. M.; *J. Amer. Chem. Soc.* 1990, 112, 3475–3482.)

1,2-Difluoro-4-methoxy-benzene (10 g, 69.4 mmol) was stirred in anhydrous (anh.) THF (80 mL) in a dry 250 mL three neck round bottomed flask (3NRB flask) at –78° C.

under nitrogen ($N_2$). To this was added n-butyllithium (n-BuLi) (28 mL, 2.5M/hexanes soln., 70 mmol) over 5 minutes. After stirring below −70° C for 4.5 hours (h), a solution of cyclopent-3-enecarbaldehyde (5.7 g, 69.4 mmol) in anh. THF (30 mL) was added via addition funnel along the reaction vessel wall while keeping the internal temperature below −70 ° C. After stirring for ½ hour (h), the reaction mixture was poured into a saturated aqueous ammonium chloride solution (sat. aq. $NH_4Cl$ soln.) (100 mL), and the mixture was stirred and extracted with ethyl ether ($Et_2O$) (2×50 mL). The organic layer was washed with brine (50 mL), dried ($Na_2SO_4$), filtered, concentrated and chromatographed on silica gel to provide an oil (6.64 g, 40%). (Thin layer chromatography (TLC) 20%EtOAc/hexanes $R_f$ 0.16). $^1H$ NMR ($CDCl_3$) δ7.01 (ddd, J=9.0 Hz, 1H), 6.58 (m, 1H), 5.72 (ddd, J=5.8,4.5,2.2 Hz, 1H), 5.62 (ddd, J=5.8,4.5,2.2 Hz, 1H), 4.79 (br d, J=9.5 Hz, 1H), 3.85 (s, 3H), 3.20 (br s, OH), 2.87 (m, 1H), 2.52 (AB m, 2H), 1.99 (AB m, 2H). GCMS m/e 240 ($M^+$).

B) 2-Cyclopent-3-enylmethyl-3,4-difluoro-1-methoxy-benzene (For related examples, see: Leeson, P. D.; Emmett, J. C.; Shah, V. P.; Showell, G. A.; Novelli, R. *J. Med. Chem.* 1989, 32, 320–336.)

Cyclopent-3-enyl-(2,3difluoro-6methoxy-phenyl)-methanol (6.64 g, 27.7 mmol) and triethylsilane (3.38 g, 29 mmol) were stirred in $CH_2Cl_2$ (40 mL) at 0° C. To this solution was added trfluoroacetic acid (17.3 mL, 224 mmol). The mixture was stirred at ambient temperature for 18 hours. The mixture was concentrated to an oil, which was dissolved in hexanes (100 mL), washed with water ($H_2O$) (2×50 mL) and a saturated aqueous sodium bicarbonate solution (sat. aq. $NaHCO_3$ soln.) (50 mL), and then dried (sodium sulfate ($Na_2SO_4$)), filtered, concentrated and chromatographed on Silica gel to provide an oil (3.67 g, 59%). (TLC hexanes $R_f$ 0.38).

$^1H$ NMR ($CDCl_3$) δ6.92 (ddd, J=9.3 Hz, 1H), 6.49 (br d, J=9.3 Hz, 1H), 5.66 (br s, 2H), 3.78 (s, 3H), 2.72 (dd, J=7.5,2.0 Hz, 2H), 2.57 (m, 1H), 2.36 (AB m, 2H), 2.06 (AB dd, J=14.2,5.5 Hz, 2H). GCMS m/e 224 ($M^+$).

C) 2-Cyclopent-3-enylmethyl-3,4-difluoro-phenol

2-Cyclopent-3-enylmethyl-3,4-difluoro-1-methoxy-benzene (3.67 g, 16.38 mmol) and n-$Bu_4Nl$ (7.17 g, 19.4 mmol) were stirred in dry $CH_2Cl_2$ (50 mL) at −78 ° C. under nitrogen ($N_2$). To this was added boron trichloride ($BCl_3$) (22 mL, 1M $CH_2Cl_2$ soln., 22 mmol) over 2 minutes (min.). After 5 min., the solution was allowed to warm to room temperature (rt) and stirred for 2 hours. The reaction was quenched with $H_2O$ (100 mL) and stirred for 1 hour. The layers were separated and the aq. layer extracted with methylene chloride ($CH_2Cl_2$) (2×30 mL). The combined organic layer was washed with $H_2O$ (2×50 mL), and a sat. aq. $NaHCO_3$ soln. (50 mL), dried through a cotton plug, concentrated and chromatographed on silica gel to provide an oil (3.30 g, 96%). (TLC 50% ethyl acetate (EtOAc)/hexanes (hex) $R_f$ 0.70). $^1H$ NMR ($CDCl_3$) δ6.85 (ddd, J=9.0 Hz, 1H), 6.46 (m, 1H), 5.68 (br s, 2H), 4.76 (br s, 1H), 2.71 (d, J=8.0 Hz, 2H), 2.61 (m, 1H), 2.39 (AB m, 2H), 2.09 (AB dd, J=14.0,5.4 Hz, 2H). GSMS m/e 210 ($M^+$).

D) Trifluoro-methanesulfonic acid 2-cyclorent-3-enylmethyl-3,4difluoro-phenyl ester (For a leading reference, see: Su, T. M.; Sliwinski, W. F.; Schleyer, P. v. R. *J. Am. Chem. Soc.* 1969, 91, 5386.)

2-Cyclopent-3-enylmethyl-3,4-difluoro-phenol (3.30 g, 15.7 mmol) and pyrdine (2.49 g, 31.5 mmol) were stirred in $CH_2Cl_2$ (50 mL) at −78 ° C. under $N_2$ and treated with trifluoromethane sulfonic anhydride (6.20 g, 22.0 mmol) dropwise over 20 min. The mixture was allowed to warm to rt and stirred for ½ hour then poured into 1N aq. HCl soln. and shaken. The layers were separated and the aq. layer was extracted with $CH_2Cl_2$(2×30 mL). The combined organic layer was washed with $H_2O$ (50 mL), and a sat. aq. $NaHCO_3$ soln. (50 mL), dried through a cotton plug, concentrated and chromatographed on silica gel to provide an oil (4.34 g, 81%). (TLC 30%EtOAc/Hex $R_f$ 0.60). $^1H$ NMR ($CDCl_3$) δ7.13–7.03 (2H), 5.67 (br s, 2H), 2.82 (dd, J=7.5,2.0 Hz, 2H), 2.58 (m, 1H), 2.40 (dd, J=14.0,8.0 Hz, 2H), 2.05 (dd, J=14.0,5.5 Hz, 2H). GCMS m/e 342 ($M^+$).

E) 5.6-Difluorotricyclo[7.2.1.0$^{2,7}$]dodeca-2(7), 3,5,10-tetraene

Trifluoro-methanesulfonic acid 2-cyclopent-3-enylmethyl-3,4-difluoro-phenyl ester (340 mg, 0.99 mmol), was dissolved In DMF (5 mL) under a $N_2$ atmosphere and treated with diisopropylethylamine (0.28 mL, 1.5 mmol), potassium acetate (981 mg, 10.0 mmol) and tri-o-tolylphosphine (12 mg, 0.04 mmol). This mixture was stirred and degassed (3 vacuum/$N_2$ purge cycles) and then treated with palladium acetate (5 mg, 0.02 mmol). After 20 min. the mixture was warmed to 100° C. for 18 hours, cooled and poured into brine (50 mL). The resulting mixture was extracted with hexanes (4×25 mL) and the combined organic layer was washed with a sat. aq. $NaHCO_3$ soln. (10 mL), water ($H_2O$) (10 mL), brine (10 mL), dried (magnesium sulfate ($MgSO_4$)), filtered and and chromatographed on silica gel to provide an oil (110 mg, 60%). (TLC hexanes $R_f$ 0.58). $^1H$ NMR ($CDCl_3$) δ6.80 (ddd, J=6.6,8.1, 8.3 Hz, 1H), 6.68 (m, 1H), 6.17 (dd, J=5.5,2.8 Hz, 1H), 5.77 (dd, J=5.5,2.8 Hz, 1H), 3.29 (br s, 1H), 2.96 (br s, 1H), 2.84 (AB dd, J=17.9,5.0 Hz, 1H), 2.54 (AB d, J=17.9 Hz, 1H), 2.19 (m, 1H), 1.77 (d, J=10.5 Hz, 1H). GCMS m/e 192 ($M^+$).

F) 5.6-Difluoro-10,11-dihydroxytricyclo[7.2.1.0$^{2,7}$]dodeca-2(7),3.5-triene 5,6-Difluorotricyclo[7.2.1.0$^{2,7}$]dodeca-2(7),3,5,10-tetraene (714 mg, 3.72 mmol) and N-methyl morpholine N-oxide (553 mg, 4.10 mmol) were stirred in acetone (20 mL) and $H_2O$ (3 mL). To this was added a solution of osmium tetraoxide ($OsO_4$ (0.2 mL, 2.5%wt. soln. In t-butanol (t-BuOH), 0.02 mmol). After 18 hours, the mixture was concentrated to an oil, dissolved in a minimum of $CH_2Cl_2$ and filtered through a silica pad (3×3 mm) eluting with 20% EtOAc/hexanes. Product containing fractions were concentrated to an oil (850 mg, 100%). (TLC 20% EtOAc/hexanes $R_f$ 0.37). $^1H$ NMR ($CDCl_3$) δ6.88 (ddd, J=9.3,8.5,7.6 Hz, 1H), 6.78 (m, 1H), 4.01 (AB d, 2H), 3.06 (brs, 1H), 2.92 (AB dd, J=17.9,5.0 Hz, 1H), 2.75 (br AB, J=17.9 Hz, 1H), 2.44 (br s, 1H), 2.32 (2-OH), 2.26 (m, 1H), 1.50 (d, J=7.8 Hz, 1H). GCMS m/e 226 ($M^+$).

G) 5.6-Difluoro-11-aza-tricyclo[7.3.1.0$^{2,7}$]trideca-2(7),3.5-triene hydrochloride 5,6-Difluoro-10,11-dihydroxytricyclo[7.2.1.0$^{2,7}$]dodeca-2(7),3,5-triene (840 mg, 3.72 mmol) was stirred in a parr bottle in ethanol (EtOH) (30 mL) and $H_2O$ (10 mL). To this a soln. of sodium periodate ($NaIO_4$) (810 mg, 3.72 mmol) in $H_2O$ (5 mL) was added. The resulting milky white dispersion was stirred 15 min., then treated with 37% aq. ammonium hydroxide ($NH_4OH$) soln. (25 mL) and palladium hydroxide (Pd$(OH)_2$) (360 mg, 20%wt/C) and shaken under 45 psi of $H_2$. After 18 hours, the mixture was filtered through a Celite pad and rinsed with EtOH and a 3:1 ethanol: water mixture. The filtrate was concentrated to an oily solid which was dissolved in EtOAc (50 mL) and washed with sat. aq. sodium carbonate ($Na_2CO_3$) soln. (2×20 mL). The organic layer was dried sodium sulfate ($Na_2SO_4$)), filtered, concentrated and chromatographed on Silica gel to provide an oil (330 mg, 42%). (TLC 5%MeOH/CH$_2$Cl$_2$ R$_f$ 0.36). $^1$H NMR (CDCl$_3$) δ6.92 (ddd, J=8.1,8.5,10.0 Hz, 1H), 6.74 (m, 1H), 3.02–2.93 (4H), 2.83–2.71 (3H), 2.09 (br s, 1H), 1.98 (br d, J=12.5 Hz, 1H), 1.82 (br d, J=12.5 Hz, 1H). GSMS m/e 209 (M$^+$). APCl MS m/e 209.8 [(M+1)$^+$].

The product was dissolved in methanol (CH$_3$OH) and treated with 3M hydrochloric acid (HCl)/EtOAc (3 ml). The resulting slurry was concentrated, dissolved in a minimum of MeOH, saturated with Et$_2$O and stirred for 18 hours. The solids were filtered to give white solid (335 mg, 86%). mp 290–305 °C.

EXAMPLE 2

11-BENZYL-6-METHOXY-11-AZA-TRICYCLO [7.3.1.0$^{2,7}$]TRIDECA-2(7),3,5-TRIENE HYDROCHLORIDE

A) Cyclopent-3-enecarboxylic acid methoxy-methylamide (For preparation of cyclopent-3-enecarboxylic acid, see: Depres, J-P.; Greene, A. E. *J. Org. Chem.* 1984, 49, 928–931, and for more recent approaches, see: a) Nugent, W. A.; Feldman, J.; Calabrese, J. C. *J. Am. Chem. Soc.* 1995, 117, 8992–8998, and b) Marinez, L. E.; Nugent, W. A.; Jacobsen, E. N. *J. Org. Chem.* 1996, 61, 7963–7966. For related methods for amide formation, see: Nitz, T. J.; Volkots, D. L.; Aldous, D. J.; Oglesby, R. C. *J. Org. Chem.* 1994, 59, 5828–5832.)

Cyclopent-3-enecarboxylic acid (65.6 g, 586 mmol) in CH$_2$Cl$_2$ (1 L) was treated with carbonyl diimidazole (100 g, 617 mmol) in portions. After ~¾ h, the resulting solution was treated with N,O-dimethylhydroxylamine (60.8 g, 623 mmol) and the mixture was stirred for 40 h. The reaction was quenched with 1N aq. HCl soln. (600 mL), shaken and the layers were separated. The aq. layer was extracted with CH$_2$Cl$_2$ (2×100 mL). The combined organic layer was washed with 1N aq. HCl soln. (100 mL), H$_2$O (2×150 mL), 50% sat. eq. Na$_2$CO$_3$ soln./brine (200 mL) and dried through a cotton plug. The filtrate was diluted with EtOAc to ~10%EtOAc/CH$_2$Cl$_2$ and filtered through a silica pad (10× 10 mm) eluting with 10%EtOAc/CH$_2$Cl$_2$ to remove baseline color. Concentration affords a liquid (86 g, 95%). (TLC 10%EtOAc/CH$_2$Cl$_2$ R$_f$ 0.56). $^1$H NMR (CDCl$_3$) δ5.64 (br s, 2H), 3.69 (s, 3H), 3.47 (m, 1H), 3.19 (s, 3H), 2.61 (m, 4H). GSMS m/e 155 (M$^+$).

B) Cyclopent-3-enyl-(2,6-dimethoxy-phenyl)-methanone (For a leading reference, see: Koft, E. R.; Smith, A. B., III. *J. Am. Chem. Soc.* 1982, 104, 2659.)

1,3-Dimethoxybenzene (31.9 g, 231 mmol) was stirred in anh. Et$_2$O (200 mL) at 0° C. under N$_2$ and treated with n-butyllithlum (n-BuLi) (92.5 mL, 2.5M/hexanes soln., 231 mmol) over 5 minutes. The solution was brought to reflux for 4 h, then cooled to −78° C. The slurry was treated with cyclopent-3-enecarboxylic acid methoxy-methyl-amide (35.9 g, 231 mmol) dropwise over ~1 hour, then the mixture was stirred for 18 hours (the cooling bath evaporated overnight). The mixture was poured into 1 N eq. HCl soln. (200 mL) and shaken. The layers were separated and the aq. layer extracted with Et$_2$O (2×100 mL). The organic layer was washed with H$_2$O (50 mL), and a sat. eq. NaHCO$_3$ soln. (100 mL), dried (Na$_2$SO$_4$), filtered through a silica plug and concentrated to an oil (52.6 g, 98%). (TLC 10%EtOAc/hexanes R$_f$ 0.25). $^1$H NMR (CDCl$_3$) δ7.24 (t, J=8.4 Hz, 1H), 6.24 (d, J=8.4 Hz, 2H), 5.63 (br s, 2H), 3.76 (s, 6H), 3.68 (m, 1H), 2.75 (m, 2H), 2.48 (m, 2H) GSMS m/e 232 (M$^+$).

C) Cyclopent-3-enyl-(2-hydroxy-6-methoxy-phenyl)-methanone (For a leading reference, see: Nagaoka, H.; Schmid, G.; Iio, H.; Kishi, Y. *Tetrahedron Left.* 1981, 22, 899.)

Cydopent-3-enyl-(2,6dimethoxy-phenyl)-methanone (52.6 g, 226 mmol) was stirred in CH$_2$Cl$_2$ (200 mL) at −78° C. under N$_2$ and treated with bomn trichloride BCl$_3$) (273 mL, 1M CH$_2$Cl$_2$ soln., 273 mmol) over 30 min. The mixture was allowed to warm to ambient temperature and was treated with additional BCl$_3$ (41.0 mL, 1M CH$_2$Cl$_2$ soln., 41.0 mmol). After the mixture was stirred 20 min., it was poured slowly into H$_2$O (300 mL) and stirred for 30 min. The layers were separated and the aq. layer was extracted with CH$_2$Cl$_2$ (2×50 mL). The combined organic layer was washed with H$_2$O (3×100 mL), sat. aq. NaHCO$_3$ soln. (100 mL), dried through a cotton plug and filtered through a Silica pad to remove baseline color. Concentration affords an amber oil (46.0 g, 93%). (TLC 10%EtOAc/hexanes R$_f$ 0.50). $^1$H NMR (CDCl$_3$) δ7.32 (t, J=8.5 Hz, 1H), 6.57 (dd, J=8.5,1.0 Hz, 1H), 6.38 (dd, J=8.5,1.0 Hz, 1H), 5.66 (br s, 2H), 4.31 (m, 1H), 3.89 (s, 3H), 2.80–2.83 (4H). GSMS m/e 218 (M$^+$).

D) Trifluoro-methanesulfonic acid 2-(cyclopent-3-enecarbonyln-3-methoxy-phenyl ester Cyclopent-3-enyl-(2-hydroxy-6-methoxy-phenyl-methanone (45.0 g, 206 mmol) and pyridine (36.0 g, 453 mmol) were stirred in CH$_2$Cl$_2$ (250 mL) at −78 °C. under N$_2$. To this a solution of trfluoromethane sulfonic anhydride (75.7 g, 268 mmol) in CH$_2$Cl$_2$ (100 mL) was added dropwise over ½ h. The mixture was allowed to warm to ambient temperature, stirred 1 h, then poured into 1 N aq. HCl soln. (250 mL). The mixture was shaken, the layers were separated, and the organic layer was washed with 1N aq. HCl soln. (3×150 mL), H$_2$O (2×100 mL), sat. aq. NaHCO$_3$ soln. (100 mL) and finally brine (100 mL). The organic layer was dried through a cofton plug and concentrated to an oil which was chromatographed through a Silica gel plug eluting with 10%EtOAc/hexanes to afford after concentration an oil (62.5 g, 87%). (TLC 10%EtOAc/hexanes R$_f$ 0.14). $^1$H NMR (CDCl$_3$) δ7.41 (t, J=8.5 Hz, 1H), 6.95 (dd, J=8.5,1.0 Hz, 2H), 5.64 (br s, 2H), 3.86 (s, 3H), 3.73 (m, 1H), 2.70 (m, 2H), 2.57 (m, 2H). GSMS m/e 350 (M$^+$).

E) 6-Methoxytricyclo[7.2.1.0$^{2,7}$]dodeca-2(7),3,5,10-tetraene-8one (For leading references, see: Heck, R. F. *Org. React.* (N.Y.) 1982, 27, 345, and Cabri, W.; Candiani, I. *Acc. Chem. Res.* 1995, 28, 2–7.)

Trifluoro-methanesulfonic acid 2-(cyclopent-3-enecarbonyl)-3-methoxy-phenyl ester (45.0 g, 129 mmol) was dissolved in DMF (100 mL) under a N$_2$ atmosphere and treated with triethylamine (19.5 g, 193 mmol), potassium acetate (1.89 g, 19.0 mmol) and 1,3-bis(diphenylphosphino) propane (5.30 g, 12.9 mmol). This mixture was stirred and degassed (3 vacuum/N$_2$ purge cycles) then treated wlth palladium acetate (1.16 g, 5.14 mmol). After 20 min. the mixture was warmed to 130° C. for 1 hour, cooled and poured into brine (300 mL). The resulting mixture was extracted with EtOAc (4×100 mL) and the combined organic layer was washed with sat. aq. NaHCO$_3$ soln. (100 mL), H$_2$O (100 mL), and brine (100 mL), dried (MgSO$_4$), filtered and evaporated to an oil. (55 g). The oil was chromatographed on silica gel to provide product as a white solid (12.0 g, 47%). (TLC 25%EtOAc/hexanes R$_f$ 0.27). $^1$H NMR (CDCl$_3$) δ7.29 (t, J=8.0 Hz, 1H), 6.84 (d, J=8.0 Hz, 1H), 6.73 (d, J=8.0 Hz, 1H), 6.63 (dd, J=5.0,3.0 Hz, 1H), 6.15 (dd, J=5.0,3.0 Hz, 1H), 3.87 (s, 3H), 3.60 (br s, 1H), 3.39 (br s, 1H), 2.56 (AB m, 2H). $^{13}$C NMR 195.38, 161.61, 149.82, 143.47, 133.77, 131.84, 131.80, 117.51, 111.46, 57.63, 55.96, 47.63, 47.51. GSMS m/e 200 (M$^+$). mp 135–136° C.

F) 6-Methoxytricyclo[7.2.1.0$^{2,7}$]dodeca-2(7),3,5,10-tetraene (For a discussion, see: Fieser and Fieser, *Reagents for Organic Synthesis,* (N.Y.) 1967, I, p.435.)

6-Methoxytricyclo[7.2.1.0$^{2,7}$]dodeca-2(7),3,5,10-tetraene-8-one (3.0 g, 15 mmol) and pulverized KOH (5.05 g, 90 mmol) were warmed in ethylene glycol (40 mL) until solution occurred. The mixture was cooled to room temperature, treated with hydrazine hydrate (3.0 g, 60 mmol) and heated to reflux for 2 hours. The reflux condenser was replaced with a distilling head and distillates were collected from 120–190° C. These distillates were diluted with H$_2$O (100 mL) and extracted with EtOAc (4×40 mL). The organic layer was washed with H$_2$O (4×30 mL), and brine (25 mL), dried (MgSO$_4$), filtered and concentrated to an oil (2.68 g, 96%). (TLC 50%EtOAc/hexanes R$_f$ 0.67). $^1$H NMR (CDCl$_3$) δ7.18 (t, J=8.0 Hz, 1H), 6.82 (d, J=8.0 Hz, 1H), 6.77 (d, J=8.0 Hz, 1H), 6.32 (dd, J=5.0,3.0 Hz, 1H), 5.93 (dd, J=5.0,3.0 Hz, 1H), 3.91 (s, 3H), 3.45 (dd, J=5.0,1.5 Hz, 1H), 3.11 (br s, 1H), 2.88 (AB dd, J=17.0,5.0 Hz, 1H), 2.58 (AB d, J=17.0 Hz, 1H), 2.31 (m, 1H), 1.96 (d, J=9.5 Hz, 1H).

G) 6Methoxy-10,11-dihydroxytricyclo[7.2.1.0$^{2,7}$]dodeca-2(7),3,5,10-triene

6-Methoxytricyclo[7.2.1.0$^{2,7}$]dodeca-2(7),3,5,10-tetraene (1.5 g, 8.19 mmol) and N-methyl morpholine N-oxide (1.06 g, 9.03 mmol) were stirred in acetone (20 mL) and H$_2$O (0.16 mL). To this was added a solution of osmiom tetraoxide (OSO$_4$) (0.2 mL, 2.5%wt. soln. in t-butanol (t-BuOH), 0.02 mmol). After 2 hours, the mixture was diluted with EtOAc (50 mL) and washed with 10%aq. NaHSO$_3$ soln. (30 mL), H$_2$O (2×30 mL), sat. aq. NaHCO$_3$ soln. (30 mL) and brine (30 mL). The organic layer was dried (MgSO$_4$), filtered and evaporated to an oil (1.79 g, 99%). (TLC 50%EtOAc/hexanes R$_f$ 0.20).

H) 11-Benzyl-6methoxy-11-aza-tricyclo[7.3.1.0$^{2,7}$]trideca-2(7),3,5-triene hydrochloride (For a discussion of oxidative cleavage with Pb(OAC$_4$), see: Fieser and Fieser, *Reagents for Organic Synthesis,* (N.Y.) 1967, I, p.549. For reductive amination conditions and references, see Abdel-Magid et al. ,*J. Org. Chem.,* 1996, 61, 3849; and Mazzocchi et al., *J. Med. Chem.,* 1979, 22, 455.)

1-Methoxy-6,7,8,9-tetrahydro-5H-5,8-methano-benzocycloheptene-6,7-diol (2.40 g, 11.0 mmol) was stirred at 0° C. in CH$_2$Cl$_2$ (70 mL) and treated with Pb(OAc)$_4$ (5.08 g, 11.5 mmol). After 2 hours the mixture was filtered through a Celite pad and rinsed with CH$_2$Cl$_2$ (10 mL). To the stirred filtrate was added acetic acid (AcOH) (1.97 g, 33.0 mmol) and benzyl amine (1.23 g, 11.5 mmol). After 15 min., the mixture was treated with sodium triacetoxyborohydride (NaBH(OAc)$_3$) (8.94 g, 33.0 mmol) and stirred for 18 hours. The mixture was poured into a sat. aq. NaHCO$_3$ soln. (100 mL) and stirred for ½ hour. The layers were separated and extracted with CH$_2$Cl$_2$ (2×50 mL). The organic layer was washed with a saturated (sat.) aqueous (aq.) sodium bicarbonate (NaHCO$_3$) soln. (2×50 mL), H$_2$O (50 mL), brine (50 mL), dried through a cotton plug, concentrated and purified by chromatography on Silica gel eluting with 10%EtOAc/hexanes to provide product as an oil (1.45 g, 45%). (TLC 25%EtOAc/hexanes R$_f$ 0.76). $^1$H NMR (CDCl$_3$) δ7.12 (m, 4H), 6.89 (m, 2H), 6.74 (d, J=8.0 Hz, 1H), 6.64 (d, J=8.0 Hz, 1H), 3.87 (s, 3H), 3.41 (AB d, J=14.2 Hz, 1H), 3.38 (AB d, J=14.2 Hz, 1H), 2.87–2.70 (m, 5H), 2.38–2.23 (m, 3H), 1.85 (br AB d, J=12.1 Hz, 1H), 1.77 (br AB d, J=12.1 Hz, 1H). This oil was dissolved in a minimum of methanol (MeOH), stirred, and saturated with Et$_2$O. After 18 hours the white solids were filtered. $^1$H NMR (CD$_3$OD) δ7.44 (m, 5H), 7.15 (t, J=8.0 Hz, 1H), 6.85 (d, J=8.0 Hz, 1H), 6.68 (d, J=8.0 Hz, 1H), 4.27 (AB d, J=13.0 Hz, 1H), 4.15 (AB d, J=13.0 Hz, 1H), 3.84 (s, 3H), 3.47 (br d, J=12.3 Hz, 1H), 3.36–3.19 (m, 4H), 2.98 (AB dd, J=18.7,7.2 Hz, 1H), 2.85 (AB d, J=18.7 Hz, 1H), 2.60 (brs, 1H), 2.00 (AB d, J=13.0 Hz, 1H), 1.87 (AB d, J=13.0 Hz, 1H). mp 210–212° C.

EXAMPLE 3

6-METHOXY-11-AZA-TRICYCLO[7.3.1.0$^{2,7}$] TRIDECA-2(7),3,5-TRIENE HYDROCHLORIDE

11-Benzyl-6-methoxy-11-aza-tricyclo[7.3.1.0$^{2,7}$]trideca-2(7),3,5-triene hydrochloride (525 mg, 1.64 mmol), ammonium formate (2.07 g, 32.0 mmol and 10% palladium hydroxide on carbon (Pd(OH)$_2$/C) (200 mg) were combined in MeOH (30 mL) and refluxed for 2 hours. The mixture was filtered hot through Celite and the filtrate concentrated then azeotroped from MeOH (5×50 mL) to yield a solid. This was recrystallized from MeOH/Et$_2$O to provide a white solid (306 mg, 81%). $^1$H NMR (free base, CDCl$_3$) δ7.15 (t, J=8.0 Hz, 1H), 6.74 (d, J=8.0 Hz, 1H), 6.63 (d, J=8.0 Hz, 1H), 3.82 (s, 3H), 3.34 (br d, J=13.0 Hz, 1H), 3.11–3.02 (m, 4H), 2.94 (AB d, J=18.3 Hz, 1H), 2.87 (AB dd, J=18.3,6.5 Hz, 1H), 2.41 (br s, 1H), 1.91 (AB q, 2H). GSMS m/e 203 (M$^+$). mp 272–274° C.

EXAMPLE 4

11-AZA-TRICYCLO[7.3.1.0$^{2,7}$]TRIDECA-2(7),3,5-TRIEN-6-OL

6-Methoxy-11-aza-tricyclo[7.3.1.0$^{2,7}$]trideca-2(7),3,5-triene hydrochloride (55 mg, 0.23 mmol) was brought to reflux in 48% aq. hydrobronic acid (HBr) (5 mL). After 1 hour the solution was cooled and poured into 1N aq. NaOH soln. adjusted to pH 10 and product was extracted with EtOAc (3×40 mL). The organic layer was washed with brine (50 mL), dried (MgSO$_4$) and concentrated to a white solid, which was recrystallized from EtOAc/hexanes (20 mg, 46%). $^1$H NMR (CDCl$_3$) δ6.95 (t, J=8.0 Hz, 1H), 6.68 (d, J=8.0 Hz, 1H), 6.53 (d, J=8.0 Hz, 1H), 3.27 (m, 1H), 3.11 (m, 2H), 3.02 (m, 2H), 2.77 (m, 1H), 2.57 (m, 1H), 2.33 (br s, 1H), 1.90 (m, 2H). mp 106–108° C.

EXAMPLE 5

6-FLUORO-11-AZA-TRICYCLO[7.3.1.0$^{2,7}$] TRIDECA-2(7),3,5-TRIENE HYDROCHLORIDE

3-Fluoromethoxybenzene (15.8 g, 125 mmol) was stirred at -78° C. in anh. THF (100 mL) and treated with n-BuLi (50 mL, 2.5M hexanes soln., 125 mmol) over 5 min. After stirring below -70° C. for 4 hours, the mixture was treated with cyclopent-3-enecarboxylic acid methoxy-methyl-amide (18.4 g, 119 mmol) dropwise over ~¼ hour. The mixture was stirred below -70° C. for 1 hour, and then allowed to warm to ambient temperature over ~1 hour. The mixture was poured into 1N aq. HCl soln. (200 mL) and shaken. The layers were separated and the aq. layer extracted with EtOAc (3×100 mL). The organic layer was washed with H$_2$O (50 mL), sat. aq. NaHCK soln. (100 mL), and brine (50 mL), dried (Na$_2$SO$_4$), filtered through a Silica plug and concentrated to an oil (21.0 g, 76%). (TLC 30%EtOAc/hexanes R$_f$ 0.43). GCMS m/e 220 (M$^+$). This material was converted to the title compound by the methods described in Example 2C–G and Example 1G. (TLC 10%MeOH/CH$_2$Cl$_2$ (NH$_3$) R$_f$ 0.20). $^1$H NMR (CD$_3$OD) δ7.24 (m. 1H), 7.01 (m, 2H), 3.36 (d, J=13.0 Hz, 1H), 3.33–3.10 (m, 5H), 2.90 (d, J=18.5 Hz, 1H), 2.60 (m, 1H), 2.13 (AB d, J=13.0 Hz, 1H), 1.97 (AB d, J=13.0 Hz, 1H). mp 240–241° C.

EXAMPLE 6

11-BENZYL-5-METHOXY-11-AZA-TRICYCLO [7.3.1.0$^{2,7}$]TRIDECA-2(7),3,5-TRIENE HYDROCHLORIDE

A) Cyclopent-3-enyl-(2,5-dimethoxy-phenyl)methanone (For a discussion of halogen-metal exchange, see: Parham, W. E.: Bradsher, C. K. *Acc. Chem. Res.* 1982, 15, 300.)

2-Bromo-1,4-dimethoxy-benzene (42.2 g, 195 mmol) was stirred in $Et_2O$ (200 mL) under $N_2$ at −78° C. The resulting precipitate was dissolved by the addition of THF (50 mL). To the resulting solution was added n-BuLi (78 mL, 2.5M in hexanes, 195 mmol) over 10 min. After stirring 10 min., the yellow solution was treated with cyclopent-3-enecarboxylic acid methoxy-methyl-amide (29.15 9, 188 mmol) in $Et_2O$ (50 mL) over 10 min., then the mixture was stirred for 18 hours (the cooling bath evaporated overnight). The mixture was poured into 10% aq. HCl soln. (400 mL) and shaken. The layers were separated and the aq. layer extracted with $Et_2O$ (3×50 mL). The organic layer was washed with $H_2O$ (50 mL), a sat. aq. $NaHCO_3$ soln. (100 mL), dried ($Na_2SO_4$), filtered through a silica plug and concentrated to an oil (43.0 g, 99%). (In a separate experiment, THF was successfully substituted for $Et_2O$ in the reaction above.) (TLC 10%EtOAc/hexanes $R_f$ 0.39). $^1$H NMR (CDCl$_3$) δ7.16 (d, J=3.0 Hz, 1H), 6.98 (dd, J=9.0,3.0 Hz, 1H), 6.88 (d, J=9.0 Hz, 1H), 5.64 (br s, 2H), 4.11 (m, 1H), 3.84 (s, 3H), 3.77 (s, 3H), 2.66 (m, 4H).

B) Cyclopent-3-enyl-(2-hydroxy-5-methoxy-phenyl)-methanone

Cyclopent-3-enyl-(2,5-dimethoxy-phenyl)-methanone (40.0 g, 172 mmol) was converted to the title compound as described in Example 2C to provide an oil (39.5 g, crude). (TLC 10%EtOAc/hexanes $R_f$ 0.50). $^1$H NMR (CDCl$_3$) δ7.21 (m, 1H), 7.10 (m, 1H), 6.93 (br d, J=9.0 Hz, 1H), 5.69 (br s, 2H), 4.06 m, 1H), 3.79 (s, 3H), 2.76 (m, 4H). GCMS m/e 218 (M$^+$).

C) Trifluoro-methanesulfonic acid 2-(cyclopent-3-enecarbonyl)-4-methoxy-phenyl ester Cyclopent-3-enyl-(2-hydroxy-5-methoxy-phenyl)-methanone (39.5 g crude, 172 mmol) and pyridine (28.7 g, 362 mmol) were stirred in $CH_2Cl_2$ (300 mL) at −78° C. under $N_2$. To this a solution trifluommethane sulfonic anhydride (63.8 g, 226 mmol) in $CH_2Cl_2$ (100 mL) was added dropwise over ½ hour. The mixture was allowed to warm to ambient temperature and stirred 1 h then poured into a 1N aq. HCl soln. (250 mL). The mixture was shaken, the layers were separated, and the organic layer was washed with a 1N aq. HCl soln. (3×150 mL), $H_2O$ (2×100 mL), a sat. aq. $NaHCO_3$ soln. (100 mL) and, finally, brine (100 mL). The organic layer was dried through a cotton plug and concentrated to an oil which was chromatographed through a Silica gel plug eluting with 10%EtOAc/hexanes to afford after concentration an oil (55.7 g, 93% over 2 steps). GCMS m/e 350 (M$^{30}$ ).

D) 5-Methoxytriciclo[7.2.1.$^{2,7}$]dodeca-2(7),3.5.10-tetraene-8-one

Trifluoro-methanesulfonic acid 2-(cyclopent-3-enecarbonyl)methoxy-phenyl ester (19.09 g, 54.5 mmol) was dissolved in DMF (100 mL) under a $N_2$ atmosphere and treated with diisopropylethylamine (10.6 g, 82.0 mmol), potassium acetate (1.07 g, 11.0 mmol) and 1,3-bis (diphenylphosphino)propane (2.25 g, 5.46 mmol). This mixture was stirred and degassed (3 vacuurn/$N_2$ purge cycles) then treated with palladium acetate (0.49 g, 2.18 mmol). After stirring 20 min. the mixture was warmed to 120° C. for 18 hours, cooled and poured into brine (300 mL). The resulting mixture was extracted with EtOAc (4×100 mL) and the combined organic layer was washed with a sat. aq. $NaHCO_3$ soln. (100 mL), $H_2O$ (100 mL), brine (100 mL), dried (MgSO$_4$), filtered, concentrated and chromatographed on silica gel to provide an oil (10.4 g, 95%). (elute wt 7%EtOAc/hexanes). $^1$H NMR (CDCl$_3$) δ7.41 (d, J=2.8 Hz, 1H), 7.03 (d, J=8.0 Hz, 1H), 6.88 (dd, J=8.0,2.8 Hz, 1H), 6.72 (dd, J=5.2,3.0 Hz,1H), 6.06 (dd, J=5.2,3.2 Hz, 1H), 3.77 (s, 3H), 3.60 (dd, J=4.3,3.2 Hz, 1H), 3.44 (dd, J=5.0,3.4 Hz, 1H), 2.65 (AB m, 1H), 2.56 (br AB d, J=10.5 Hz, 1H). $^{13}$C NMR (CDCl$_3$) 196.11, 158.87, 145.90, 140.34, 130.295, 129.94, 126.14, 119.42, 111.90, 55.61, 55.48, 49.08,45.97. GCMS m/e 200 (M$^+$).

E) 5-Methoxytricyclo[7.2.1.0$^{2,7}$]dodeca-2(7),3.5.10-tetraene

5-Methoxytricyclo[7.2.1.0$^{2,7}$]dodeca-2(7),3,5,10-tetraene-8-one (9.41 g, 47 mmol) and pulverized potassium hydroxide (KOH) (6.17 g, 110 mmol) were warmed in ethylene glycol (50 mL) until solution occurred. The mixture was cooled to rt, treated with hydrazine hydrate (6 mL, 190 mmol) and heated to reflux for 2 hours. The reflux condenser was replaced with a distilling head and distillates were collected from 120–190° C. The distillates were diluted with $H_2O$ (100 mL) and extracted with EtOAc (4×40 mL). The organic layer was washed with $H_2O$ (4×30 mL), brine (25 mL), dried (MgSO$_4$), filtered and concentrated to an oil (8.2 g, 94%). (TLC 25%EtOAc/hexanes $R_f$ 0.68). $^1$H NMR (CDCl$_3$) δ6.92 (d, J=8.0 Hz, 1H), 6.88 (m, 2H), 6.25 (dd, J=5.1,2.5 Hz, 1H), 5.79 (dd, J=5.1,2.4 Hz, 1H), 3.77 (s, 3H), 3.31 (br s, 1H), 3.01–2.94 (2H), 2.56 (d, J=16.5 Hz, 1H), 2.22 (m, 1H), 1.85 (d, J=10.0 Hz, 1H). GCMS m/e 186 (M$^+$).

F) 5Methoxy-10,11 -dihydroxytricyclo[7.2.1.0$^{2,7}$]dodeca-2(7),3,5,10-triene

5-Methoxytricyclo[7.2.1.0$^{2,7}$]dodeca-2(7),3,5,10-tetraene (6.66 g, 35.7 mmol) was converted to the title compound as described in Example 2G to provide an oil (7.86 g, 100%). (TLC 10%MeOH/CH$_2$Cl$_2$ $R_f$ 0.44). $^1$H NMR (CDCl$_3$) δ6.95 (d, J=8.0 Hz, 1H), 6.63 (dd, J=8.0,2.5 Hz, 1H), 6.56 (br s, 1H), 4.00 (s, 3H), 3.77 (m, 3H), 3.04–2.99 (m, 2H), 2.69 (d, J=13.0 Hz, 1H), 2.41 (brs, 1H), 2.33 (brs, 1H), 2.22 (m, 1H), 1.52 (d, J=11.5 Hz, 1H).

G) 11-Benzyl-5-methoxy-11-aza-tricyclo[7.3.1.0$^{2,7}$]trideca-2(7),3,5-triene hydrochloride 5-Methoxy-10,11-dihydroxytricyclo[7.2.1.0$^{2,7}$]dodeca-2 (7),3,5,10-triene (18.0 g, 79.0 mmol) was stirred at 0° C. in $CH_2Cl_2$ (150 mL) and treated with lead tetraacetate (Pb (OAc)$_4$) (35.0 9, 79.0 mmol). After 30 min. the mixture was filtered through a Celite pad and rinsed with $CH_2Cl_2$ (50 mL). To the stirred filtrate was added ACOH (23.7 g, 395 mmol) and benzyl amine (8.50 g, 79.0 mmol). After 15 min., the mixture was treated with NaBH(OAc)$_3$ (50.2 g, 237 mmol) and stirred for 18 hours. The mixture was poured into a sat. aq. $Na_2CO_3$ soln. (100 mL) stirred for ½ hour. The layers were separated and extracted with $CH_2Cl_2$ (2×100 mL). The organic layer was washed with a sat. aq. $Na_2CO_3$ soln. (2×50 mL), $H_2O$ (50 mL), and then brine (50 mL), dried through a cotton plug and concentrated to an oil. Chromatography on silica gel eluting with 5%EtOAc/hexanes provided product as an oil (9.48 g, 41%). (TLC 25%EtOAc/hexanes $R_f$ 0.69). $^1$H NMR (CDCl$_3$) δ7.15 (m, 3H), 6.92 (m, 3H), 6.71 (br s, 1H), 6.67 (dd, J=8.0,2.5 Hz, 1H), 3.83 (s, 3H), 3.99 (s, 2H), 3.07 (AB dd, J=17.5,7.0 Hz, 1H), 2.85 (br s, 1H), 2.83 (m, 1H), 2.79 (AB d, J=17.5 Hz, 1H), 2.70 (br d, J=10.5 Hz, 1H), 2.35 (dd, J=10.5,2.0 Hz, 1H), 2.27 (dd, J=10.2,2.0 Hz, 1H), 2.15 (br s, 1H), 1.86 (AB d, J=12.3 Hz, 1H), 1.78 (AB d, J=12.3 Hz, 1H). GCMS m/e 293 (M+). This material was dissolved in excess 1N HCl MeOH and concentrated. The solids were dissolved in a minimum of MeOH, stirred, and saturated with $Et_2O$. After stirring 18 h the white solids were filtered (900 mg, 58%). $^1$H NMR ($CD_3OD$) δ7.40 (m, 5H), 7.00 (d, J=8.0 Hz, 1H), 6.73 (m, 2H), 4.28 (AB d, J=13.5 Hz, 1H), 4.16 (AB d, J=13.5 Hz, 1H), 3.76 (s, 3H), 3.48 (br d, J=12.0 Hz, 1H), 3.35–3.20 (m, 5H), 2.98 (AB d, J=18.4 Hz, 1H), 2.54 (brs, 1H), 2.01 (AB d, J=12.0 Hz, 1H), 1.89 (AB d, J=12.0 Hz, 1H). mp 233–234° C.

EXAMPLE 7

11-BENZYL-11-AZA-TRICYCLO[7.3.1.0$^{2,7}$]TRIDECA-2(7),3,5-TRIEN-5-OL HYDROCHLORIDE

11-Benzy-5-methoxy-11-aza-tricycto[7.3.1.0$^{2,7}$]trideca-2(7),3,5-triene (203 mg, 0.62 mmol) was brought to reflux in 48%HBr (5 mL). After 1 hour the solution was cooled and poured into an aq. $NH_4OH$ soln., the pH was adjusted to ~9 and the product was extracted with EtOAc (3×40 mL). The organic layer was washed with brine (50 mL), dried ($MgSO_4$) and concentrated to an oil. (TLC 25%EtOAc/hexanes ($NH_3$) $R_f$ 0.37). This material was dissolved in excess 1N HCl in MeOH and concentrated. Recrystallization from MeOH/$Et_2O$ provided a solid (154 mg, 80%). $^1$H NMR ($CDCl_3$) δ7.42 (m, 5H), 6.90 (d, J=8.0 Hz, 1H), 6.60 (m, 2H), 4.27 (AB d, J=13.0 Hz, 1H), 4.15 (AB d, J=13.0 Hz, 1H), 3.47 (d, J=12.2 Hz, 1H), 3.33–3.15 (5H), 2.86 (d, J=18.0 Hz, 1H), 2.52 (br s, 1H), 1.99 (AB d, J=12.5 Hz, 1H), 1.88 (AB d, J=12.5 Hz, 1H). mp 251–253° C.

EXAMPLE 8

5-METHOXY-11-AZA-TRICYCLO[7.3.1.0$^{2,7}$]TRIDECA-2(7),3,5-TRIENE HYDROCHLORIDE

11-Benzyl-5-methoxy-11-aza-tricyclo[7.3.1.0$^{2,7}$]trideca-2(7),3,5-triene hydrochloride (206 mg, 0.63 mmol) was converted to the title compound by the method described in Example 3 to provide a white solid (122 mg, 81%). (TLC 10 %MeOH/$CH_2Cl_2$ ($NH_3$) $R_f$ 0.48). $^1$H NMR ($CD_3OD$) δ7.08 (d, J=8.0 Hz, 1H), 6.77 (m, 2H), 3.76 (s, 3H), 3.31–3.12 (m, 6H), 2.98 (AB d, J=18.4 Hz, 1H), 2.43 (br s, 1H), 2.10 (AB d, J=13.0 Hz, 1H), 1.94 (AB d, J=13.0 Hz, 1H). GSMS m/e 203 (M+). mp 253.5–256° C.

EXAMPLE 9

11-AZA-TRICYCLO[7.3.1.0$^{2,7}$]TRIDECA-2(7),3,5-TRIEN-5-OL HYDROCHLORIDE

5-Methoxy-11-aza-tricyclo[7.3.1.0$^{2,7}$]trideca-2(7),3,5-triene hydrochloride (187 mg, 0.78 mmol) was brought to reflux in 48%HBr (5 mL). After 1 hour the solution was cooled and poured into aq. $NH_4OH$ soln., the pH was adjusted to ~9 and the product was extracted with EtOAc (3×40 mL). The organic layer was washed with brine (50 mL), dried ($MgSO_4$) and concentrated to a solid. (TLC 10%MeOH/$CH_2Cl_2$ ($NH_3$) $R_f$ 0.13). This material was dissolved in excess 1N HCl MeOH and concentrated. Recrystallization from MeOH/$Et_2O$ provided a solid (70 mg, 40%). $^1$H NMR ($CD_3OD$) δ6.99 (d, J=8.0 Hz, 1H), 6.63 (m, 2H), 3.48–3.11 (6H), 2.83 (d, J=18.0 Hz, 1H), 2.42 (br s, 1H), 2.08 (AB d, J=12.5 Hz, 1H), 1.93 (AB d, J=12.5 Hz, 1H). mp 295–298° C.

EXAMPLE 10

11-BENZYL-5-DIFLUOROMETHOXY-11-AZA-TRICYCLO[7.3.1.0$^{2,7}$]TRIDECA-2(7),3,5-TRIENE
(For leading references, see: Langlois, B. R. *J. Fluorine Chem.* 1988, 41, 247–262.)

11-Benzyl-11-aza-tricyclo[7.3.1.0$^{2,7}$]trideca-2(7),3,5-trien-5-ol (572 mg, 2.05 mmol) was stirred in dioxane (5 mL) and $H_2O$ (1 mL) at reflux under a balloon of freon ($HCF_2Cl$). To this was added 3N KOH dropwise so as to maintain a pH~12. The consumption of starting material was monitored by TLC for over 2 hours. The reaction was cooled, diluted with $H_2O$ (40 mL) and extracted with EtOAc. The organic layer was washed with a sat. aq. $Na_2CO_3$ soln. (25 mL) and brine (25 mL), dried ($MgSO_2$), filtered and concentrated to an oil (620 mg, 92%). GCMS m/e 329 (M+).

EXAMPLE 11

5-DIFLUOROMETHOXY-11-AZA-TRICYCLO[7.3.1.0$^{2,7}$]TRIDECA-2(7),3,5-TRIENE HYDROCHLORIDE

11-Benzyl-5-difluoromethoxy-11-aza-tricyclo[7.3.1.0$^{2,7}$]trideca-2(7),3,5-triene (620 mg, 1.88 mmol) was converted to the title compound as described in Example 3. The HCl salt was generated as in Example 9 to provide product as a white powder (280 mg, 54%). $^1$H NMR ($CDCl_3$) δ7.42 (m, 5H), 7.01 (d, J=9.0 Hz, 1H), 6.92 (m, 2H), 6.48 (t, J=74 Hz, 1H), 3.37 (d, J=13.0 Hz, 1H), 3.18–3.04 (6H), 2.39 (brs, 1H), 1.95 (brs, 2H). GCMS m/e 239 (M+). mp 230–234° C.

EXAMPLE 12

11-BENZYL-5-ETHXOY-11-AZA-TRICYCLO[7.3.1.0$^{2,7}$]TRIDECA-2(7),3,5-TRIENE HYDROCHLORIDE (For a review, see: Mitsunobu, O. *Synthesis,* 1981, 1.)

11-Benzyl-11-aza-tricyclo[7.3.1.0$^{2,7}$]trideca-2(7),3,5-trien-5-ol (208 mg, 0.75 mmol), ethanol (69 mg, 1.49 mmol) and triphenylphosphine (391 mg, 1.49 mmol) were stirred under $N_2$ at 0° C. in THF (2.5 mL). To this was added diethylazodicarboxylate (259 mg, 1.49 mmol) dropwise. After 18 hours, the reaction was concentrated, diluted with $Et_2O$ (20 mL) and extracted with 1% aq. phosphoric acid ($H_3PO_4$) soln. (3×20 mL). The combined aq. layer was extracted with $Et_2O$ (10 mL) and then basified to pH 10 with 1N NaOH soln. Product was extracted with EtOAc (3×20 mL) and the combined organic layer was washed with 1N NaOH soln. (20 mL) and brine (20 mL). The solution was dried ($MgSO_4$), filtered and evaporated to an oil (170 mg, 74%). (TLC 17%EtOAc/hexanes ($NH_3$) $R_f$ 0.76). $^1$H NMR ($CDCl_3$) δ7.12 (m, 3H), 6.91 (m, 2H), 6.86 (d, J=8.0 Hz, 1H), 6.68 (br s, 1H), 6.63 (dd, J=8.0,2.5 Hz, 1H), 4.03 (q, 2H), 3.37 (br s, 2H), 3.03 (dd, J=17.0,7.0 Hz, 1H), 2.8–2.68 (4H), 2.18 (2H), 2.12 (br s, 1H), 1.83 (AB d, J=12.0 Hz, 1H), 1.75 (AB d, J=12.0 Hz, 1H), 1.43 (t, J=7.0 Hz, 3H). GCMS m/e 307 (M+). This material was dissolved in excess 1N HCl MeOH and concentrated. Recrystallization from $CH_2Cl_2$/$Et_2O$ provided a solid (185 mg, 97%). mp 200–203° C.

EXAMPLE 13

5-ETHOXY-11-AZA-TRICYCLO[7.3.1.0$^{2,7}$]TRIDECA-2(7),3.5-TRIENE HYDROCHLORIDE

11-Benzyl-5-Ethoxy-11-aza-tricyclo[7.3.1.0$^{2,7}$]trideca-2(7),3,5-triene hydrochloride (160 mg, mmol), ammonium formate (220 mg, 3.49 mmol) and 10%Pd(OH)$_2$/C (100 mg) were combined in methanol (MeOH) (5 mL) and warmed to reflux for 15 min. The mixture was cooled, filtered, concentrated, diluted with sat. aq. Na$_2$CO$_2$ soln. and extracted with EtOAc (3×20 mL). The extracts were dried (MgSO$_4$), filtered and concentrated to an oil (94 mg, 83%). (TLC 50%EtOAc/hexanes (NH$_3$) R$_f$ 0.20). $^1$H NMR (CDCl$_3$) δ6.90 (d, J=9.0 Hz, 1H), 6.66 (2H), 3.97 (m, 2H), 3.08 (dd, J=18.0,6.0 Hz, 1H), 2.94 (m, 3H), 2.76–2.65 (3H), 1.96 (m, 2H), 1.88 (d, J=11.0 Hz, 1H), 1.38 (t, J=7.0 Hz, 3H). This material was dissolved in excess 1N HCl MeOH and concentrated. Recrystallization from CH$_2$Cl$_2$/Et$_2$O provided a solid (74 mg, 68%). mp 243–245° C.

EXAMPLE 14

5-SOPROPOXY-11-AZA-TRICYCLO[7.3.1.0$^{2,7}$] TRIDECA-2(7),3,5-TRIENE HYDROCHLORIDE

11-Benzyl-11-aza-tricyclo[7.3.1.0$^{2,7}$]trideca-2(7),3,5-trien-5-ol (208 mg, 0.75 mmol) and isopropyl alcohol (90 mg, 1.49 mmol) were converted to the title compound as described in Examples 12. (TLC of intermediate benzyl compound, 17%EtOAc/hexanes R$_f$ 0.78). GCMS m/e 321 (M$^+$). Deprotection and conversion to the salt as described in Example 13 provided a solid (83 mg, 42% overall). (TLC of title compound, TLC 50%EtOAc/hexanes (NH$_3$) R$_f$ 0.10). $^1$H NMR (CDCl$_3$) δ$^1$H NMR (CDCl$_3$) δ6.89 (d, J=9.0 Hz, 1H), 6.66 (2H), 4.51 (m, 1H), 3.08 (dd, J=18.0,6.5 Hz, 1H), 2.98 (m, 3H), 2.78–2.68 (3H), 1.96 (m, 2H), 1.87 (d, J=11.0 Hz, 1H), 1.32 (t, J=5.5 Hz, 6H). mp 211–213° C.

EXAMPLE 15

11-BENZYL-4-METHOXY-11-AZA-TRICYCLO [7.3.1.0$^{2,7}$]TRIDECA-2(7),3,5-TRIENE HYDROCHLORIDE

A) 2-Cyclopent-3-enylmethyl-5-methoxy-phenol (For leading references, see: a) Nagata, W.; Okada, K.; Aoki, T. *Synthesis* 1979, 365–368; b) Lau, C. K.; Williams, H. W. R.; Tardiff, S.; Dufresne, C.; Scheigetz, J.; Belanger, P, C. *Can. J. Chem.* 1989, 67,1384–1387.)

3-Methoxyphenol (5.12 g, 42.0 mmol), cyclopent-3-enecarbaldehyde (8.00 g, 83.0 mmol), phenyl boronic acid (5.58 g, 43 mmol) and 1,1,1-trichloroacetic acid (2.04 a, 12.5 mmol) were refluxed in benzene (150 mL) for 18 hours. (TLC 5%CH$_2$C$_2$/hexanes R$_f$ 0.47). The mixture was concentrated to an oil which was stirred at 0° C. in CH$_2$Cl$_2$ (100 mL) and treated with triethylsilane (8.87 g, 76.0 mmol) followed by trifluoroacetic acid (36.3 g, 318 mmol). The mixture was stirred for 1 hour then warmed to reflux for 24 hours. The mixture was concentrated, dissolved in CH$_2$Cl$_2$ (200 mL) and washed with a sat. aq. NaHCO$_3$ soln. (3×50 mL). The combined organic layer was dried through a carbon plug, concentrated and chromatographed on silica gel to provide an oil (3.85 g, 45%). (TLC 10%EtOAc/hexanes R$_f$ 0.35). $^1$H NMR (CDCl$_3$) δ6.99 (d, J=8.0 Hz, 1H), 6.42 (dd, J=8.0,2.5 Hz, 1H), 6.36 (d, J=2.5 Hz, 1H), 5.67 (br s, 2H), 3.75 (s, 3H), 2.58 (m, 3H), 2.40 (m, 2H), 2.08 (m, 2H), GCMS m/e 204 (M$^+$).

B) Trifluoro-methanesulfonic acid 2-cyclopent-3-enylmethyl-5-methoxy-phenyl ester 2-Cyclopent-3-enylmethyl-5-methoxy-phenol (3.85 g, 19.0 mmol) was converted to the title compound (4.92 g, 77%) by the method described in Example 1D. (TLC 10%CH$_2$Cl$_2$/hexanes R$_f$ 0.52). $^1$H NMR (CDCl$_3$) δ7.21 (d, J=8.0 Hz, 1H), 6.86 (dd, J=8.0,25 Hz, 1H), 6.79 (d, J=2.5 Hz, 1H), 5.67 (br s, 2H), 3.79 (s, 3H), 2.70 (d, J=7.5 Hz, 2H), 2.59 (m, 1H), 2.43 (m, 2H), 2.03 (m, 2H).

C) 4-Methoxytricyclo[7.2.1.0$^{2,7}$]dodeca-2(7),3,5,10-tetraene

Trifluoro-methanesulfonic acid 2-cyclopent-3-enylmethyl-5-methoxy-phenyl ester (2.00 g, 5.95 mmol) was dissolved in DMF (10 mL) under a N$_2$ atmosphere and treated with triethylamine (0.91 g, 8.92 mmol) and 1,3-bis (diphenylphosphino)propane (0.37 g, 0.89 mmol). This mixture was stirred and degassed (3 vacuum/N$_2$ purge cycles), and then treated with palladium acetate (93 mg, 0.42 mmol). After stirring for 20 min. the mixture was warmed to 100° C. for 18 hours, cooled and poured into brine (30 mL). The resulting mixture was extracted with EtOAc (4×10 mL) and the combined organic layer was washed with sat. aq. NaHCO$_3$ soln. (10 mL), H$_2$O (10 mL), brine (10 mL), dried (MgSO$_4$), filtered and evaporated to an oil. The oil was chromatographed on Silica gel (2%CH$_2$Cl$_2$/hexanes) to provide product as an oil (1.05 g, 95%). (TLC 10%EtOAc/ hexanes R$_f$ 0.52). $^1$H NMR (CDCl$_3$) δ6.94 (d, J=8.0 Hz, 1H), 6.68 (dd, J=8.0,2.8 Hz, 1H), 6.59 (d, J=2.8 Hz, 1H), 6.23 (dd, J=5.5,2.8 Hz,1H), 5.79 (dd, J=5.5,2.6 Hz, 1H), 3.77 (s, 3H), 3.28 (m, 1H), 2.96–2,89 (m, 2H), 2.49 (d, J=15.5 Hz, 1H), 2.19 (m, 1H), 1.85 (d, J=10.5 Hz, 1H). $^{13}$C NMR (CDCl$_3$) 156.94, 144.07, 138.95, 131.24, 131.21, 126.34, 111.73, 111.45, 55.22, 45.10, 40.18, 38.47, 29.49. GCMS m/e 186 (M$^+$).

D) 11-Benzyl-4-methoxy-11-aza-tricyclo[7.3.1.0$^{2,7}$] trideca-2(7),3.5-triene hydrochloride 4Methoxytricylo[7.2.1.0$^{2,7}$]dodeca-2(7),3,5,10-tetraene (1.0 g, 5.37 mmol) was converted to 4-methoxy-10,11-dihydroxytricyclo[7.2.1.0$^{2,7}$]dodeca-2(7),3,5,10-triene (0.95 g, 80%) (TLC 50%EtOAc/CH$_2$Cl$_2$ R$_f$ 0.46) according to the procedure described in Example 2G. This material was converted to the title compound according to the procedures described in Example 2H with final recrystallization from Et$_2$O/hexanes (650 mg, 46%). (TLC 50%EtOAc/CH$_2$Cl$_2$ R$_f$ 0.67). $^1$H NMR (CDC$_3$OD) δ7.42 (m, 5H), 7.12 (d, J=8.0 Hz, 1H), 6.84 (dd, J=8.0,2.5 Hz, 1H), 6.67 (d, J=2.5 Hz, 1H), 4.27 (AB d, J=13.0 Hz, 1H), 4.17 (AB d, J=13.0 Hz, 1H), 3.72 (s, 3H), 3.48 (br d , J=12.5 Hz, 1H), 3.34–3.16 (m, 5H), 2.86 (AB d, J=18.0 Hz, 1H), 2.55 (brs, 1H), 2.00 (AB d, J=13.0 Hz, 1H), 1.90 (AB d, J=13.0 Hz, 1H). mp 245–246° C.

EXAMPLE 16

4-METHOXY-11-AZA-TRICYCLO[7.3.1.0$^{2,7}$] TRIDECA-2(7),3,5-TRIENE HYDROCHLORIDE

11-Benzyl-4-methoxy-11-aza-trcyclo[7.3.1.0$^{2,7}$]trideca-2 (7),3,5-triene hydrochloride (525 mg, 1.60 mmol) was converted to the title compound by the methods described in Example 3 to provide a white solid (336 mg, 88%). (TLC 40%EtOAc/CH$_2$Cl$_2$ (NH$_3$) R$_f$ 0.22). $^1$H NMR (CD$_3$OD) δ7.11 (d, J=8.5 Hz, 1H), 6.82 (dd, J=8.5,2.5 Hz, 1H), 6.75 (d, J=2.5 Hz, 1H), 3.76 (s, 3H), 3.34–3.16 (m, 6H), 2.86 (AB d, J=17.7Hz, 1H), 2.45 (m, 1H), 2.11 (AB d, J=13.5 Hz, 1H), 1.94 (AB d, J=13.5 Hz, 1H). $^{13}$C NMR (CDCl$_3$) 158.47, 136.58, 130.15, 127.71, 114.11, 112.61, 54.32, 49.99, 49.47, 32.16, 31.97, 27.15, 25.70. mp 259–261° C.

EXAMPLE 17

11-AZA-TRICYCLO[7.3.1.0$^{2,7}$]TRIDECA-2(7),3,5-TRIEN-4-OL

4-Methoxy-11-aza-tricyclo[7.3.1.0$^{2,7}$]trideca-2(7),3,5-triene hydrochloride (120 mg, 0.50 mmol) was brought to reflux in 48%HBr (2 mL). After 1 hour the solution was cooled and poured Into a 1N aq. NaOH soln. adjusted to pH 10 and product was extracted with EtOAc (3×40 mL). The organic layer was washed with brine (50 mL), dried ($MgSO_4$) and concentrated to a white solid which was recrystallized from $Et_2O$/hexanes (40 mg, 42%). (TLC 50%EtOAc/$CH_2Cl_2$ $R_f$ 0.15). $^1H$ NMR ($CDCl_3$) δ6.96 (d, J=8.0 Hz, 1H), 6.60 (dd, J=8.0,2.5 Hz, 1H), 6.46 (d, J=2.5 Hz, 1H), 3.31 (m, 1H), 3.03 (dd, J=17.0,6.0 Hz, 1H), 2.95 (m, 2H,NH), 2.73 (m, 3H), 1.99 (m, 2H), 1.87 (AB d, J=12.5 Hz, 1H). mp 215–217° C.

EXAMPLE 18

11-BENZYL-11-AZA-TRICYCLO[7.3.1.0$^{2,7}$] TRIDECA-2(7),3,5-TRIENE HYDROCHLORIDE

The title compound was prepared from phenol according to the procedures described in Example 15. (TLC 10%EtOAc/hexanes ($NH_3$) $R_f$ 0.76). $^1H$ NMR ($CD_3OD$) δ7.42 (m, 5H), 7.22 (m, 2H), 7.15 (t, J=7.5 Hz, 1H), 7.10 (t, J=7.5 Hz, 1H), 4.28 (AB d, J=13.0 Hz, 1H), 4.18 (AB d, J=13.0 Hz, 1H), 3.51 (d, J=12.8 Hz, 1H), 3.36 (d, J=13.2 Hz, 1H), 3.34–3.23 (m, 4H), 2.95 (d, J=12.2 Hz, 1H), 2.58 (m, 1H), 2.03 (AB d, J=13.0 Hz, 1H), 1.92 (AB d, J=13.0 Hz, 1H). mp 125–127° C.

EXAMPLE 19

11-AZA-TRICYCLO[7.3.1.0$^{2,7}$]TRIDECA-2(7),3,5-TRIENE HYDROCHLORIDE

11-Benzyl-11-aza-tricyclo[7.3.1.0$^{2,7}$]trideca-2(7),3,5-triene hydrochloride (150 mg, 0.50 mmol) was converted to the title compound as described in Example 3. (TLC 20%EtOAc/hexanes ($NH_3$) $R_f$ 0.20). $^1H$ NMR ($CD_3OD$) δ7.26–7.17 (m, 4H), 3.37–3.18 (m, 6H), 2.92 (d, J=18.2 Hz, 1H), 2.48 (m, 1H), 2.13 (AB d, J=13.0 Hz, 1H), 1.97 (AB d, J=13.0 Hz, 1H). $^{13}C$ NMR ($CDCl_3$) δ136.08, 135.67, 129.43, 128.78, 127.30, 126.42, 49.90, 49.05, 32.67, 31.86, 27.15, 25.60. mp 227–228° C.

EXAMPLE 20

4-NITRO-11-AZA-TRICYCLO[7.3.1.0$^{2,7}$] TRIDECA-2(7),3,5-TRIENE HYDROCHLORIDE

A) 1-(11-Aza-ticyclo[7.3.1.0$^{2,7}$]trideca-2(7),3,5-trien-11-yl)-2,2,2-trifluoro-ethanone 11-Aza-tricydo[7.3.1.0$^{2,7}$]trideca-2(7),3,5-triene (1.22 g, 7.08 mmol) was stirred at 0° C. in $CH_2Cl_2$ (10 mL) and treated with triethylamine (0.94 mL, 10.6 mmol followed by TFAA (1.90 mL, 14.2 mmol). After ~1 hour, the solution was poured into 0.5 N HCl (200 mL) and the layers separated. The aq. layer was extracted with $CH_2Cl_2$ (3×50 mL) and the combined organic layer was washed with 0.5 N HCl (50 mL), $H_2O$ (2×50 mL) and sat. aq. $NaHCO_3$ soln. (50 mL). This solution was dried through a cotton plug, then diluted with ~3% EtOAc and filtered through a 2 inch silica pad eluted with ~3% EtOAc/$CH_2Cl_2$. Concentration afforded a clear oil (1.90 g, 99%). $^1H$ NMR ($CDCl_3$) δ7.15–7.02 (4H), 4.67 (d, J=13.0 Hz, 1/2H), 4.42 (d, J=13.0 Hz, 1/2H), 4.03 (d, J=13.0 Hz, 1/2H), 3.81 (d, J=13.0 Hz, 1/2H), 3.44 (d, J=13.0 Hz, 1H), 3.29–2.99 (3H), (d, J=18.0 Hz, 1H), 2.37 (br s, 1/2H), 2.30 (br s, 1/2H), 2.04 (AB d, 2H). GCMS m/e 269 ($M^+$).

B) ~Nitro-11-aza-tricyclo[7.3.1.0$^{2,7}$]trideca-2(7),3,5-triene hydrochloride

The title compound was prepared as follows, based on the method described by Coon et al., *J. Org. Chem.,* 1973, 25, 4243. To a solution of trifluoromethanesulfonic acid (0.94 ml, 10.6 mmol) in $CH_2Cl_2$ (10 ml ) stirred at 0° C. was slowly added nitric acid (0.60 ml, 14.1 mmol) generating a white precipitate. After 10 minutes the resulting mixture was cooled to −78° C. and treated with 1-(11-aza-tricyclo [7.3.1.0$^{2,7}$]trideca-2(7),3,5-trien-11-yl)-2,2,2-trifluoro-ethanone (1.9 g, 7.06 mmol) in $CH_2Cl_2$ (15 ml) dropwise over 5 minutes. The reaction was stirred at −78° C. for 2 h then warmed to 0° C. for ½ hour. The reaction mixture was poured into a stirred ice (50 g). The layers were separated and the aq. layer back extracted with $CH_2Cl_2$ (3×30 ml). The organic layer was combined and washed with $H_2O$ (3 ×30 ml). The combined organic layer was washed with sat. aq. $NaHCO_3$ soln. (20 mL) and $H_2O$ (20 mL) then dried through a cotton plug and concentrated to a yellow solid (1.58 g) which contained four products (TLC). The solids were slurried in $Et_2O$ and filtered to provide a solid (900 mg, 41%). (TLC 30% EtOAc/hexanes, $R_f$ 0.21). The filtrate was chromatographed on Silica gel eluting with 30% EtOAc/hexanes to provide three materials. $R_f$ 0.32 (50 mg, 2%), $R_f$ 0.21 (as solids above) and $R_f$ 0.13 (50 mg, 2%). GCMS m/e 314 ($M^+$).

C) 4-Nitro-11 -aza-tricyclo[7.3.1 0$^{2,7}$]trideca-2(7),3, 5-triene hydrochloride NOE (Nuclear Overhauser Effect) experiments elucidated the primary product, (TLC 30%EtOAc/hexanes, $R_f$ 0.21) as 2,2,2-trifluoro-1-(4-nitro-11-aza-tricydo[7.3.1.0$^{2,7}$]trideca-2 (7),3,5-trien-11-yl)-ethanone, by a 4% NOE between H-3 and H-1. This solid (780 mg, 2.48 mmol) was stirred in MeOH (20 mL) and treated with $Na_2CO_3$ (650 mg, 4.96 mmol) in $H_2O$ (10 mL). The stirred mixture was warmed to 70° C. for 6 hours, concentrated to solids, diluted with $H_2O$ and extracted with $CH_2Cl_2$ (3×40 mL). The product was extracted into 1N aq. HCl soln. (3×40 mL) which was washed with EtOAc then neutralized with a sat. aq. $Na_2CO_3$ soln. to pH~10. Product was extracted with $CH_2Cl_2$ (3×40 mL), dried through a cotton plug, concentrated to an oil. The oil was dissolved in MeOH and treated with 3N HCl EtOAc (4 mL) and concentrated, then dissolved in a minimum of $CH_2Cl_2$ and the solution was saturated with hexanes and stirred 18 hours. The product was collected by filtration (145 mg, 23%). $^1H$ NMR ($DMSO_{d-6}$) d 8.12 (d, J=2.5 Hz, 1H), 8.09 (d, J=8.0 Hz, 1H), 7.50 (dd, J=8.0,2.5 Hz, 1H), 3.25 (m, 3H), 3.08 (m, 3H), 2.88 (m, 2H), 2.27 (m, 1H), 1.99 (d, J=11.0 Hz, 1H). GCMS m/e 218 ($M^+$). mp 215–220° C.

EXAMPLE 21

5-NITRO-11-AZA-TRICYCLO[7.3.1.0$^{2,7}$] TRIDECA-2(7),3,5-TRIENE HYDROCHLORIDE

The other meta substituted isomer from above, 2,2,2-trifluoro-1-(5-nitro-11-aza-tricyclo[7.3.1.0$^{2,7}$]trideca-2(7), 3,5-trien-11-yl)-ethanone (TLC 30%EtOAc/hexanes, $R_f$ 0.13) was converted to the title compound by the method in Example 20C. $^1H$ NMR free base ($CDCl_3$) δ8.01 (d, J=2.0 Hz, 1H), 7.95 (dd, J=8.0,2.0 Hz, 1H), 7.17 (d, J=8.0 Hz, 1H), 3.16 (dd, J=18.0,6.5 Hz, 1H), 3.10–2.97 (4H), 2.89 (d, J=18.0 Hz, 1H), 2.79 (d, J=12.0 Hz, 1H), 2.12 (m, 1H), 2.02 (d, J=12.5 Hz, 1H), 1.88 (d, J=12.5 Hz, 1H). Conversion to the salt as in Example 20C provides a solid mp 245–255° C.

EXAMPLE 22

3-NITRO-11-AZA-TRICYCLO[7.3.1.0$^{2,7}$] TRIDECA-2(7),3,5TRIENE HYDROCHLORIDE

The remaining isolated isomer from above, 2,2,2-trifluoro-1-(3-nitro-11-aza-tricyclo[7.3.1.0$^{2,7}$]trideca-2(7), 3,5-trien-11-yl)-ethanone (TLC 30%EtOAc/hexanes, $R_f$ 0.32) (50 mg) was converted to the title compound by the method in Example 20C to give 25 mg, 64%). The regiochemistry of this nitro isomer was established by HMQC (heteronuclear multiple-quantum correlation) between C-3 and H-1. $^1$H NMR (DMSO$_{d-6}$) δ7.80 (d, J=8.0 Hz, 1H), 7.53 (d, J=8.0 Hz, 1H), 7.45 (t, J=8.0 Hz, 1H), 3.71–3.15 (m, 6H), 2.95 (d, J=18.5 Hz, 1H), 2.40 (brs, 1H), 2.04 (d, J=12.5 Hz, 1H), 1.70 (d, J=12.5 Hz, 1H).

EXAMPLE 23

11-BENZYL-5FLUORO-11-AZA-TRICYCLO[7.3.1.0$^{2,7}$]TRIDECA-2(7),3,5-TRIENE HYDROCHLORIDE

The title compound was prepared from 2-bromo-4-fluoro-1-methoxy-benzene by the methods described in Example 6. $^1$H NMR (CD$_3$OD) δ7.15 (m, 3H), 6.94–6.76 (m, 5H), 3.40 (AB d, 2H), 3.06 (dd, J=17.5,7.0 Hz, 1H), 2.87–2.73 (3H), 2.69 (d, J=10.5 Hz, 1H), 2.37 (d, J=10.5 Hz, 1H), 2.28 (d, J=10.5 Hz, 1H), 2.17 (br s, 1H), 1.83 (AB d, 2H). GCMS m/e 281 (M$^+$). mp 202–203° C.

EXAMPLE 24

5-FLUORO-11-AZA-TRICYCLO[7.3.1.0$^{2,7}$]TRIDECA-2(7),3,5-TRIENE HYDROCHLORIDE

11-Benzyl-5-fluoro-11-aza-tricyclo[7.3.1.0$^{2,7}$]trideca-2(7), 3,5-triene hydrochloride (310 mg, 0.94 mmol) was converted to the title compound by the methods described in Example 3 to yield a white solid (140 mg, 65%). $^1$H NMR (CD$_3$OD) δ7.22 (m, 1H), 6.93 (m, 2H), 3.38–3.14 (6H), 2.93 (d, J=18.5 Hz, 1H), 2.45 (m, 1H), 2.17 (AB d, J=13.0 Hz, 1H), 1.94 (AB d, J=13.0 Hz, 1H). mp 286–287° C.

EXAMPLE 25

5,7-DIOXA-14-AZATETRACYCLO[10.3.1.0$^{2,10}$.0$^{4,8}$]HEXADECA-2(10),3,8-TRIENE HYDROCHLORIDE

5-Bromo-6-methoxy-benzo[1,3]dioxole (Preparation described previously, see; Getahun, Z.; Jurd, L.; Chu, P. S.; Lin, C. M.: Hamel, E. J. *Med. Chem.* 1992, 35, 1058–1087.) was converted to the title compound using methods described in Example 3 and Example 6 to yield a white solid (110 mg). $^1$H NMR (CD$_3$OD) δ6.65 (s, 2H), 5.88 (s, 2H), 3.33–3.12 (6H), 2.81 (d, J=18.0 Hz, 1H), 2.42 (m, 1H), 2.09 (AB d, J=12.5 Hz, 1H), 1.90 (AB d, J=12.5 Hz, 1H). GCMS m/e 217 (M$^+$). APCI MS m/e 218.1 [(M+1)$^+$]. mp 241–243° C.

EXAMPLE 26

11-BENZYL-6-BROMO-5-METHOXY-11-AZA-TRICYCLO[7.3.1.0$^{2,7}$]TRIDECA-2(7),3,5-TRIENE

11-Benzyl5-methoxy-11-aza-tricyclo[7.3.1.0$^{2,7}$]trideca-2(7), 3,5 -triene (3.00 g, 10.2 mmol) was stirred at 0° C. in CH$_2$Cl$_2$ (10 mL) and AcOH (5 mL) and treated with bromine (3.21 g, 20 mmol) in CH$_2$Cl$_2$ (10 mL) and AcOH (5 mL). After 18 hours the reaction was quenched with 20% aq. NaHSO$_3$ soln. (100 mL). The product was extracted with CH$_2$Cl$_2$ (3×40 mL) and washed with sat. aq. NaHCO$_3$ soln. (3×50 mL). The combined organic layer was dried through a cotton plug, concentrated and chromatographed on Silica gel to provide an oil (1.05 g, 28%). (TLC 30%EtOAc/hexanes $R_f$ 0.48). $^1$H NMR (CDCl$_3$) δ7.13 (m, 3H), 6.91 (m, 3H), 6.68 (d, J=8.0 Hz, 1H), 3.90 (s, 3H), 3.36 (s, 2H), 2.86–2.79 (4H), 2.67 (br d, J=9.0 Hz, 1H), 2.31 (br s, 1H), 2.28 (br s, 1H), 2.22 (br s, 1H), 1.78 (AB d, J=13.0 Hz, 2H). GCMS m/e 373,371 (M$^+$).

EXAMPLE 27

11-BENZYL-6-HYDROXY-5-METHOXY-11-AZA-TRICYCLO[7.3.1.0$^{2,7}$]TRIDECA-2(7),3,5-TRIENE

11-Benzyl-6-bromo-5-methoxy-11-aza-tricyclo[7.3.1.0$^{2,7}$]trideca-2(7),3,5-triene (1.05 g, 2.70 mmol) was stirred at −78 ° C. in anh. THF (10 mL) and treated with n-BuLi (1.08 mL. 2.5M soln. in hexanes, 2.70 mmol) dropwise over 1 min. After 10 min., triisopropyl borate (559 mg, 2.97 mmol) was added and the mixture was allowed to warm to ambient temperature. The reaction was quenched with with sat. aq. NaHCO$_3$ soln. (50 mL) and the product was extracted with EtOAc (3×20 mL). The organic layer was dried (MgSO$_4$), filtered and evaporated to give an oil (640 mg, 67%). (TLC 30%EtOAc/hexanes $R_f$ 0.18). This material (640 mg, 1.81 mmol) was stirred In THF (10 mL) with 30% aq. hydrogen peroxide soln. (205 mg, 1.81 mmol). After 18 hours the reaction was quenched with 20% aq. NaHSO$_3$ soln. (10 mL). The mixture was diluted with sat. aq. NaHCO$_3$ soln. (50 mL) and product was extracted with CH$_2$Cl$_2$ (3×40 mL). The organic layer washed with sat. aq. NaHCO$_3$ soln. (3×50 mL), dried through a cotton plug, concentrated and chromatographed on Silica gel to provide an oil (360 mg, 64%). (TLC 40%EtOAc/hexanes $R_f$ 0.44). $^1$H NMR (CDCl$_3$) δ7.14 (3H), 6.95 (2H), 6.67 (d, J=8.0 Hz, 1IH), 6.52 (d, J=8.0 Hz, 1H), 3.89 (s, 3H), 3.40 (AB d, 2H), 2.88–2.83 (5H), 2.34–2.22 (3H), 1.79 (AB d, 2H). GCMS m/e 309 (M$^+$).

EXAMPLE 28

6-HYDROXY-5-METHOXY-11-AZA-TRICYCLO[7.3.1.0$^{2,7}$]TRIDECA-2(7),3,5-TRIENE HYDROCHLORIDE

11-Benzyl-6-hydroxy-5-methoxy-11-aza-tricyclo[7.3.1.0$^{2,7}$]trideca-2(7),3,5-triene (58 mg, 0.18 mmol) was converted to the title compound according to the procedure described in Example 3 followed by conversion to the salt as described in Example 9 to provide a white solid (15 mg, 32%). (TLC 10%MeOH/CH$_2$Cl$_2$ (NH$_3$) $R_f$ 0.26). $^1$H NMR (CD$_3$OD) δ6.84 (d, J=8.0 Hz, 1H), 6.68 (d, J=8.0 Hz, 1H), 3.82 (s, 3H), 3.29 (3H), 3.13 (m, 2H), 3.00 (dd, J=18.0,6.0 Hz, 1H), 2.85 (d, J=18.0 Hz, 1H), 2.42 (m, 1H), 2.09 (AB d, J=12.5 Hz, 1H), 1.82 (AB d, J=12.5 Hz, 1H). mp 285–290° C.

EXAMPLE 29

TRIFLUORO-METHANESULFONIC ACID11-BENZYL-11-AZA-TRICYCLO[7.3.1.0$^{2,7}$]TRIDECA-2(7),3,5-TRIEN-5-YL ESTER

11-Benzyl-11-aza-tricyclo[7.3.1.0$^{2,7}$]trideca-2(7),3,5-trien-5-ol (850 mg, 3.03 mmol) was converted to the title compound (1.18 g, 94%) by the method described in Example 1D. (TLC 30%EtOAc/hexanes $R_f$ 0.47). $^1$H NMR (CDCl$_3$) δ7.10 (3H), 6.97 (3H), 6.78 (2H), 3.40 (AB d, J=14.0 Hz, 1H), 3.30 (AB d, J=14.0 Hz, 1H), 3.05 (AB dd, J=17.5,7.0 Hz, 1H), 2.89–2.79 (3H), 2.62 (d, J=10.0 Hz, 1H), 2.40 (d, J=10.5 Hz, 1H), 2,28 (d, J=12.0 Hz, 1H), 2.17 (br s,1H), 1.83 (AB d, 2H). APCI MS m/e 412.1 [(M+1)$^+$].

EXAMPLE 30

5-(4-TRIFLUOROMETHYL-PHENYL)-11-AZA-TRICYCLO[7.3.1.0$^{2,7}$]TRIDECA-2(7),3,5-TRIENE HYDROCHLORIDE

A) 11-Benzyl-5-(4-trifluoromethyl-ohenyl)-11-azatrcyclo[7.3.1.0$^{2,7}$]trideca-2(7),3,5-triene (For a discussion, see: Miyaura, N.; Suzuki, A. *Chem. Rev.* 1995, 95, 2457–2483.)

Trifluoro-methanesulfonic acid-11-benzyl-11-azatricyclo[7.3.1.0$^{2,7}$]trideca-2(7),3,5-trien-5-yl ester (258 mg, 0.63 mmol), potassium acetate (493 mg, 5.02 mmol) and 4-trifluoromethylphenyl boronic acid (141 mg, 0.94 mmol) were combined in 10/1 EtOH/H$_2$O (5 mL). The mixture was degassed (3 vacuum/N$_2$ cycles), treated with tetrakis (triphenylphosphine)palladium(0) (36.0 mg, 0.032 mmol) and warmed to 90 °C. for 18h. The reaction was cooled, diluted with H$_2$O and extracted with Et$_2$O (3×50 mL). The organic layer was washed with brine (50 mL), dried (MgSO$_4$), filtered and concentrated to provide an oil (60 mg, 23%). (TLC hexanes R$_f$ 0.16). $^1$H NMR (CDCl$_3$), δ7.73 (d, J=8.5 Hz, 2H), 7.68 (d, J=8.5 Hz, 2H), 7.38 (d, J=2.0 Hz, 1H), 7.32 (dd, J=8.0,2.0 Hz, 7.10 (4H), 6.88 (m, 2H), 3.40 (s, 2H), 3.14 (dd, J=17.5, 7.0 Hz, 1H), 2.94–2.87 (3H), 2.76 (d, J=10.5 Hz, 1H), 2.40 (dd, J=10.5,2.0 Hz, 1H), 2.33 (dd, J=10.5,2.0 Hz, 1H), 2.22 (brs, 1H), 1.91 (AB d, J=12.5 Hz, 1H), 1.83 (AB d, J=12.5 Hz, 1H). GCMS m/e 407 (M)$^+$.

B) 5-(4-Trifluoromethyl-phenyl)-11-aza-tricyclo [7.3.1.0$^{2,7}$]trideca-2(7),3,5-triene hydrochloride 11-Benzyl-5-(4-Trifluoromethyl-phenyl)-11-aza-trcyclo [7.3.1.0$^{2,7}$]trideca-2(7),3,5-triene was converted to the title compound as described in Example 3. (TLC 50%EtOAc/hexanes R$_f$ 0.81). $^1$H NMR (CDCl$_3$) δ7.62 (m, 4H), 7.15–6.98 (3H) 3.50–2.97 (6H), 2.92 (d, J=18.0 Hz, 1IH), 2.38 (brs, 1H), 2.02 (AB d, 2H).

EXAMPLE 31

5-(4-METHOXY-PHENYL)-11-AZA-TRICYCLO [7.3.1.0$^{2,7}$]TRIDECA-2(7),3,5-TRIENE HYDROCHLORIDE

Trifluoro-methanesulfonic acid-11-benzyl-11-aza-tricyclo[7.3.1.0$^{2,7}$]trideca-2(7),3,5-trien-5-yl ester and 4-methoxyphenyl boronic acid were converted to the title compound by the methods described in Example 30. $^1$H NMR (CD$_3$OD) δ7.57 (d, J=8.0 Hz, 2H), 7.42 (d, J=2.0 Hz, 1H), 7.38 (dd, J=8.0,2.0 Hz, 1H), 7.18 (d, J=8.0 Hz, 1H), 6.97 (d, J=8.0 Hz, 2H), 3.81 (s, 3H), 3.48–3.08 (6H), 2.95 (d, J=18.0 Hz, 1H), 2.30 (br s, 1H), 2.10 (AB d, J=11.5 Hz, 1H), 1.97 (AB d, J=11.5 Hz, 1H).

EXAMPLE 32

11-AZA-TRICYCLO[7.3.1.0$^{2,7}$]TRIDECA-2(7),3,5-TRIENE-5-CARBOXYLIC ACID METHYL ESTER HYDROCHLORIDE (Based on Dolle, R. E.; Schmidt, S. J.; Kruse, L I. *J. Chem. Soc., Chem. Commun.* 1987, 904–905.)

Trifluoro-methanesulfonic acid-11-benzyl-11-aza-tricyclo[7.3.1.0$^{2,7}$]trideca-2(7),3,5-trien-5-yl ester (1.0 g, 2.26 mmol) was dissolved in DMSO (15 mL) and MeOH (2 mL) and treated with triethylamine (505 mg, 4.99 mmol, potassium acetate (22.0 mg, 0.23 mmol) and 1,3-bis (diphenylphosphino)propane (94.0 mg, 0.23 mmol). This mixture was stirred and degassed (3 vacuum/N$_2$ purge cycles) then treated with palladium acetate (51 mg, 0.23 mmol). The system was purged with carbon monoxide gas (CO(g)) at balloon pressure, stirred 20 min., warmed to 100° C. for 3 hours, cooled and then poured into brine (50 mL). The resulting mixture was extracted with EtOAc (4×40 mL) and the combined organic layer was washed with a sat. aq. NaHCO$_3$ soln. (100 mL), H$_2$O (100 mL), brine (100 mL), dried (MgSO$_4$), filtered and evaporated to an oil. The oil, 11-benzyl-11-aza-tricyclo[7.3.1.0$^{2,7}$]trideca-2(7),3,5-triene-5-carboxylic acid methyl ester, was chromatographed on silica gel to provide an oil (280 mg, 38%). (TLC 10%EtOAc/hexanes R$_f$ 0.21). APCI MS m/e 322.2 [(M+ 1)$^+$]. This oil was converted Into the title compound by the methods described in Example 3. (TLC 10%CH$_2$Cl$_2$/MeOH (NH$_3$) R$_f$ 0.21). $^1$H NMR (CD$_3$OD) δ7.87 (d, J=2.0 Hz, 1H), 7.83 (dd, J=8.0,2.0 Hz,1H), 7.35 (d, J=8.0 Hz, 1H), 3.87 (s, 3H), 3.49–3.12 (6H), 2.97 (d, J=18.5 Hz, 1H), 2.52 (brs, 1H), 2.18 (AB d, J=11.5 Hz, 1H), 1.97 (AB d, J=11.5 Hz, 1H). mp 255–256° C.

EXAMPLE 33

2-(11-AZA-TRICYCLO[7.3.1.0$^{2,7}$]TRIDECA-2(7), 3,5TRIEN-5-YL)-PROPAN-2-OL HYDROCHLORIDE

11-Benzyl-11-aza-tricyclo[7.3.1.0$^{2,7}$]trideca-2(7),3,5-triene-5-carboxylic acid methyl ester (180 mg, 0.62 mmol) was stirred under N$_2$ at −78° C. in anh. THF (15 mL) and treated with excess methyl magnesiumbromide (~1 mL, 3M in THF). The resulting mixture was allowed to warm to ambient temperature and quenched with a sat. aq. NH$_4$Cl soln. (25 mL). The product was extracted with EtOAc (3×50 mL), washed with brine (50 mL), dried (MgSO$_4$), filtered and evaporated to an oil (100 mg, 50%). GCMS m/e 321 (M$^+$). This material was converted to the title compound by the methods described in Example 3. $^1$H NMR (CD$_3$OD) δ7.32 (OH), 7.24 (s, 1H), 7.16 (d, J=8.0 Hz, 1H), 7.08 (m, 1H), 3.50–3.12 (6H), 2.91 (d, J=18.5 Hz, 1H), 2.47 (br, s, 1H), 2.11 (AB d, J=11.5 Hz, 1H), 1.97 (AB d, J=11.5 Hz, 1H), 1.15 (s, 6H). mp 80–81° C.

EXAMPLE 34

5-Pyridin-3-yl-11-aza-tricyclo[7.3.1.0$^{1,7}$]trideca-2 (7),3,5-triene hydrochloride Trifluoro-methanesulfonic acid 11-benzyl-11-aza-tricyclo [7.3.1.0$^{2,7}$]trideca-2(7),3,5-trien-5-yl ester and diethyl-pyridin-3-yl-borane were converted to the title compound by the methods described in Example 30. $^1$H NMR (CD$_3$OD) δ9.14 (br s, 1H), 8.78 (m, 2H), 8.08 (m, 1H), 7.69 (d, J=2.0 Hz, 1H), 7.62 (dd, J=8.0,2.0 Hz,1H), 7.43 (d, J=8.0 Hz, 1H), 3.43–3.18 (6H), 3.05 (d, J=18.5 Hz, 1H), 2.56 (br s, 1H), 2.18 (AB d, J=11.5 Hz,1H), 2.02 (AB d, J=11.5 Hz, 1H). GCMS m/e 250 (M$^+$). mp 240–242° C.

What is claimed is:

1. A compound of the formula

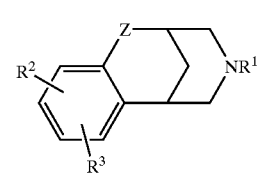

(I)

wherein

Z is CH$_2$, C(=O) or CF$_2$;

R$^1$ is hydrogen, (C$_1$–C$_6$)alkyl, unconjugated (C$_3$–C$_6$) alkenyl, benzyl, XC(=O)R$^{13}$ or —CH$_2$CH$_2$—O— (C$_1$–C$_4$)alkyl;

R$^2$ and R$^3$ are selected independently, from hydrogen, (C$_2$–C$_6$) alkenyl, (C$_2$–C$_6$) alkynyl, hydroxy, nitro, amino, halo, cyano, —SO$_q$(C$_1$–C$_6$)alkyl wherein q is zero, one or two, (C$_1$–C$_6$)alkylamino, [(C$_1$–C$_6$) alkyl]$_2$amino, CO$_2$R$^4$, CONR$^5$R$^6$, SO$_2$NR$^7$R$^8$, C(=O) R$^{13}$, XC(=O)R$^{13}$, aryl-(C$_0$–C$_3$)alkyl or aryl-(C$_0$–C$_3$) alkyl-O— wherein said aryl is selected from phenyl and naphthyl, heteroaryl-(C$_0$–C$_3$)alkyl or heteroaryl- (C$_{0-C3}$)alkyl-O—, wherein said heteroaryl is selected from five to seven membered aromatic rings containing from one to four heteroatoms selected from oxygen, nitrogen and sulfur, and $X^2(C_0–C_6)$alkoxy-$(C_0–C_6)$alkyl, wherein $X^2$ is absent or $X^2$ is $(C_1–C_6)$alkylamino or $[(C_1–C_6)$alkyl$]_2$amino, and wherein the $(C_0–C_6)$alkoxy-$(C_0–C_6)$alkyl moiety of said $X^2(C_0–C_6)$alkoxy-$(C_0–C_6)$alkyl contains at least one carbon atom, and wherein from one to three of the carbon atoms of said $(C_0–C_6)$alkoxy-$(C_0–C_6)$alkyl moiety may optionally be replaced by an oxygen, nitrogen or sulfur atom, with the proviso that any two such heteroatoms must be separated by at least two carbon atoms, and wherein any of the alkyl moieties of said $(C_0–C_6)$alkoxy-$(C_0–C_6)$alkyl may be optionally substituted with from two to seven fluorine atoms, and wherein one of the carbon atoms of each of the alkyl moieties of said aryl-$(C_0 C_3)$alkyl and said heteroaryl-$(C_0–C_3)$alkyl may optionally be replaced by an oxygen, nitrogen or sulfur atom, and wherein each of the foregoing aryl and heteroaryl groups may optionally be substituted with one or more substituents independently selected from $(C_1–C_6)$alkyl optionally substituted with from one to seven fluorine atoms, $(C_1–C_6)$ alkoxy optionally substituted with from two to seven fluorine atoms, halo, hydroxy, nitro, cyano, amino, $(C_1–C_6)$alkylamino and $[(C_1–C_6)$ alkyl$]_2$ amino;

each $R^4$, $R^5$, $R^6$, $R^7$, $R^8$ and $R^{13}$ is selected, independently, from hydrogen and $(C_1–C_6)$alkyl, or $R^5$ and $R^6$, or $R^7$ and $R^8$ together with the nitrogen to which they are attached, form a pyrrolidine, piperidine, morpholine, azetidine, piperazine, —N—$(C_1–C_6)$alkylpiperazine or thiomorpholine ring, or a thiomorpholine ring wherein the ring sulfur is replaced with a sulfoxide or sulfone; and each X is, independently, $(C_1–C_6)$alkylene;

with the proviso that: (a) at least one of $R^1$, $R^2$ and $R^3$ must be the other than hydrogen, (b) when $R^2$ and $R^3$ are hydrogen, $R^1$ cannot be methyl or hydrogen; and (c) in any of the fluoro substituted alkyl or alkoxy moieties of $R^2$ and $R^3$ the carbon atom adjacent to a heteroatom may not be monofluorinated;

or a pharmaceutically acceptable salt thereof.

2. A compound according to claim 1, wherein one or both of $R^2$ and $R^3$ are —C(=O)$R^{13}$ wherein $R^{13}$ is $(C_1–C)$alkyl.

3. A compound according to claim 1, wherein one of $R^2$ and $R^3$ is —COR$^{13}$ wherein $R^{13}$ is $(C_1–C_6)$alkyl or $(C_1–C_3)$ alkyl optionally substituted with from one to seven fluorine atoms.

4. A compound according to claim 1, wherein $R^2$ and $R^3$ are each independently selected from the group consisting of $CF_3$, fluoro, cyano or $C_2F_5$.

5. A compound according to claim 1 selected from the group consisting of
11-Azatricyclo[7.3.1.0$^{2,7}$]trideca-2(7),3,5-triene-5-carbonitrile;
11-Azatricyclo[7.3.1.0$^{2,7}$]trideca-2(7),3,5-triene-4-carbonitrile;
1-[11-Azatricyclo[7.3.1.0$^{2,7}$]trideca-2(7),3,5-trien-5-yl]-1-ethanone;
1-[11-Azatricyclo[7.3.1.0$^{2,7}$]trideca-2(7),3,5-trien-5-yl]-1-propanone;
4-Fluoro-11-azatricyclo[7.3.1.0$^{2,7}$]trideca-2(7),3,5-triene-5-carbonitrile;
5-Fluoro-11-azatricyclo[7.3.1.0$^{2,7}$]trideca-2(7),3,5-triene-4-carbonitrile;
1-[11-Azatricyclo[7.3.1.0$^{2,7}$]trideca-2(7),3,5-trien-4-yl]-1-ethanone;
1-[11-Azatricyclo[7.3.1.0$^{2,7}$]trideca-2(7),3,5-trien-4-yl]-1-propanone;
4,5-Difluoro-11-azatricyclo[7.3.1.0$^{2,7}$]trideca-2(7),3,5-triene;
4-chloro-5-fluoro-11-azatricyclo[7.3.1.0$^{2,7}$]trideca-2(7),3,5-triene;
5-Chloro-4-fluoro-11-azatricyclo[7.3.1.0$^{2,7}$]trideca-2(7),3,5-triene;
4-(1-Ethynyl)-5-fluoro-11-azatricyclo[7.3.1.0$^{2,7}$]trideca-2(7),3,5-triene;
5-(1-Ethynyl)-4-fluoro-11-azatricyclo[7.3.1.0$^{2,7}$]trideca-2(7),3,5-triene; and
4,5-Dichloro-11-azatricyclo[7.3.1.0$^{2,7}$]trideca-2(7),3,5-triene.

and pharmaceutically acceptable salts and optical isomers thereof.

6. A compound according to claim 1 selected from the group consisting of
5,6-difluoro-11-aza-tricyclo[7.3.1.0$^{2,7}$]trideca-2,4,6-triene;
11-benzyl-6-methoxy-11-aza-tricyclo[7.3.1.0$^{2,7}$]trideca-2(7),3,5-trien;
6-methoxy-11-aza-tricyclo[7.3.1.0$^{2,7}$]trideca-2(7),3,5-triene;
11-aza-tricyclo[7.3.1.0$^{2,7}$]trideca-2(7),3,5-trien-6-ol
6-fluoro-11-aza-tricyclo[7.3.1.0$^{2,7}$]trideca-2(7),3,5-triene;
11-benzyl-5-methoxy-11-aza-tricyclo[7.3.1.0$^{2,7}$]trideca-2(7),3,5-triene;
11-benzyl-11-aza-tricyclo[7.3.1.0$^{2,7}$]trideca-2(7),3,5-trien-5-ol;
5-methoxy-11-aza-tricyclo[7.3.1.0$^{2,7}$]trideca-2(7),3,5-triene;
11-aza-tricyclo[7.3.1.0$^{2,7}$]trideca-2(7),3,5-trien-5-ol;
11-benzyl-5-difluoromethoxy-11-aza-tricyclo[7.3.1.0$^{2,7}$]trideca-2(7),3,5-triene
5-difluoromethoxy-11-aza-tricyclo[7.3.1.0$^{2,7}$]trideca-2(7),3,5-triene;
11-benzyl-5-ethyl-11-aza-tricyclo[7.3.1.0$^{2,7}$]trideca-2(7),3,5-triene;
5-ethoxy-11-aza-tricyclo[7.3.1.0$^{2,7}$]trideca-2(7),3,5-triene;
5-isopropoxy-11-aza-tricyclo[7.3.1.0$^{2,7}$]trideca-2(7),3,5-triene;
11-benzyl-4-methoxy-11-aza-tricyclo[7.3.1.0$^{2,7}$]trideca-2(7),3,5-triene;
4-methoxy-11-aza-tricyclo [7.3.1.0$^{2,7}$]trideca-2(7),3,5-triene;
11-aza-tricyclo[7.3.1.0$^{2,7}$]trideca-2(7),3,5-trien-4-ol
11-benzyl-11-aza-tricyclo[7.3.1.0$^{2,7}$]trideca-2(7),3,5-triene;
11-aza-tricyclo[7.3.1.0$^{2,7}$]trideca-2(7),3,5-triene;
4-nitro-11-aza-tricyclo[7.3.1.0$^{2,7}$]trideca-2(7),3,5-triene;
5-nitro-11-aza-tricyclo[7.3.1.0$^{2,7}$]trideca-2(7),3,5-triene;
3-nitro-11-aza-tricyclo[7.3.1.0$^{2,7}$]trideca-2(7),3,5-triene;
11-benzyl-5-fluoro-11-aza-tricyclo[7.3.1.0$^{2,7}$]trideca-2(7),3,5-triene;
5-fluoro-11-aza-tricyclo[7.3.1.0$^{2,7}$]trideca-2(7),3,5-triene;
11-benzyl-6-bromo-5-methoxy-11-aza-tricyclo[7.3.1.0$^{2,7}$]trideca-2(7),3,5-triene
11-benzyl-6-hydroxy-5-methoxy-11-aza-tricyclo[7.3.1.0$^{2,7}$]trideca-2(7),3,5-triene
6-hydroxy-5-methoxy-11-aza-tricyclo[7.3.1.0$^{2,7}$]trideca-2(7),3,5-triene;
trifluoro-methanesulfonic acid-11-benzyl-11-aza-tricyclo[7.3.1.0$^{2,7}$]trideca-2(7),3,5-trien-5-yl ester
5-(4-trifluoromethyl-phenyl)-11-aza-tricyclo[7.3.1.0$^{2,7}$]trideca-2(7),3,5-triene;
5-(4-methoxy-phenyl)-11-aza-tricyclo[7.3.1.0$^{2,7}$]trideca-2(7),3,5-triene;
11-aza-tricyclo[7.3.1.0$^{2,7}$]trideca-2(7),3,5-triene-5-carboxylic acid methyl ester;
2-(11-aza-tricyclo[7.3.1.0$^{2,7}$]trideca-2(7),3,5-trien-5-yl)-propan-2-ol;

5-Pyridin-3-yl-11-aza-tricyclo[7.3.1.0$^{2,7}$]trideca-2(7),3,5-triene;

and pharmaceutically acceptable salts and optical isomers thereof.

7. A pharmaceutical composition for use in reducing nicotine addiction or aiding in the cessation or lessening of tobacco use in a mammal, comprising an amount of a compound according to claim 1 that is effective in reducing nicotine addiction or aiding in the cessation or lessening of tobacco use and a pharmaceutically acceptable carrier.

8. A pharmaceutical composition for treating a disorder or condition selected from inflammatory bowel disease, irritable bowel syndrome, spastic dystonia, chronic pain, acute pain, celiac sprue, pouchitis, vasoconstriction, anxiety, panic disorder, depression, bipolar disorder, autism, sleep disorders, jet lag, arnyotrophic lateral sclerosis (ALS), cognitive dysfunction, hypertension, bulimia, anorexia, obesity, cardiac arrhythmias, gastric acid hypersecretion, ulcers, pheochromocytoma, progressive supranuclear palsy, chemical dependencies and addictions, headache, stroke, TBI, obsessive-compulsive disorder (OCD), psychosis, Huntington's Chorea, tardive dyskinesia, hyperkinesia, dyslexia, schizophrenia, multi-infarct dementia, age related cognitive decline, epilepsy, including petit mal absence epilepsy, senile dementia of the Alzheimer's type (AD), Parkinson's disease (PD), attention deficit hyperactivity disorder (ADHD) and Tourette's Syndrome in a mammal, comprising an amount of a compound according to claim 1 that is effective in treating such disorder or condition and a pharmaceutically acceptable carrier.

9. A method for reducing nicotine addiction or aiding in the cessation or lessening of tobacco use in a mammal, comprising administering to said mammal an amount of a compound according to claim 1 that is effective in reducing nicotine addiction or aiding in the cessation or lessening of tobacco use.

10. A method for treating a disorder or condition selected from inflammatory bowel disease, irritable bowel syndrome, spastic dystonia, chronic pain, acute pain, celiac sprue, pouchitis, vasoconstriction, anxiety, panic disorder, depression, bipolar disorder, autism, sleep disorders, jet lag, amyotrophic lateral sclerosis (ALS), cognitive dysfunction, hypertension, bulimia, anorexia, obesity, cardiac arrhythmias, gastric acid hypersecretion, ulcers, pheochromocytoma, progressive supranuclear palsy, chemical dependencies and addictions, headache, stroke, TBI, obsessive-compulsive disorder (OCD), psychosis, Huntington's Chorea, tardive dyskinesia, hyperkinesia, dyslexia, schizophrenia, multi-infarct dementia, age related cognitive decline, epilepsy, including petit mal absence epilepsy, senile dementia of the Alzheimer's type (AD), Parkinson's disease (PD), attention deficit hyperactivity disorder (ADHD) and Tourette's Syndrome in a mammal, comprising administering to a mammal in need of such treatment an amount of a compound according to claim 1 that is effective in treating such disorder or condition.

* * * * *